(12) United States Patent
Boléa

(10) Patent No.: US 9,073,907 B2
(45) Date of Patent: *Jul. 7, 2015

(54) THIAZOLES DERIVATIVES AND THEIR USE AS POSITIVE ALLOSTERIC MODULATORS OF METABOTROPIC GLUTAMATE RECEPTORS

(75) Inventor: Christelle Boléa, Geneva (CH)

(73) Assignee: Addex Pharma S.A., Geneva (CH)

( * ) Notice: Subject to any disclaimer, the term of this patent is extended or adjusted under 35 U.S.C. 154(b) by 778 days.

This patent is subject to a terminal disclaimer.

(21) Appl. No.: 12/998,954

(22) PCT Filed: Jan. 12, 2010

(86) PCT No.: PCT/EP2010/050305
§ 371 (c)(1),
(2), (4) Date: Jun. 18, 2011

(87) PCT Pub. No.: WO2010/079239
PCT Pub. Date: Jul. 15, 2010

(65) Prior Publication Data
US 2011/0257179 A1    Oct. 20, 2011

(30) Foreign Application Priority Data
Jan. 12, 2009  (GB) .................................. 0900388.0

(51) Int. Cl.
C07D 417/12    (2006.01)
C07D 417/14    (2006.01)

(52) U.S. Cl.
CPC ............ C07D 417/12 (2013.01); C07D 417/14 (2013.01)

(58) Field of Classification Search
CPC ............................ C07D 417/14; C07D 417/12
USPC .......... 514/247, 341, 342, 272; 544/320, 331; 546/268.7, 270.7
See application file for complete search history.

(56) References Cited

U.S. PATENT DOCUMENTS 8,524,718 B2 * 9/2013 Bolea et al. .............. 514/255.05
2006/0194807 A1   8/2006 Cosford

FOREIGN PATENT DOCUMENTS

| WO | WO 2004/110350 | * | 12/2004 |
| WO | WO-2004/110350 A2 | | 12/2004 |
| WO | WO-2005/007096 A2 | | 1/2005 |
| WO | WO-2006/122011 A2 | | 11/2006 |
| WO | WO-2007/031440 A2 | | 3/2007 |
| WO | WO-2009/010455 A2 | | 1/2009 |
| WO | WO-2009/010871 A2 | | 1/2009 |
| WO | WO-2009/070871 A1 | | 6/2009 |

OTHER PUBLICATIONS

Thompson et al., Current Medicinal Chemistry, Oct. 2002, 9(19), pp. 1751-1762.*

Colagiuri et al., American Journal of Public Health, Sep. 2006, vol. 96, No. 9, pp. 1562-1569.*
Park, Diabetes Research and Clinical Practice 66S (2004), S33-S35.*
Curtis et al., The Journal of the American Board of Family Practice, vol. 18, pp. 37-43, (2005).*
Guttman et al., Canadian Medical Association Journal, Feb. 4, 2003, 168(3), pp. 293-301.*
Battaglia, G., et al., Pharmacological Activation of mGlu4 Metabotropic Glutamate Receptors Reduces . . . , Journal of Neuroscience, 2006, vol. 26(27), pp. 7222-7229.
Besong, G., et al., Activation of Group III Metabotropic Glutamate Receptors Inhibits the Production of RANTES . . . , Journal of Neuroscience, 2002, vol. 22(13), pp. 5403-5411.
Bradley, S., et al., Immunohistochemical Localization of Subtype 4a Metabotropic Glutamate Receptors . . . , Journal of Comparative Neurology, 1999, vol. 407, pp. 33-46.
Bruno, V., et al., Selective Activation of mGlu4 Metabotropic Glutamate Receptors is Protective . . . , Journal of Neuroscience, 2000, vol. 20(17), pp. 6413-6420.
Conn, P.J., et al., Metabotropic Glutamate Receptors in the Basal Ganglia Motor Circuit, Nature Review Neuroscience, 2005, vol. 6, pp. 787-798, Nature Publishing Group.
Corti, C., et al., Distribution and Synaptic Localisation of the Metabotropic Glutamate . . . , Neuroscience, 2002, vol. 110(3), pp. 403-420, Elsevier Science Ltd, Great Britain.
Engers, D., et al, Synthesis and Evaluation of a Series of Heterobiarylamides . . . , Journal of Medicinal Chemistry, 2009, vol. 52(14), pp. 4115-4118, American Chemical Society.
Johnson, M.P., et al., Modulation of Stress-Induced and Stimulated Hyperprolactinemia with the Group . . . , Neuropharmacology, 2002, vol. 43, pp. 799-808, Elsevier Science Ltd.
Johnson, M.P., et al., Discovery of Allosteric Potentiators . . . , Journal of Medicinal Chemistry, 2003, vol. 46(15), pp. 3189-3192, American Chemical Society.
Johnson, M.P., et al., Allosteric Modulators of Metabotropic Glutamate Receptors . . . , Biochemical Society Transactions, 2004, vol. 32(5), pp. 881-887, Biochemical Society.

(Continued)

Primary Examiner — Rebecca Anderson
(74) Attorney, Agent, or Firm — Law Offices of Gerard Bilotto, P.C.; Gerard Bilotto

(57) ABSTRACT

The present invention relates to novel compounds of Formula (I), wherein M, P, A and (B)$_n$ are defined as in Formula (I); invention compounds are modulators of metabotropic glutamate receptors—subtype 4 ("mGluR4") which are useful for the treatment or prevention of central nervous system disorders as well as other disorders modulated by mGluR4 receptors. The invention is also directed to pharmaceutical compositions and the use of such compounds in the manufacture of medicaments, as well as to the use of such compounds for the prevention and treatment of such diseases in which mGluR4 is involved.

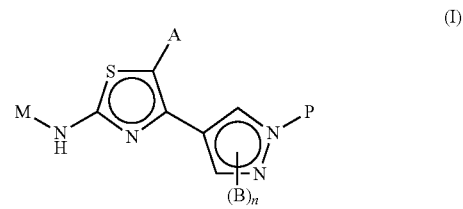

(I)

14 Claims, No Drawings

(56) References Cited

OTHER PUBLICATIONS

Kew, J., Positive and Negative Allosteric Modulation of Metabotropic Glutamate Receptors . . . , Pharmacology & Therapeutics, 2004, vol. 104(3), pp. 233-244, Elsevier Inc.

Knoflach, F., et al., Positive Allosteric Modulators of Metabotropic Glutamate 1 Receptor . . . , Proc. Natl. Acad. Sci. USA, 2001, vol. 98(23), pp. 13402-13407.

Konieczny, J., et al., The Influence of Group III Metabotropic Glutamate Receptor Stimulation by . . . , Neuroscience, 2007, vol. 145, pp. 611-620, Elsevier Ltd.

Lopez, S., et al., Targeting Group III Metabotropic Glutamate Receptors Produces . . . , Journal of Neuroscience, 2007, vol. 27(25), pp. 6701-6711, Society for Neuroscience.

Maj, M., et al., (−)-PHCCC a Positive Allosteric Modulator of mGluR4: Characterization, Mechanism of Action . . . , Neuropharmacology, 2003, vol. 45, pp. 895-906, Elsevier Ltd.

Marino, M., et al., Localization and Physiological Roles of Metabotropic Glutamate Receptors in the Direct and Indirect . . . , Amino Acids, 2002, vol. 23, pp. 185-191, Austria.

Marino, M., et al., Targeting the Metabotropic Glutamate Receptor . . . , Current Topics in Medicinal Chemistry, 2005, vol. 5(9), pp. 885-895, Bentham Science Publishers, Ltd.

Marino, M., et al., Allosteric Modulation of Group III Metabotropic Glutamate Receptor 4: A Potential . . . , Proc. Natl. Acad. Sci. USA, 2003, vol. 100(23), pp. 13668-13673.

Mathiesen, J., et al., Positive Allosteric Modulation of the Human Metabotropic . . . , British Journal of Pharmacology, 2003, vol. 138(6), pp. 1026-1030, Nature Publishing Group.

Millan, C., et al., Subtype-specific Expression of Group . . . , Journal of Biological Chemistry, 2002, vol. 277(49), pp. 47796-47803, American Soc. Biochem. & Molec. Biology Inc.

Mitsukawa, K., et al., A Selective Metabotropic Glutamate Receptor 7 Agonist: Activation of Receptor . . . , Proc. Natl. Acad. Sci. USA, 2005, vol. 102(51), pp. 18712-18717.

Monastyrskaia, K., et al., Effect of the Umami Peptides on the Ligand Binding and Function . . . , British Journal of Pharmacology, 1999, vol. 128, pp. 1027-1034, Stockton Press.

Mutel, V., Therapeutic Potential of Non-Competitive, Subtype-Selective Metabotropic . . . , Expert Opinion Ther. Patents, 2002, vol. 12(12), pp. 1-8, Ashley Publications Ltd.

Nakanishi, S., et al., Glutamate Receptors: Brain Function and Signal Transduction, Brain Research Reviews, 1998, vol. 26, pp. 230-235, Elsevier Science B.V.

Niswender, C., et al., Positive Allosteric Modulators of the Metabotropic Glutamate . . . , Bioorganic & Medicinal Chemistry Letters, 2008, vol. 18, pp. 5626-5630, Elsevier Ltd.

Niswender, C., et al., Discovery, Characterization, and . . . , Molecular Pharmacology, 2008, vol. 74(5), pp. 1345-1358, Amer. Soc. for Pharmacology & Experim. Therapeutics, USA.

O'Brien, J., et al., A Family of Highly Selective Allosteric . . . , Molecular Pharmacology, 2003, vol. 64(3), pp. 731-740, Amer.Soc. for Pharmacology & Experim.Therapeutics, USA.

Page, A., et al., Metabotropic Glutamate Receptors Inhibit Mechanosensitivity in Vagal . . . , Gastroenterology, 2005, vol. 128, pp. 402-410, American Gastroenterological Assoc.

Ritzen, A., et al., Molecular Pharmacology and Therapeutic Prospects . . . , Basic & Clinical Pharmacol. & Toxicol., 2005, vol. 97, pp. 202-213, Pharmacology & Toxicology,Denmark.

Schoepp, D., et al., Pharmacological Agents Acting at Subtypes of Metabotropic Glutamate Receptors, Neuropharmacology, 1999, vol. 38, pp. 1431-1476, Elsevier Science Ltd.

Stachowicz, K., et al., Anxiolytic-like effects of PHCCC, an allosteric modulator of mGlu4 . . . , European Journal of Pharmacology, 2004, vol. 498, pp. 153-156, Elsevier B.V.

Tatarczynska, E., et al., Anxiolytic- and Antidepressant-Like Effects of Group III . . . , Polish Journal of Pharmacol., 2002, vol. 54(6), pp. 707-710, Institute of Pharmacology.

Toyono, T., et al., Expression of the Metabotropic Glutamate Receptor, mGluR4A, in the Taste Hairs of Taste Buds in Rat . . . , Arch. Histol. Cytol., 2002, vol. 65(1), pp. 91-96.

Uehara, S., et al., Metabotropic Glutamate Receptor Type 4 is Involved in Autoinhibitory Cascade . . . , Diabetes, 2004, vol. 53, pp. 998-1006, American Diabetes Association.

Valenti, O., et al., Group III Metabotropic Glutamate Receptor-Mediated Modulation . . . , Journal of Neuroscience, 2003, vol. 23(18), pp. 7218-7226, Society for Neuroscience.

Valenti, O., et al., Group III Metabotropic . . . , Journal of Pharmacol. & Experim. Therapeutics, 2005, vol. 313(3), pp. 1296-1304, Amer. Soc. for Pharmacol.& Experim. Ther.,USA.

Vernon, A., et al., Neuroprotective Effects of Metabotropic . . . , European Journal of Neuroscience, 2005, vol. 22, pp. 1799-1806, Federation of European Neuroscience Societies.

Williams, R., et al., Positive Allosteric Modulators of the Metabotropic Glutamate . . . , Bioorganic & Medicinal Chemistry Letters, 2009, vol. 19, pp. 962-966, Elsevier Ltd.

Wilson, J., et al., Identification of Novel Positive Allosteric Modulators of mGlu8 Receptor, Neuropharmacology, 2005, vol. 49, p. 278.

Young, R., et al., Anatomy and Function of Group III Metabotropic Glutamate Receptors in Gastric Vagal Pathways, Neuropharmacology, 2008, vol. 54, pp. 965-975, Elsevier Ltd.

Singh,S.P.,et. al., A Facile Synthesis of 4-Pryazolylthiazoles and 4-Pyrazolylmercaptoimidazoles using . . . J.Indian Chem. Soc., 1997,vol. 74,pp. 940-942.

Yang,Ji, et. al., 3-(4-Pnenoxyphenyl)pyrazoles:A Novel Class of Sodium Channel Blockers. J. Med. Chem. 2004, vol. 47, pp. 1547-1552, American Chemical Society.

Lepoul, E.,et al., A potent and Selective mGluR4 Positive Allosteric Modulator Improves Movement . . . of Parkinson's Disease, J.Pharmacol. Exp. Ther. Jul. 11, 2012, DOI:10.1124.

Celanire, C., Discovery and characterization of novel . . . Positive Allosteric Modulators, 7th Int'l meeting of Metabotropic Glutamate Receptors in Taormina, Italy, Oct. 2011.

* cited by examiner

THIAZOLES DERIVATIVES AND THEIR USE AS POSITIVE ALLOSTERIC MODULATORS OF METABOTROPIC GLUTAMATE RECEPTORS

This application is a national stage application under 35 U.S.C. §371 of PCT/EP2020/059035, filed on Jan. 12, 2010, which claims benefit under 35 U.S.C. §119(a-d) and 365(b) from UK patent application GB0900388.0, filed on Jan. 12, 2009.

SUMMARY OF THE INVENTION

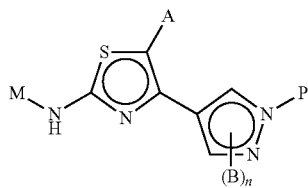

The present invention relates to novel compounds of Formula (I), wherein M, P, A and (B)$_n$ are defined as in Formula (I); invention compounds are modulators of metabotropic glutamate receptors—subtype 4 ("mGluR4") which are useful for the treatment or prevention of central nervous system disorders as well as other disorders modulated by mGluR4 receptors. The invention is also directed to pharmaceutical compositions and the use of such compounds in the manufacture of medicaments, as well as to the use of such compounds for the prevention and treatment of such diseases in which mGluR4 is involved.

BACKGROUND OF THE INVENTION

Glutamate is the major amino-acid transmitter in the mammalian central nervous system (CNS). Glutamate plays a major role in numerous physiological functions, such as learning and memory but also sensory perception, development of synaptic plasticity, motor control, respiration and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptor channels (iGluRs), namely the NMDA, AMPA and kainate receptors which are responsible for fast excitatory transmission (Nakanishi et al., (1998) Brain Res. Rev., 26:230-235).

In addition, glutamate activates metabotropic glutamate receptors (mGluRs) which have a more modulatory role that contributes to the fine-tuning of synaptic efficacy.

The mGluRs are G protein-coupled receptors (GPCRs) with seven-transmembrane spanning domains and belong to GPCR family 3 along with the calcium-sensing, GABAb and pheromone receptors.

The mGluR family is composed of eight members. They are classified into three groups (group I comprising mGluR1 and mGluR5; group II comprising mGluR2 and mGluR3; group III comprising mGluR4, mGluR6, mGluR7 and mGluR8) according to sequence homology, pharmacological profile and nature of intracellular signalling cascades activated (Schoepp et al., (1999) Neuropharmacology, 38:1431-1476).

Glutamate activates the mGluRs through binding to the large extracellular amino-terminal domain of the receptor, herein called the orthosteric binding site. This activation induces a conformational change of the receptor which results in the activation of the G-protein and intracellular signalling pathways.

In the central nervous system, mGluR4 receptors are expressed most intensely in the cerebellar cortex, basal ganglia, sensory relay nuclei of the thalamus and hippocampus (Bradley et al., (1999) Journal of Comparative Neurology, 407:33-46; Corti et al., (2002) Neuroscience, 110:403-420). The mGluR4 subtype is negatively coupled to adenylate cyclase via activation of the Gαi/o protein, is expressed primarily on presynaptic terminals, functioning as an autoreceptor or heteroreceptor and activation of mGluR4 leads to decreases in transmitter release from presynaptic terminals (Corti et al., (2002) Neuroscience, 110:403-420; Millan et al., (2002) Journal of Biological Chemistry, 277:47796-47803; Valenti et al., (2003) Journal of Neuroscience, 23:7218-7226).

Orthosteric agonists of mGluR4 are not selective and activate the other Group III mGluRs (Schoepp et al., (1999) Neuropharmacology, 38:1431-1476). The Group III orthosteric agonist L-AP4 was able to reduce motor deficits in animal models of Parkinson's disease (Valenti et al., (2003) J. Neurosci., 23:7218-7226) and decrease excitotoxicity (Bruno et al., (2000) J. Neurosci., 20; 6413-6420) and these effects appear to be mediated through mGluR4 (Marino et al., (2005) Curr. Topics Med. Chem., 5:885-895). In addition to LAP-4, ACPT-1, another selective group III mGluR agonist has been shown to caused a dose-and-structure dependant decrease in haloperidol-induced catalepsy and attenuated haloperidol-increased Proenkephalin mRNA expression in the striatum (Konieczny et al., (2007) Neuroscience, 145:611-620). Furthermore, Lopez et al. (2007, J. Neuroscience, 27:6701-6711) have shown that bilateral infusions of ACPT-I or LAP-4 into the globus pallidus fully reversed the severe akinetic deficits produced by 6-hydroxydopamine lesions of nigrostriatal dopamine neurons in a reaction-time task without affecting the performance of controls. In addition, the reversal of haloperidol-induced catalepsy by intrapallidal ACPT-1 was prevented by concomitant administration of a selective group III receptor antagonist (RS)-alpha-cyclopropyl-4-phosphonophenylglycine. The opposite effects produced by group III mGluR activation in the SNr strongly suggest a role of mGluR4 rather than others mGluR receptor sub-types in normalizing basal ganglia activity (Lopez et al. 2007).

These results suggest that, among mGluRs subtypes, mGluR4 is believed to be the most interesting novel drug target for the treatment of Parkinson's disease (for a review see Conn et al., (2005) Nature Review Neuroscience, 6:787-798).

Symptoms of Parkinson's disease appear to be due to an imbalance in the direct and indirect output pathways of the basal ganglia and reduction of transmission at the inhibitory GABAergic striato-pallidal synapse in the indirect pathway may result in alleviation of these symptoms (Marino et al., (2002) Amino Acids, 23:185-191).

mGluR4 is more abundant in striato-pallidal synapses than in striato-nigral synapses, and its localization suggests function as a presynaptic heteroreceptor on GABAergic neurons (Bradley et al., (1999) Journal of Comparative Neurology, 407:33-46) suggesting that selective activation or positive modulation of mGluR4 would decrease GABA release in this synapse thereby decreasing output of the indirect pathway and reducing or eliminating the Parkinson's disease symptoms. Classical treatment of Parkinsonism typically involves the use of levodopa combined with carbidopa (SINEMET™) or benserazide (MADOPAR™). Dopamine agonists such as bromocriptine (PARLODEL™), lisuride and pergolide (CELANCE™) act directly on dopamine receptors and are also used for the treatment of Parkinsonism. These molecules have the same side-effect profile as levodopa.

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for mGluR1, mGluR2, mGluR4, mGluR5, mGluR7 and mGluR8 (Knoflach F. et al. (2001) Proc. Natl. Acad. Sci. USA, 98:13402-13407; Johnson M. P. et al., (2002) Neuropharmacology, 43:799-808; O'Brien J. A. et al., (2003) Mol. Pharmacol., 64:731-740; Johnson M. P. et al., (2003) J. Med. Chem., 46:3189-3192; Marino M. J. et al., (2003) Proc. Natl. Acad. Sci. USA, 100:13668-13673; Mitsukawa K. et al., (2005) Proc. Natl. Acad. Sci. USA, 102(51):18712-18717; Wilson J. et al., (2005) Neuropharmacology, 49:278; for a review see Mutel V., (2002) Expert Opin. Ther. Patents, 12:1-8; Kew J. N., (2004) Pharmacol. Ther., 104(3):233-244; Johnson M. P. et al., (2004) Biochem. Soc. Trans., 32:881-887; recently Ritzen A., Mathiesen, J. M. and Thomsen C., (2005) Basic Clin. Pharmacol. Toxicol., 97:202-213).

In particular molecules have been described as mGluR4 positive allosteric modulators (Maj et al., (2003) Neuropharmacology, 45:895-906; Mathiesen et al., (2003) British Journal of Pharmacology, 138:1026-1030). It has been demonstrated that such molecules have been characterized in in vitro systems as well as in rat brain slices where they potentiated the effect of LAP-4 in inhibiting transmission at the striatopallidal synapse. These compounds do not activate the receptor by themselves (Marino et al., (2003) Proc. Nat. Acad. Sci. USA, 100:13668-13673). Rather, they enable the receptor to produce a maximal response to a concentration of glutamate or the Group III orthosteric agonist L-AP4 which by itself induces a minimal response.

PHCCC, a positive allosteric modulator of mGluR4 not active on other mGluRs (Maj et al., (2003) Neuropharmacology, 45:895-906), has been shown to be efficacious in animal models of Parkinson's disease thus representing a potential novel therapeutic approach for Parkinson's disease as well as for other motor disorders and disturbances (Marino et al., (2003) Proc. Nat. Acad. Sci. USA, 100:13668-13673), neurodegeneration in Parkinson's disease (Marino et al., (2005) Curr. Topics Med. Chem., 5:885-895; Valenti et al., (2005) J. Pharmacol. Exp. Ther., 313:1296-1304; Vernon et al., (2005) Eur. J. Neurosci., 22:1799-1806, Battaglia et al., (2006) J. Neurosci., 26:7222-7229), and neurodegeneration in Alzheimer's disease or due to ischemic or traumatic insult (Maj et al., (2003) Neuropharmacology, 45:895-906).

PHCCC also has been shown to be active in animal model of anxiety (Stachowicz et al., (2004) Eur. J. Pharmacol., 498: 153-156). Previously, ACPT-1 has been showed to produce a dose-dependent anti-conflict effect after intrahippocampal administration and anti-depressant-like effects in rats after intracerebroventricular administration (Tatarczynska et al., (2002) Pol. J. Pharmacol., 54(6):707-710).

Activation of mGluR4 receptors which are expressed in α- and F-cells in the islets of Langerhans inhibits glucagon secretion. Molecules which activate or potentiate agonist activity of these receptors may be an effective treatment for hyperglycemia, one of the symptoms of type 2 diabetes (Uehara et al., (2004) Diabetes, 53:998-1006).

The β-chemokine RANTES is importantly involved in neuronal inflammation and has been implicated in the pathophysiology of multiple sclerosis. Activation of Group III mGluRs with L-AP4 reduced the synthesis and release RANTES in wild-type cultured astrocytes, whereas the ability of L-AP4 to inhibit RANTES was greatly decreased in astrocyte cultures from mGluR4 knockout mice (Besong et al., (2002) Journal of Neuroscience, 22:5403-5411). These data suggest that positive allosteric modulators of mGluR4 may be an effective treatment for neuroinflammatory disorders of the central nervous system, including multiple sclerosis and related disorders.

Two different variants of the mGluR4 receptor are expressed in taste tissues and may function as receptors for the umami taste sensation (Monastyrskaia et al., (1999) Br. J. Pharmacol., 128:1027-1034; Toyono et al., (2002) Arch. Histol. Cytol., 65:91-96). Thus positive allosteric modulators of mGluR4 may be useful as taste agents, flavour agents, flavour enhancing agents or food additives.

There are anatomical evidence that the majority of vagal afferents innervating gastric muscle express group III mGluRs (mGluR4, mGluR6, mGluR7 and mGluR8) and actively transport receptors to their peripheral endings (Page et al., (2005) Gastroenterology, 128:402-10). Recently, it was shown that the activation of peripheral group III mGluRs inhibited vagal afferents mechanosensitivity in vitro which translates into reduced triggering of transient lower oesophageal sphincter relaxations and gastroesophageal reflux in vivo (Young et al., (2008) Neuropharmacol, 54:965-975). Labelling for mGluR4 and mGluR8 was abundant in gastric vagal afferents in the nodose ganglion, at their termination sites in the nucleus tractus solitarius and in gastric vagal motoneurons. These data suggest that positive allosteric modulators of mGluR4 may be an effective treatment for gastro-esophageal reflux disease (GERD) and lower esophageal disorders and gastro-intestinal disorders.

International patent publication WO2005/007096 describes mGluR4 receptor positive allosteric modulator useful, alone or in combination with a neuroleptic agent, for treating or preventing movement disorders. However, none of the specifically disclosed compounds are structurally related to the compounds of the invention.

More recently, new mGluR4 receptor positive allosteric modulators have been described: pyrazolo[3,4-d]pyrimidine derivatives (Niswender et al., (2008) Bioorganic & Medicinal Chemistry Letters, 18(20):5626-5630), functionalized benzylidene hydrazinyl-3-methylquinazoline and bis-2,3-dihydroquinazolin-4(1H)-one (Williams et al., (2009) Bioorganic & Medicinal Chemistry Letters, 19:962-966) and heterobiarylamides (Engers et al, (2009) Journal of Medicinal Chemistry, 52 (14), 4115-4118). Niswender et al., described (±)-cis-2-(3,5-dichlorophenylcarbamoyl)cyclohexane carboxylic acid ((2008) Molecular Pharmacology, 74(5): 1345-1358), as a positive allosteric modulator of mGluR4 also having agonist activity. This moderately active molecule has demonstrated evidence of efficacy following icy injection in rat models of Parkinson's disease. International patent publications WO2009/070871 and WO2009/010455 have mentioned amido derivatives and novel heteroaromatic derivatives, respectively, as positive allosteric modulators of metabotropic glutamate receptors.

International patent publication WO2004/110350 describes a class of aminothiazole compounds as modulators of amyloid-beta (Aβ) levels. Synthesis of 4-pyrazolylthiazoles and 4-pyrazolylmercaptoimidazoles using [hydroxyl(tosyloxy)iodo]benzene has been described by Singh et al. in (1997) Journal of the Indian Chemical Society, 74(11-12): 940-942.

(i) International patent publication WO2006/122011 describes 4-(2-(4-(octyloxy)-3-(trifluoromethyl)phenylamino)thiazol-4-yl)-1H-pyrazol-3-carbonitrile, having inhibitory activity on hepatitis C virus replication.

The present inventors have discovered novel thiazole compounds of general Formula (I) which surprisingly show potent activity and selectivity on mGluR4 receptor. The compounds of the invention demonstrate advantageous properties over compounds of the prior art. Improvements have been observed in one or more of the following characteristics of the compounds of the invention: the potency on the target, the selectivity for the target, the bioavailability, the brain penetration, and the activity in behavioural models.

Such thiazole derivatives are useful for treating or preventing a condition in a mammal, including a human, the treatment or prevention of which is affected or facilitated by the neuromodulatory effect of mGluR4 modulators. In the case of the treatment of movement disorders such as Parkinson's disease, the compounds of the invention can be used alone or in combination with an agent selected from the group consisting of: levodopa, levodopa with a selective extracerebral decarboxylase inhibitor, carbidopa, entacapone, a COMT inhibitor or a dopamine agonist.

DETAILED DESCRIPTION OF THE INVENTION

The invention relates to compounds having metabotropic glutamate receptor 4 modulator activity. In its most general compound aspect, the present invention provides a compound according to Formula (I),

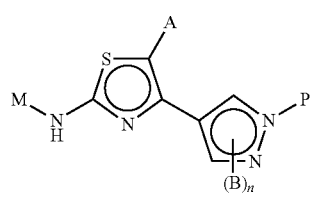

(I)

a pharmaceutically acceptable acid or base addition salt thereof, a stereochemically isomeric form thereof and an N-oxide form thereof, wherein:

A radical is selected from the group of hydrogen, halogen, —CN, —OH, —CF$_3$, —SH, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^1$, —O—(C$_2$-C$_6$)alkylene-OR$^1$, —NR$^1$(C$_2$-C$_6$)alkylene-OR$^2$, —(C$_3$-C$_7$)cycloalkyl-(C$_1$-C$_6$)alkyl, —O—(C$_3$-C$_7$)cycloalkyl-(C$_1$-C$_6$)alkyl, —NR$^1$—(C$_3$-C$_7$)cycloalkyl-(C$_1$-C$_6$)alkyl, —(C$_1$-C$_6$)haloalkylene-OR$^1$, —(C$_1$-C$_6$)haloalkylene-NR$^1$R$^2$, —(C$_0$-C$_6$)alkyl-S—R$^1$, —O—(C$_2$-C$_6$)alkylene-S—R$^1$, —NR$^1$—(C$_2$-C$_6$)alkylene-S—R$^2$, —(C$_0$-C$_6$)alkyl-S(=O)—R$^1$, —O—(C$_1$-C$_6$)alkylene-S(=O)—R$^1$, —NR$^1$—(C$_1$-C$_6$)alkylene-S(=O)—R$^2$, —(C$_0$-C$_6$)alkyl-S(=O)$_2$—R$^1$, —O—(C$_1$-C$_6$)alkylene-S(=O)$_2$—R$^1$, —NR$^1$—(C$_1$-C$_6$)alkylene-S(=O)$_2$—R$^2$, —(C$_0$-C$_6$)alkyl-NR$^1$R$^2$, —(C$_2$-C$_6$)alkylene-NR$^1$R$^2$, —NR$^1$—(C$_2$-C$_6$)alkylene-NR$^2$R$^3$, —(C$_0$-C$_6$)alkyl-S(=O)$_2$NR$^1$R$^2$, —O—(C$_1$-C$_6$)alkylene-S(=O)$_2$NR$^1$R$^2$, —NR$^1$—(C$_1$-C$_6$)alkylene-S(=O)$_2$NR$^2$R$^3$, —(C$_0$-C$_6$)alkyl-NR$^1$—S(=O)$_2$R$^2$, —O—(C$_2$-C$_6$)alkylene-NR$^1$—S(=O)$_2$R$^2$, —NR$^1$—(C$_2$-C$_6$)alkylene-NR$^2$—S(=O)$_2$R$^3$, —(C$_0$-C$_6$)alkyl-C(=O)—NR$^1$R$^2$, —O—(C$_1$-C$_6$)alkylene-C(=O)—NR$^1$R$^2$, —NR$^1$—(C$_1$-C$_6$)alkylene-C(=O)—NR$^2$R$^3$, —(C$_0$-C$_6$)alkyl-NR$^1$C(=O)—R$^2$, —O—(C$_2$-C$_6$)alkylene-NR$^1$C(=O)—R$^2$, —NR$^1$—(C$_2$-C$_6$)alkylene-NR$^2$C(=O)—R$^3$, —(C$_0$-C$_6$)alkyl-C(=O)—R$^1$, —O—(C$_1$-C$_6$)alkylene-C(=O)—R$^1$, —NR$^1$—(C$_1$-C$_6$)alkylene-C(=O)—R$^2$, —(C$_0$-C$_6$)alkyl-NR$^1$—C(=O)—NR$^2$R$^3$, —O—(C$_2$-C$_6$)alkylene-NR$^1$—C(=O)—NR$^2$R$^3$ and —NR$^1$—(C$_2$-C$_6$)alkylene-NR$^2$—C(=O)—NR$^3$R$^4$;

R$^1$, R$^2$, R$^3$ and R$^4$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

Any two radicals of R(R$^1$, R$^2$, R$^3$ or R$^4$) may be taken together to form an optionally substituted 3 to 10 membered carbocyclic or heterocyclic ring;

n is an integer ranging from 1 to 2;

(B)$_n$ radicals are each independently selected from the group of hydrogen, halogen, —CN, —OH, —CF$_3$, —SH, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^5$, —O—(C$_2$-C$_6$)alkylene-OR$^5$, —NR$^5$(C$_2$-C$_6$)alkylene-OR$^6$, —(C$_3$-C$_7$)cycloalkyl-(C$_1$-C$_6$)alkyl, —O—(C$_3$-C$_7$)cycloalkyl-(C$_1$-C$_6$)alkyl, —NR$^5$—(C$_3$-C$_7$)cycloalkyl-(C$_1$-C$_6$)alkyl, —(C$_1$-C$_6$)haloalkylene-OR$^5$, —(C$_1$-C$_6$)haloalkylene-NR$^5$R$^6$, —(C$_0$-C$_6$)alkyl-S—R$^5$, —O—(C$_2$-C$_6$)alkylene-S—R$^5$, —NR$^5$—(C$_2$-C$_6$)alkylene-S—R$^6$, —(C$_0$-C$_6$)alkyl-S(=O)—R$^5$, —O—(C$_1$-C$_6$)alkylene-S(=O)—R$^5$, —NR$^5$—(C$_1$-C$_6$)alkylene-S(=O)—R$^6$, —(C$_0$-C$_6$)alkyl-S(=O)$_2$—R$^5$, —O—(C$_1$-C$_6$)alkylene-S(=O)$_2$—R$^5$, —NR$^5$—(C$_1$-C$_6$)alkylene-S(=O)$_2$—R$^6$, —(C$_0$-C$_6$)alkyl-NR$^5$R$^6$, —O—(C$_2$-C$_6$)alkylene-NR$^5$R$^6$, —NR$^5$—(C$_2$-C$_6$)alkylene-NR$^6$R$^7$, —(C$_0$-C$_6$)alkyl-S(=O)$_2$NR$^5$R$^6$, —O—(C$_1$-C$_6$)alkylene-S(=O)$_2$NR$^5$R$^6$, —NR$^5$—(C$_1$-C$_6$)alkylene-S(=O)$_2$NR$^6$R$^7$, —(C$_0$-C$_6$)alkyl-NR$^5$—S(=O)$_2$R$^6$, —O—(C$_2$-C$_6$)alkylene-NR$^5$—S(=O)$_2$R$^6$, —NR$^5$—(C$_2$-C$_6$)alkylene-NR$^6$—S(=O)$_2$R$^7$, —(C$_0$-C$_6$)alkyl-C(=O)—NR$^5$R$^6$, —O—(C$_1$-C$_6$)alkylene-C(=O)—NR$^5$R$^6$, —NR$^5$—(C$_1$-C$_6$)alkylene-C(=O)—NR$^6$R$^7$, —(C$_0$-C$_6$)alkyl-NR$^5$C(=O)—R$^6$, —O—(C$_2$-C$_6$)alkylene-NR$^5$C(=O)—R$^6$, —NR$^5$—(C$_2$-C$_6$)alkylene-NR$^6$C(=O)—R$^7$, —(C$_0$-C$_6$)alkyl-C(=O)—R$^5$, —O—(C$_1$-C$_6$)alkylene-C(=O)—R$^5$, —NR$^5$—(C$_1$-C$_6$)alkylene-C(=O)—R$^6$, —(C$_0$-C$_6$)alkyl-NR$^5$—C(=O)—NR$^6$R$^7$, —O—(C$_2$-C$_6$)alkylene-NR$^5$—C(=O)—NR$^6$R$^7$ and —NR$^5$—(C$_2$-C$_6$)alkylene-NR$^6$—C(=O)—NR$^7$R$^8$;

R$^5$, R$^6$, R$^7$ and R$^8$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

M is selected from an optionally substituted 3 to 10 membered ring selected from the group of aryl, heteroaryl, heterocyclic and cycloalkyl;

P is selected from the group of a hydrogen or an optionally substituted radical selected from the group of —(C$_0$-C$_6$)alkyl-C(=O)—R$^9$, —(C$_1$-C$_6$)alkyl-CN, —(C$_2$-C$_6$)alkyl-S(O)—R$^9$, —(C$_0$-C$_6$)alkyl-C(=O)NR$^9$R$^{10}$, —(C$_2$-C$_6$)alkyl-NR$^9$C(=O)R$^{10}$ and —(C$_0$-C$_6$)alkyl-S(O)$_2$—R$^9$; and $R^9$ and $R^{10}$ are selected from the group of a hydrogen or an optionally substituted radical selected from the group of —$(C_1-C_6)$haloalkyl, —$(C_1-C_6)$alkyl, —$(C_1-C_6)$cyanoalkyl, —$(C_3-C_7)$cycloalkyl, —$(C_4-C_{10})$alkylene-cycloalkyl, heteroaryl, —$(C_1-C_6)$alkylene-heteroaryl, aryl, heterocycle and —$(C_1-C_6)$alkylene-aryl;

with the proviso (i) that:
when P is H, A is H, n is 1 and $B_1$ is —CN then M can not be an aryl substituted by octyloxy; and with the proviso that the compound is not:
4-(3-Methyl-1H-pyrazol-4-yl)-N-phenylthiazol-2-amine
4-(3-Methyl-1H-pyrazol-4-yl)-N-(pyridin-2-yl)thiazol-2-amine
N-(Pyridin-2-yl)-4-(3-(trifluoromethyl)-1H-pyrazol-4-yl)thiazol-2-amine
4-(3-Isopropyl-1H-pyrazol-4-yl)-N-(pyridin-2-yl)thiazol-2-amine
N-(2,6-Difluorophenyl)-4-(3-methyl-1H-pyrazol-4-yl)thiazol-2-amine
5-Methyl-4-(3-methyl-1H-pyrazol-4-yl)-N-(pyridin-2-yl)thiazol-2-amine
5-Methyl-4-(1H-pyrazol-4-yl)-N-(pyridin-2-yl)thiazol-2-amine
N-(2,5-Difluorophenyl)-4-(3-methyl-1H-pyrazol-4-yl)thiazol-2-amine
5-Methyl-N-(6-methylpyridin-2-yl)-4-(1H-pyrazol-4-yl)thiazol-2-amine
5-Methyl-N-(4-methylpyridin-2-yl)-4-(1H-pyrazol-4-yl)thiazol-2-amine
N-(3,5-Difluoropyridin-2-yl)-5-methyl-4-(1H-pyrazol-4-yl)thiazol-2-amine
4-(3-Methyl-1H-pyrazol-4-yl)-N-(4-methylpyridin-2-yl)thiazol-2-amine
5-Ethyl-4-(1H-pyrazol-4-yl)-N-(pyridin-2-yl)thiazol-2-amine
4-(3-Methyl-1H-pyrazol-4-yl)-N-(6-methylpyridin-2-yl)thiazol-2-amine
N-(5-Fluoropyridin-2-yl)-5-methyl-4-(1H-pyrazol-4-yl)thiazol-2-amine
4-(1H-Pyrazol-4-yl)-N-(pyridin-2-yl)thiazol-2-amine
2-Methyl-1-(4-(5-methyl-2-(pyridin-2-ylamino)thiazol-4-yl)-1H-pyrazol-1-yl)propan-1-one
4-(5-Methyl-2-(pyridin-2-ylamino)thiazol-4-yl)-1H-pyrazole-1-carboxamide
Cyclohexyl(4-(5-methyl-2-(pyridin-2-ylamino)thiazol-4-yl)-1H-pyrazol-1-yl)methanone
N-Cyclohexyl-5-methyl-4-(1H-pyrazol-4-yl)thiazol-2-amine
2-Methyl-1-(4-(5-methyl-2-(6-methylpyridin-2-ylamino)thiazol-4-yl)-1H-pyrazol-1-yl)propan-1-one
N-(6-Chloropyridin-2-yl)-5-methyl-4-(1H-pyrazol-4-yl)thiazol-2-amine
5-Chloro-4-(1H-pyrazol-4-yl)-N-(pyridin-2-yl)thiazol-2-amine
N-(6-Fluoropyridin-2-yl)-5-methyl-4-(1H-pyrazol-4-yl)thiazol-2-amine
(4-(5-Methyl-2-(pyridin-2-ylamino)thiazol-4-yl)-1H-pyrazol-1-yl)(piperidin-1-yl)methanone
N-Cyclopentyl-5-methyl-4-(1H-pyrazol-4-yl)thiazol-2-amine
5-Methyl-N-(pyrazin-2-yl)-4-(1H-pyrazol-4-yl)thiazol-2-amine
5-Methyl-4-(1-(methylsulfonyl)-1H-pyrazol-4-yl)-N-(pyridin-2-yl)thiazol-2-amine
N-(3-Fluoropyridin-2-yl)-5-methyl-4-(1H-pyrazol-4-yl)thiazol-2-amine
4-(1H-Pyrazol-4-yl)-2-(pyridin-2-ylamino)thiazol-5-carbonitrile
N-(6-Ethylpyridin-2-yl)-5-methyl-4-(1H-pyrazol-4-yl)thiazol-2-amine
N-(6-Chloropyridin-2-yl)-4-(1H-pyrazol-4-yl)thiazol-2-amine
N-Isopropyl-4-(5-methyl-2-(pyridin-2-ylamino)thiazol-4-yl)-1H-pyrazole-1-carboxamide
N-(6-Fluoropyridin-2-yl)-4-(1H-pyrazol-4-yl)thiazol-2-amine
5-Chloro-N-(6-methylpyridin-2-yl)-4-(1H-pyrazol-4-yl)thiazol-2-amine
N-(6-Methylpyridin-2-yl)-4-(1H-pyrazol-4-yl)thiazol-2-amine
4-(1H-Pyrazol-4-yl)-N-(pyridin-2-yl)-5-(trifluoromethyl)thiazol-2-amine
5-Phenyl-4-(1H-pyrazol-4-yl)-N-(pyridin-2-yl)thiazol-2-amine
5-Fluoro-4-(1H-pyrazol-4-yl)-N-(pyridin-2-yl)thiazol-2-amine
(4-(1H-Pyrazol-4-yl)-2-(pyridin-2-ylamino)thiazol-5-yl)methanol
N-(6-Methoxypyridin-2-yl)-5-methyl-4-(1H-pyrazol-4-yl)thiazol-2-amine
N-Cyclopropyl-4-(5-methyl-2-(pyridin-2-ylamino)thiazol-4-yl)-1H-pyrazole-1-carboxamide
4-(3-Cyclopropyl-1H-pyrazol-4-yl)-N-(pyridin-2-yl)thiazol-2-amine
4-(3-Ethyl-1H-pyrazol-4-yl)-N-(pyridin-2-yl)thiazol-2-amine and
4-(2-(6-Fluoropyridin-2-ylamino)-5-methylthiazol-4-yl)-1H-pyrazole-1-carboxamide.

In a more preferred aspect of Formula (I), the invention provides a compound wherein:
M is an optionally substituted pyridyl ring;
with the proviso that the compound is not:
4-(3-Methyl-1H-pyrazol-4-yl)-N-(pyridin-2-yl)thiazol-2-amine
N-(Pyridin-2-yl)-4-(3-(trifluoromethyl)-1H-pyrazol-4-yl)thiazol-2-amine
4-(3-Isopropyl-1H-pyrazol-4-yl)-N-(pyridin-2-yl)thiazol-2-amine
5-Methyl-4-(3-methyl-1H-pyrazol-4-yl)-N-(pyridin-2-yl)thiazol-2-amine
5-Methyl-4-(1H-pyrazol-4-yl)-N-(pyridin-2-yl)thiazol-2-amine
5-Methyl-N-(6-methylpyridin-2-yl)-4-(1H-pyrazol-4-yl)thiazol-2-amine
5-Methyl-N-(4-methylpyridin-2-yl)-4-(1H-pyrazol-4-yl)thiazol-2-amine
N-(3,5-Difluoropyridin-2-yl)-5-methyl-4-(1H-pyrazol-4-yl)thiazol-2-amine
4-(3-Methyl-1H-pyrazol-4-yl)-N-(4-methylpyridin-2-yl)thiazol-2-amine
5-Ethyl-4-(1H-pyrazol-4-yl)-N-(pyridin-2-yl)thiazol-2-amine
4-(3-Methyl-1H-pyrazol-4-yl)-N-(6-methylpyridin-2-yl)thiazol-2-amine
N-(5-Fluoropyridin-2-yl)-5-methyl-4-(1H-pyrazol-4-yl)thiazol-2-amine
4-(1H-Pyrazol-4-yl)-N-(pyridin-2-yl)thiazol-2-amine
2-Methyl-1-(4-(5-methyl-2-(pyridin-2-ylamino)thiazol-4-yl)-1H-pyrazol-1-yl)propan-1-one
4-(5-Methyl-2-(pyridin-2-ylamino)thiazol-4-yl)-1H-pyrazole-1-carboxamide
Cyclohexyl(4-(5-methyl-2-(pyridin-2-ylamino)thiazol-4-yl)-1H-pyrazol-1-yl)methanone 2-Methyl-1-(4-(5-methyl-2-(6-methylpyridin-2-ylamino)thiazol-4-yl)-1H-pyrazol-1-yl)propan-1-one
N-(6-Chloropyridin-2-yl)-5-methyl-4-(1H-pyrazol-4-yl)thiazol-2-amine
5-Chloro-4-(1H-pyrazol-4-yl)-N-(pyridin-2-yl)thiazol-2-amine
N-(6-Fluoropyridin-2-yl)-5-methyl-4-(1H-pyrazol-4-yl)thiazol-2-amine
(4-(5-Methyl-2-(pyridin-2-ylamino)thiazol-4-yl)-1H-pyrazol-1-yl)(piperidin-1-yl)methanone
5-Methyl-4-(1-(methylsulfonyl)-1H-pyrazol-4-yl)-N-(pyridin-2-yl)thiazol-2-amine
N-(3-Fluoropyridin-2-yl)-5-methyl-4-(1H-pyrazol-4-yl)thiazol-2-amine
4-(1H-Pyrazol-4-yl)-2-(pyridin-2-ylamino)thiazol-5-carbonitrile
N-(6-Ethylpyridin-2-yl)-5-methyl-4-(1H-pyrazol-4-yl)thiazol-2-amine
N-(6-Chloropyridin-2-yl)-4-(1H-pyrazol-4-yl)thiazol-2-amine
N-Isopropyl-4-(5-methyl-2-(pyridin-2-ylamino)thiazol-4-yl)-1H-pyrazole-1-carboxamide
N-(6-Fluoropyridin-2-yl)-4-(1H-pyrazol-4-yl)thiazol-2-amine
5-Chloro-N-(6-methylpyridin-2-yl)-4-(1H-pyrazol-4-yl)thiazol-2-amine
N-(6-Methylpyridin-2-yl)-4-(1H-pyrazol-4-yl)thiazol-2-amine
4-(1H-Pyrazol-4-yl)-N-(pyridin-2-yl)-5-(trifluoromethyl)thiazol-2-amine
5-Phenyl-4-(1H-pyrazol-4-yl)-N-(pyridin-2-yl)thiazol-2-amine
5-Fluoro-4-(1H-pyrazol-4-yl)-N-(pyridin-2-yl)thiazol-2-amine
(4-(1H-Pyrazol-4-yl)-2-(pyridin-2-ylamino)thiazol-5-yl)methanol
N-(6-Methoxypyridin-2-yl)-5-methyl-4-(1H-pyrazol-4-yl)thiazol-2-amine
N-Cyclopropyl-4-(5-methyl-2-(pyridin-2-ylamino)thiazol-4-yl)-1H-pyrazole-1-carboxamide
4-(3-Cyclopropyl-1H-pyrazol-4-yl)-N-(pyridin-2-yl)thiazol-2-amine
4-(3-Ethyl-1H-pyrazol-4-yl)-N-(pyridin-2-yl)thiazol-2-amine and
4-(2-(6-Fluoropyridin-2-ylamino)-5-methylthiazol-4-yl)-1H-pyrazole-1-carboxamide.

In a more preferred aspect of Formula (I), the invention provides a compound wherein:

A radical is selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^1$, —O—(C$_2$-C$_6$)alkylene-OR$^1$, —NR$^1$(C$_2$-C$_6$)alkylene-OR$^2$, —(C$_3$-C$_7$)cycloalkyl-(C$_1$-C$_6$)alkyl, —O—(C$_3$-C$_7$)cycloalkyl-(C$_1$-C$_6$)alkyl, —NR$^1$—(C$_3$-C$_7$)cycloalkyl-(C$_1$-C$_6$)alkyl, —(C$_1$-C$_6$)haloalkylene-OR$^1$, —(C$_1$-C$_6$)haloalkylene-NR$^1$R$^2$, —(C$_0$-C$_6$)alkyl-NR$^1$R$^2$, —O—(C$_2$-C$_6$)alkylene-NR$^1$R$^2$, —NR$^1$—(C$_2$-C$_6$)alkylene-NR$^2$R$^3$, —(C$_0$-C$_6$)alkyl-C(═O)—NR$^1$R$^2$, —O—(C$_1$-C$_6$)alkylene-C(═O)—NR$^1$R$^2$, —NR$^1$—(C$_1$-C$_6$)alkylene-C(═O)—NR$^2$R$^3$, —(C$_0$-C$_6$)alkyl-NR$^1$C(═O)—R$^2$, —O—(C$_2$-C$_6$)alkylene-NR$^1$C(═O)—R$^2$, —NR$^1$—(C$_2$-C$_6$)alkylene-NR$^2$C(═O)—R$^3$, —(C$_0$-C$_6$)alkyl-S(═O)$_2$—R$^1$, —(C$_0$-C$_6$)alkyl-C(═O)—R$^1$, —O—(C$_1$-C$_6$)alkylene-C(═O)—R$^1$ and —NR$^1$—(C$_1$-C$_6$)alkylene-C(═O)—R$^2$;

R$^1$, R$^2$ and R$^3$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

Any two radicals of R(R$^1$, R$^2$ or R$^3$) may be taken together to form an optionally substituted 3 to 10 membered carbocyclic or heterocyclic ring;

n is 1;

(B)$_n$ radicals are each independently selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^5$, —O—(C$_2$-C$_6$)alkylene-OR$^5$, —NR$^5$(C$_2$-C$_6$)alkylene-OR$^6$, —(C$_3$-C$_7$)cycloalkyl-(C$_1$-C$_6$)alkyl, —O—(C$_3$-C$_7$)cycloalkyl-(C$_1$-C$_6$)alkyl, —NR$^5$—(C$_3$-C$_7$)cycloalkyl-(C$_1$-C$_6$)alkyl, —(C$_1$-C$_6$)haloalkylene-OR$^5$, —(C$_1$-C$_6$)haloalkylene-NR$^5$R$^6$, —(C$_0$-C$_6$)alkyl-NR$^5$R$^6$, —O—(C$_2$-C$_6$)alkylene-NR$^5$R$^6$, —NR$^5$—(C$_2$-C$_6$)alkylene-NR$^6$R$^7$, —(C$_0$-C$_6$)alkyl-C(═O)—NR$^5$R$^6$, —O—(C$_1$-C$_6$)alkylene-C(═O)—NR$^5$R$^6$, —NR$^5$—(C$_1$-C$_6$)alkylene-C(═O)—NR$^6$R$^7$, —(C$_0$-C$_6$)alkyl-NR$^5$C(═O)—R$^6$, —O—(C$_2$-C$_6$)alkylene-NR$^5$C(═O)—R$^6$, —NR$^5$—(C$_2$-C$_6$)alkylene-NR$^6$C(═O)—R$^7$, —(C$_0$-C$_6$)alkyl-S(═O)$_2$—R$^5$, —(C$_0$-C$_6$)alkyl-C(═O)—R$^5$, —O—(C$_1$-C$_6$)alkylene-C(═O)—R$^5$ and —NR$^5$—(C$_1$-C$_6$)alkylene-C(═O)—R$^6$;

R$^5$, R$^6$ and R$^7$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

M is an optionally substituted pyridyl ring;

P is selected from the group of a hydrogen or an optionally substituted radical selected from the group of —(C$_0$-C$_6$)alkyl-C(═O)—R$^9$, —(C$_1$-C$_6$)alkyl-CN, —(C$_2$-C$_6$)alkyl-S(O)—R$^9$, —(C$_0$-C$_6$)alkyl-C(═O)NR$^9$R$^{10}$, —(C$_2$-C$_6$)alkyl-NR$^9$C(═O)R$^{10}$ and —(C$_0$-C$_6$)alkyl-S(O)$_2$—R$^9$; and R$^9$ and R$^{10}$ are selected from the group of a hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

with the proviso that the compound is not:
4-(3-Methyl-1H-pyrazol-4-yl)-N-(pyridin-2-yl)thiazol-2-amine
N-(Pyridin-2-yl)-4-(3-(trifluoromethyl)-1H-pyrazol-4-yl)thiazol-2-amine
4-(3-Isopropyl-1H-pyrazol-4-yl)-N-(pyridin-2-yl)thiazol-2-amine
5-Methyl-4-(3-methyl-1H-pyrazol-4-yl)-N-(pyridin-2-yl)thiazol-2-amine
5-Methyl-4-(1H-pyrazol-4-yl)-N-(pyridin-2-yl)thiazol-2-amine
5-Methyl-N-(6-methylpyridin-2-yl)-4-(1H-pyrazol-4-yl)thiazol-2-amine
5-Methyl-N-(4-methylpyridin-2-yl)-4-(1H-pyrazol-4-yl)thiazol-2-amine
N-(3,5-Difluoropyridin-2-yl)-5-methyl-4-(1H-pyrazol-4-yl)thiazol-2-amine
4-(3-Methyl-1H-pyrazol-4-yl)-N-(4-methylpyridin-2-yl)thiazol-2-amine 5-Ethyl-4-(1H-pyrazol-4-yl)-N-(pyridin-2-yl)thiazol-2-amine 4-(3-Methyl-1H-pyrazol-4-yl)-N-(6-methylpyridin-2-yl)thiazol-2-amine N-(5-Fluoropyridin-2-yl)-5-methyl-4-(1H-pyrazol-4-yl)thiazol-2-amine 4-(1H-Pyrazol-4-yl)-N-(pyridin-2-yl)thiazol-2-amine 2-Methyl-1-(4-(5-methyl-2-(pyridin-2-ylamino)thiazol-4-yl)-1H-pyrazol-1-yl)propan-1-one 4-(5-Methyl-2-(pyridin-2-ylamino)thiazol-4-yl)-1H-pyrazole-1-carboxamide Cyclohexyl(4-(5-methyl-2-(pyridin-2-ylamino)thiazol-4-yl)-1H-pyrazol-1-yl)methanone 2-Methyl-1-(4-(5-methyl-2-(6-methylpyridin-2-ylamino)thiazol-4-yl)-1H-pyrazol-1-yl)propan-1-one N-(6-Chloropyridin-2-yl)-5-methyl-4-(1H-pyrazol-4-yl)thiazol-2-amine 5-Chloro-4-(1H-pyrazol-4-yl)-N-(pyridin-2-yl)thiazol-2-amine N-(6-Fluoropyridin-2-yl)-5-methyl-4-(1H-pyrazol-4-yl)thiazol-2-amine (4-(5-Methyl-2-(pyridin-2-ylamino)thiazol-4-yl)-1H-pyrazol-1-yl)(piperidin-1-yl)methanone 5-Methyl-4-(1-(methylsulfonyl)-1H-pyrazol-4-yl)-N-(pyridin-2-yl)thiazol-2-amine N-(3-Fluoropyridin-2-yl)-5-methyl-4-(1H-pyrazol-4-yl)thiazol-2-amine 4-(1H-Pyrazol-4-yl)-2-(pyridin-2-ylamino)thiazol-5-carbonitrile N-(6-Ethylpyridin-2-yl)-5-methyl-4-(1H-pyrazol-4-yl)thiazol-2-amine N-(6-Chloropyridin-2-yl)-4-(1H-pyrazol-4-yl)thiazol-2-amine N-Isopropyl-4-(5-methyl-2-(pyridin-2-ylamino)thiazol-4-yl)-1H-pyrazole-1-carboxamide N-(6-Fluoropyridin-2-yl)-4-(1H-pyrazol-4-yl)thiazol-2-amine 5-Chloro-N-(6-methylpyridin-2-yl)-4-(1H-pyrazol-4-yl)thiazol-2-amine N-(6-Methylpyridin-2-yl)-4-(1H-pyrazol-4-yl)thiazol-2-amine 4-(1H-Pyrazol-4-yl)-N-(pyridin-2-yl)-5-(trifluoromethyl)thiazol-2-amine 5-Phenyl-4-(1H-pyrazol-4-yl)-N-(pyridin-2-yl)thiazol-2-amine 5-Fluoro-4-(1H-pyrazol-4-yl)-N-(pyridin-2-yl)thiazol-2-amine (4-(1H-Pyrazol-4-yl)-2-(pyridin-2-ylamino)thiazol-5-yl)methanol N-(6-Methoxypyridin-2-yl)-5-methyl-4-(1H-pyrazol-4-yl)thiazol-2-amine N-Cyclopropyl-4-(5-methyl-2-(pyridin-2-ylamino)thiazol-4-yl)-1H-pyrazole-1-carboxamide 4-(3-Cyclopropyl-1H-pyrazol-4-yl)-N-(pyridin-2-yl)thiazol-2-amine 4-(3-Ethyl-1H-pyrazol-4-yl)-N-(pyridin-2-yl)thiazol-2-amine and 4-(2-(6-Fluoropyridin-2-ylamino)-5-methylthiazol-4-yl)-1H-pyrazole-1-carboxamide.

In a more preferred aspect of Formula (I), the invention provides a compound wherein:

M is an optionally substituted pyrimidyl ring.

In a more preferred aspect of Formula (I), the invention provides a compound wherein:

A radical is selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^1$, —O—(C$_2$-C$_6$)alkylene-OR$^1$, —NR$^1$(C$_2$-C$_6$)alkylene-OR$^2$, —(C$_3$-C$_7$)cycloalkyl-(C$_1$-C$_6$)alkyl, —O—(C$_3$-C$_7$)cycloalkyl-(C$_1$-C$_6$)alkyl, —NR$^1$—(C$_3$-C$_7$)cycloalkyl-(C$_1$-C$_6$)alkyl, —(C$_1$-C$_6$)haloalkylene-OR$^1$, —(C$_1$-C$_6$)haloalkylene-NR$^1$R$^2$, —(C$_0$-C$_6$)alkyl-NR$^1$R$^2$, —O—(C$_2$-C$_6$)alkylene-NR$^1$R$^2$, —NR$^1$—(C$_2$-C$_6$)alkylene-NR$^2$R$^3$, —(C$_0$-C$_6$)alkyl-C(=O)—NR$^1$R$^2$, —O—(C$_1$-C$_6$)alkylene-C(=O)—NR$^1$R$^2$, —NR$^1$—(C$_1$-C$_6$)alkylene-C(=O)—NR$^2$R$^3$, —(C$_0$-C$_6$)alkyl-NR$^1$C(=O)—R$^2$, —O—(C$_2$-C$_6$)alkylene-NR$^1$C(=O)—R$^2$, —NR$^1$—(C$_2$-C$_6$)alkylene-NR$^2$C(=O)—R$^3$, —(C$_0$-C$_6$)alkyl-S(=O)$_2$—R$^1$, —(C$_0$-C$_6$)alkyl-C(=O)—R$^1$, —O—(C$_1$-C$_6$)alkylene-C(=O)—R$^1$ and —NR$^1$—(C$_1$-C$_6$)alkylene-C(=O)—R$^2$;

R$^1$, R$^2$ and R$^3$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

Any two radicals of R(R$^1$, R$^2$ or R$^3$) may be taken together to form an optionally substituted 3 to 10 membered carbocyclic or heterocyclic ring;

n is 1;

(B)$_n$ radicals are each independently selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^5$, —O—(C$_2$-C$_6$)alkylene-OR$^5$, —NR$^5$(C$_2$-C$_6$)alkylene-OR$^6$, —(C$_3$-C$_7$)cycloalkyl-(C$_1$-C$_6$)alkyl, —O—(C$_3$-C$_7$)cycloalkyl-(C$_1$-C$_6$)alkyl, —NR$^5$—(C$_3$-C$_7$)cycloalkyl-(C$_1$-C$_6$)alkyl, —(C$_1$-C$_6$)haloalkylene-OR$^5$, —(C$_1$-C$_6$)haloalkylene-NR$^5$R$^6$, —(C$_0$-C$_6$)alkyl-NR$^5$R$^6$, —O—(C$_2$-C$_6$)alkylene-NR$^5$R$^6$, —NR$^5$—(C$_2$-C$_6$)alkylene-NR$^6$R$^7$, —(C$_0$-C$_6$)alkyl-C(=O)—NR$^5$R$^6$, —O—(C$_1$-C$_6$)alkylene-C(=O)—NR$^5$R$^6$, —NR$^5$—(C$_1$-C$_6$)alkylene-C(=O)—NR$^6$R$^7$, —(C$_0$-C$_6$)alkyl-NR$^5$C(=O)—R$^6$, —O—(C$_2$-C$_6$)alkylene-NR$^5$C(=O)—R$^6$, —NR$^5$—(C$_2$-C$_6$)alkylene-NR$^6$C(=O)—R$^7$, —(C$_0$-C$_6$)alkyl-S(=O)$_2$—R$^5$, —(C$_0$-C$_6$)alkyl-C(=O)—R$^5$, —O—(C$_1$-C$_6$)alkylene-C(=O)—R$^5$ and —NR$^5$—(C$_1$-C$_6$)alkylene-C(=O)—R$^6$;

R$^5$, R$^6$ and R$^7$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

M is an optionally substituted pyrimidyl ring;

P is selected from the group of a hydrogen or an optionally substituted radical selected from the group of —(C$_0$-C$_6$)alkyl-C(=O)—R$^9$, —(C$_1$-C$_6$)alkyl-CN, —(C$_2$-C$_6$)alkyl-S(O)—R$^9$, —(C$_0$-C$_6$)alkyl-C(=O)NR$^9$R$^{10}$, —(C$_2$-C$_6$)alkyl-NR$^9$C(=O)R$^{10}$ and —(C$_0$-C$_6$)alkyl-S(O)$_2$—R$^9$; and R$^9$ and R$^{10}$ are selected from the group of a hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl.

In a preferred aspect, in Formula (I):

A radical is selected from the group of hydrogen, halogen, —CN, —OH, —CF$_3$, —NH$_2$ and an optionally substituted radical selected from the group of —(C$_1$-C$_6$)alkyl, —(C$_1$-C$_6$)

haloalkyl, —(C$_3$-C$_7$)cycloalkyl, —(C$_1$-C$_6$)cyanoalkyl, heterocycle, —(C$_0$-C$_6$)alkyl-OR$^1$, —NR$^1$(C$_2$-C$_6$)alkylene-OR$^2$ and —(C$_0$-C$_6$)alkyl-NR$^1$R$^2$;

R$^1$ and R$^2$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

Any two radicals of R(R$^1$ or R$^2$) may be taken together to form an optionally substituted 3 to 10 membered carbocyclic or heterocyclic ring;

n is 1;

(B)$_n$ radicals are each independently selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, aryl, heterocycle, —(C$_0$-C$_6$)alkyl-OR$^5$, —NR$^5$(C$_2$-C$_6$)alkylene-OR$^6$, —(C$_0$-C$_6$)alkyl-NR$^5$R$^6$, —(C$_0$-C$_6$)alkyl-S(=O)$_2$—R$^5$ and —(C$_0$-C$_6$)alkyl-C(=O)—R$^5$;

R$^5$ and R$^6$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

M is an optionally substituted heteroaryl or heterocycle;

P is selected from the group of a hydrogen or an optionally substituted radical selected from the group of —(C$_0$-C$_6$)alkyl-C(=O)—R$^9$, —(C$_0$-C$_6$)alkyl-C(=O)NR$^9$R$^{10}$, —(C$_2$-C$_6$)alkyl-NR$^9$C(=O)R$^{10}$ and —(C$_0$-C$_6$)alkyl-S(O)$_2$—R$^9$; and R$^9$ and R$^{10}$ are selected from the group of a hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

with the proviso that the compound is not:

4-(3-Methyl-1H-pyrazol-4-yl)-N-(pyridin-2-yl)thiazol-2-amine

N-(Pyridin-2-yl)-4-(3-(trifluoromethyl)-1H-pyrazol-4-yl)thiazol-2-amine 4-(3-Isopropyl-1H-pyrazol-4-yl)-N-(pyridin-2-yl)thiazol-2-amine 5-Methyl-4-(3-methyl-1H-pyrazol-4-yl)-N-(pyridin-2-yl)thiazol-2-amine 5-Methyl-4-(1H-pyrazol-4-yl)-N-(pyridin-2-yl)thiazol-2-amine 5-Methyl-N-(6-methylpyridin-2-yl)-4-(1H-pyrazol-4-yl)thiazol-2-amine 5-Methyl-N-(4-methylpyridin-2-yl)-4-(1H-pyrazol-4-yl)thiazol-2-amine N-(3,5-Difluoropyridin-2-yl)-5-methyl-4-(1H-pyrazol-4-yl)thiazol-2-amine 4-(3-Methyl-1H-pyrazol-4-yl)-N-(4-methylpyridin-2-yl)thiazol-2-amine 5-Ethyl-4-(1H-pyrazol-4-yl)-N-(pyridin-2-yl)thiazol-2-amine 4-(3-Methyl-1H-pyrazol-4-yl)-N-(6-methylpyridin-2-yl)thiazol-2-amine N-(5-Fluoropyridin-2-yl)-5-methyl-4-(1H-pyrazol-4-yl)thiazol-2-amine 4-(1H-Pyrazol-4-yl)-N-(pyridin-2-yl)thiazol-2-amine 2-Methyl-1-(4-(5-methyl-2-(pyridin-2-ylamino)thiazol-4-yl)-1H-pyrazol-1-yl)propan-1-one 4-(5-Methyl-2-(pyridin-2-ylamino)thiazol-4-yl)-1H-pyrazole-1-carboxamide Cyclohexyl(4-(5-methyl-2-(pyridin-2-ylamino)thiazol-4-yl)-1H-pyrazol-1-yl)methanone 2-Methyl-1-(4-(5-methyl-2-(6-methylpyridin-2-ylamino)thiazol-4-yl)-1H-pyrazol-1-yl)propan-1-one N-(6-Chloropyridin-2-yl)-5-methyl-4-(1H-pyrazol-4-yl)thiazol-2-amine 5-Chloro-4-(1H-pyrazol-4-yl)-N-(pyridin-2-yl)thiazol-2-amine N-(6-Fluoropyridin-2-yl)-5-methyl-4-(1H-pyrazol-4-yl)thiazol-2-amine (4-(5-Methyl-2-(pyridin-2-ylamino)thiazol-4-yl)-1H-pyrazol-1-yl)(piperidin-1-yl)methanone 5-Methyl-4-(1-(methylsulfonyl)-1H-pyrazol-4-yl)-N-(pyridin-2-yl)thiazol-2-amine N-(3-Fluoropyridin-2-yl)-5-methyl-4-(1H-pyrazol-4-yl)thiazol-2-amine 4-(1H-Pyrazol-4-yl)-2-(pyridin-2-ylamino)thiazol-5-carbonitrile N-(6-Ethylpyridin-2-yl)-5-methyl-4-(1H-pyrazol-4-yl)thiazol-2-amine N-(6-Chloropyridin-2-yl)-4-(1H-pyrazol-4-yl)thiazol-2-amine N-Isopropyl-4-(5-methyl-2-(pyridin-2-ylamino)thiazol-4-yl)-1H-pyrazole-1-carboxamide N-(6-Fluoropyridin-2-yl)-4-(1H-pyrazol-4-yl)thiazol-2-amine 5-Chloro-N-(6-methylpyridin-2-yl)-4-(1H-pyrazol-4-yl)thiazol-2-amine N-(6-Methylpyridin-2-yl)-4-(1H-pyrazol-4-yl)thiazol-2-amine 4-(1H-Pyrazol-4-yl)-N-(pyridin-2-yl)-5-(trifluoromethyl)thiazol-2-amine 5-Phenyl-4-(1H-pyrazol-4-yl)-N-(pyridin-2-yl)thiazol-2-amine 5-Fluoro-4-(1H-pyrazol-4-yl)-N-(pyridin-2-yl)thiazol-2-amine (4-(1H-Pyrazol-4-yl)-2-(pyridin-2-ylamino)thiazol-5-yl)methanol N-(6-Methoxypyridin-2-yl)-5-methyl-4-(1H-pyrazol-4-yl)thiazol-2-amine N-Cyclopropyl-4-(5-methyl-2-(pyridin-2-ylamino)thiazol-4-yl)-1H-pyrazole-1-carboxamide 4-(3-Cyclopropyl-1H-pyrazol-4-yl)-N-(pyridin-2-yl)thiazol-2-amine 4-(3-Ethyl-1H-pyrazol-4-yl)-N-(pyridin-2-yl)thiazol-2-amine and 4-(2-(6-Fluoropyridin-2-ylamino)-5-methylthiazol-4-yl)-1H-pyrazole-1-carboxamide.

Particular preferred compounds of the invention are compounds as mentioned in the following list (List of Particular Preferred Compounds), as well as a pharmaceutically acceptable acid or base addition salt thereof, a stereochemically isomeric form thereof and an N-oxide form thereof:

6-(5-Methyl-4-(1H-pyrazol-4-yl)thiazol-2-ylamino)picolinonitrile

5-Morpholino-4-(1H-pyrazol-4-yl)-N-(pyridin-2-yl)thiazol-2-amine 2-(5-Methyl-4-(1H-pyrazol-4-yl)thiazol-2-ylamino)nicotinonitrile 5-(Piperidin-1-yl)-4-(1H-pyrazol-4-yl)-N-(pyridin-2-yl)thiazol-2-amine 4-(3-(Furan-2-yl)-1H-pyrazol-4-yl)-N-(pyridin-2-yl)thiazol-2-amine 4-(3-(Cyclopropylmethyl)-1H-pyrazol-4-yl)-N-(pyridin-2-yl)thiazol-2-amine 4-(3-Isobutyl-1H-pyrazol-4-yl)-N-(pyridin-2-yl)thiazol-2-amine
4-(1H-Pyrazol-4-yl)-N-(pyridin-2-yl)-5-(pyrrolidin-1-yl)thiazol-2-amine
4-(1-(4-Chlorophenylsulfonyl)-1H-pyrazol-4-yl)-5-methyl-N-(pyridin-2-yl)thiazol-2-amine
5-Fluoro-N-(6-fluoropyridin-2-yl)-4-(1H-pyrazol-4-yl)thiazol-2-amine
5-Fluoro-N-(6-methylpyridin-2-yl)-4-(1H-pyrazol-4-yl)thiazol-2-amine
$N^5,N^5$-Dimethyl-4-(1H-pyrazol-4-yl)-$N^2$-(pyridin-2-yl)thiazole-2,5-diamine
N-(6-Chloropyridin-2-yl)-5-fluoro-4-(1H-pyrazol-4-yl)thiazol-2-amine
N-(6-Iodopyridin-2-yl)-5-methyl-4-(1H-pyrazol-4-yl)thiazol-2-amine
N-(3-Iodopyridin-2-yl)-5-methyl-4-(1H-pyrazol-4-yl)thiazol-2-amine
5-Methyl-4-(1H-pyrazol-4-yl)-N-(pyrimidin-2-yl)thiazol-2-amine
4-(5-Chloro-1H-pyrazol-4-yl)-N-(pyridin-2-yl)thiazol-2-amine
5-(Methoxymethyl)-4-(1H-pyrazol-4-yl)-N-(pyridin-2-yl)thiazol-2-amine
N-(4-Fluoropyridin-2-yl)-5-methyl-4-(1H-pyrazol-4-yl)thiazol-2-amine
5-((Diethylamino)methyl)-4-(1H-pyrazol-4-yl)-N-(pyridin-2-yl)thiazol-2-amine
5-(Morpholino methyl)-4-(1H-pyrazol-4-yl)-N-(pyridin-2-yl)thiazol-2-amine
5-(Ethoxymethyl)-4-(1H-pyrazol-4-yl)-N-(pyridin-2-yl)thiazol-2-amine
N-(3-Fluoro-6-methylpyridin-2-yl)-5-methyl-4-(1H-pyrazol-4-yl)thiazol-2-amine
N-(5-M ethoxypyridin-2-yl)-5-methyl-4-(1H-pyrazol-4-yl)thiazol-2-amine
5-Fluoro-N-(pyrazin-2-yl)-4-(1H-pyrazol-4-yl)thiazol-2-amine
4-(2-(Pyridin-2-ylamino)thiazol-4-yl)-1H-pyrazole-5-carbonitrile
N-(1-Methyl-1H-pyrazol-3-yl)-4-(1H-pyrazol-4-yl)thiazol-2-amine
5-Fluoro-N-(5-fluoropyridin-2-yl)-4-(1H-pyrazol-4-yl)thiazol-2-amine
N-(Pyridin-2-yl)-4-(3-(2,2,2-trifluoro ethyl)-1H-pyrazol-4-yl)thiazol-2-amine
4-(5-Fluoro-2-(6-methylpyridin-2-ylamino)thiazol-4-yl)-1H-pyrazole-1-carboxamide
N-(4-Methylpyrimidin-2-yl)-4-(1H-pyrazol-4-yl)thiazol-2-amine
N-Methyl-2-(4-(5-methyl-2-(pyridin-2-ylamino)thiazol-4-yl)-1H-pyrazol-1-yl)acetamide
5-Methyl-N-(4-methylpyrimidin-2-yl)-4-(1H-pyrazol-4-yl)thiazol-2-amine
5-Methyl-N-(5-methylpyrimidin-2-yl)-4-(1H-pyrazol-4-yl)thiazol-2-amine
4-(3-Fluoro-1H-pyrazol-4-yl)-N-(pyridin-2-yl)thiazol-2-amine
N,N-Dimethyl-4-(5-methyl-2-(pyridin-2-ylamino)thiazol-4-yl)-1H-pyrazole-1-carboxamide
4-(3-Phenyl-1H-pyrazol-4-yl)-N-(pyridin-2-yl)thiazol-2-amine
5-Methyl-4-(1H-pyrazol-4-yl)-N-(pyridin-4-yl)thiazol-2-amine
4-(3-(Phenylsulfonyl)-1H-pyrazol-4-yl)-N-(pyridin-2-yl)thiazol-2-amine
4-(3-(Methoxymethyl)-1H-pyrazol-4-yl)-N-(pyridin-2-yl)thiazol-2-amine
N-(2-Methylthiazol-4-yl)-4-(1H-pyrazol-4-yl)thiazol-2-amine
4-(1H-Pyrazol-4-yl)-N-(thiazol-2-yl)thiazol-2-amine
N-(6-(Fluoromethyl)pyridin-2-yl)-5-methyl-4-(1H-pyrazol-4-yl)thiazol-2-amine
N-(6-(Difluoromethyl)pyridin-2-yl)-5-methyl-4-(1H-pyrazol-4-yl)thiazol-2-amine
5-Chloro-4-(1H-pyrazol-4-yl)-N-(pyrimidin-2-yl)thiazol-2-amine
N-(4-Ethylpyrimidin-2-yl)-5-methyl-4-(1H-pyrazol-4-yl)thiazol-2-amine
N-(5-Fluoropyrimidin-2-yl)-5-methyl-4-(1H-pyrazol-4-yl)thiazol-2-amine
4-(5-(Dimethylamino)-1H-pyrazol-4-yl)-N-(pyridin-2-yl)thiazol-2-amine
5-Chloro-N-(4-methylpyrimidin-2-yl)-4-(1H-pyrazol-4-yl)thiazol-2-amine
3-(4-(1H-Pyrazol-4-yl)thiazol-2-ylamino)-1-methylpyrrolidin-2-one
4-(1H-Pyrazol-4-yl)-N-(pyrimidin-2-yl)-5-(trifluoromethyl)thiazol-2-amine
N-(4-Isopropylpyrimidin-2-yl)-5-methyl-4-(1H-pyrazol-4-yl)thiazol-2-amine
N-(4-Methoxypyrimidin-2-yl)-4-(1H-pyrazol-4-yl)thiazol-2-amine
1-(4-(2-(4-Methylpyrimidin-2-ylamino)thiazol-4-yl)-1H-pyrazol-5-yl)ethanone
N-(5-Fluoropyrimidin-2-yl)-4-(1H-pyrazol-4-yl)thiazol-2-amine
4-(5-(Dimethylamino)-1H-pyrazol-4-yl)-N-(4-methylpyrimidin-2-yl)thiazol-2-amine
N-(4-Methylpyrimidin-2-yl)-4-(3-(piperidin-1-yl)-1H-pyrazol-4-yl)thiazol-2-amine
N-(4-Methylpyrimidin-2-yl)-4-(1H-pyrazol-4-yl)-5-(trifluoromethyl)thiazol-2-amine
4-(1H-Pyrazol-4-yl)-N-(pyrimidin-2-yl)thiazol-2-amine
N-(4-Methylpyrimidin-2-yl)-4-(3-morpholino-1H-pyrazol-4-yl)thiazol-2-amine
N-((4-(5-Methyl-2-(pyridin-2-ylamino)thiazol-4-yl)-1H-pyrazol-1-yl)methyl)acetamide
N-(4-Cyclopropylpyrimidin-2-yl)-5-methyl-4-(1H-pyrazol-4-yl)thiazol-2-amine
(4-(5-Methyl-2-(pyridin-2-ylamino)thiazol-4-yl)-1H-pyrazol-1-yl)(pyridin-2-yl)methanone
4-(5-(Diethylamino)-1H-pyrazol-4-yl)-N-(4-methylpyrimidin-2-yl)thiazol-2-amine
4-(5-(Dimethylamino)-1H-pyrazol-4-yl)-N-(pyrimidin-2-yl)thiazol-2-amine
Cyclopropyl(4-(2-(pyrimidin-2-ylamino)thiazol-4-yl)-1H-pyrazol-5-yl)methanone
1-(4-(2-(Pyrimidin-2-ylamino)thiazol-4-yl)-1H-pyrazol-5-yl)ethanone
$N^5$-(2-Methoxyethyl)-$N^5$-methyl-4-(1H-pyrazol-4-yl)-$N^2$-(pyrimidin-2-yl)thiazole-2,5-diamine
N-(5-Fluoro-4-methylpyrimidin-2-yl)-4-(1H-pyrazol-4-yl)thiazol-2-amine
N-(5-Fluoro-4-methylpyrimidin-2-yl)-5-methyl-4-(1H-pyrazol-4-yl)thiazol-2-amine
4-(3-(Ethyl(methyl)amino)-1H-pyrazol-4-yl)-N-(pyrimidin-2-yl)thiazol-2-amine
4-(3-(Methylamino)-1H-pyrazol-4-yl)-N-(pyrimidin-2-yl)thiazol-2-amine
4-(5-(4-Fluorophenyl)-1H-pyrazol-4-yl)-N-(pyrimidin-2-yl)thiazol-2-amine 4-(5-(Methoxymethyl)-1H-pyrazol-4-yl)-N-(pyrimidin-2-yl)thiazol-2-amine 5-Cyclobutyl-4-(1H-pyrazol-4-yl)-N-(pyrimidin-2-yl)thiazol-2-amine N-(Pyrimidin-2-yl)-4-(3-(pyrrolidin-1-yl)-1H-pyrazol-4-yl)thiazol-2-amine 4-(3-((2-Methoxyethyl)(methyl)amino)-1H-pyrazol-4-yl)-N-(pyrimidin-2-yl)thiazol-2-amine N-(4-Methylpyrimidin-2-yl)-4-(3-(pyrrolidin-1-yl)-1H-pyrazol-4-yl)thiazol-2-amine N-(4-Methylpyrimidin-2-yl)-4-(3-phenyl-1H-pyrazol-4-yl)thiazol-2-amine (4-(2-(4-Methylpyrimidin-2-ylamino)thiazol-4-yl)-1H-pyrazol-3-yl)methanol 4-(3-(Methoxymethyl)-1H-pyrazol-4-yl)-N-(4-methylpyrimidin-2-yl)thiazol-2-amine 4-(3-(Ethylamino)-1H-pyrazol-4-yl)-N-(4-methylpyrimidin-2-yl)thiazol-2-amine and 4-(3-(2-Methoxyethyl)-1H-pyrazol-4-yl)-N-(4-methylpyrimidin-2-yl)thiazol-2-amine.

DEFINITION OF TERMS

Listed below are definitions of various terms used in the specification and claims to describe the present invention.

For the avoidance of doubt it is to be understood that in this specification "$(C_1-C_6)$" means a carbon radical having 1, 2, 3, 4, 5 or 6 carbon atoms. "$(C_0-C_6)$" means a carbon radical having 0, 1, 2, 3, 4, 5 or 6 carbon atoms. In this specification "C" means a carbon atom, "N" means a nitrogen atom, "O" means an oxygen atom and "S" means a sulphur atom.

In the case where a subscript is the integer 0 (zero) the radical to which the subscript refers, indicates that the radical is absent, i.e. there is a direct bond between the radicals.

In this specification, unless stated otherwise, the term "bond" refers to a saturated covalent bond. When two or more bonds are adjacent to one another, they are assumed to be equal to one bond. For example, a radical -A-B—, wherein both A and B may be a bond, the radical is depicting a single bond.

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl, i-hexyl or t-hexyl. The term "$(C_0-C_3)$alkyl" refers to an alkyl radical having 0, 1, 2 or 3 carbon atoms and may be methyl, ethyl, n-propyl and i-propyl.

In this specification, unless stated otherwise, the term "alkylene" includes both straight and branched difunctional saturated hydrocarbon radicals and may be methylene, ethylene, n-propylene, i-propylene, n-butylene, i-butylene, s-butylene, t-butylene, n-pentylene, i-pentylene, t-pentylene, neopentylene, n-hexylene, i-hexylene or t-hexylene.

In this specification, unless stated otherwise, the term "cycloalkyl" refers to an optionally substituted carbocycle containing no heteroatoms, including mono-, bi-, and tricyclic saturated carbocycles, as well as fused ring systems. Such fused ring systems can include one ring that is partially or fully unsaturated such as a benzene ring to form fused ring systems such as benzo-fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl and 1,2,3,4-tetrahydronaphthalene and the like. The term "$(C_3-C_7)$cycloalkyl" may be cyclopropyl, cyclobutyl, cyclopentyl, cyclohexyl, cycloheptyl and the like.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl, indenyl and the like.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thienyl, pyridyl, thiazolyl, isothiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl, thiadiazolyl, benzoimidazolyl, benzooxazolyl, benzothiazolyl, tetrahydrotriazolopyridyl, tetrahydrotriazolopyrimidinyl, benzofuryl, benzothiophenyl, thionaphthyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridyl, oxazolopyridyl, thiazolopyridyl, imidazopyridazinyl, oxazolopyridazinyl, thiazolopyridazinyl, cynnolyl, pteridinyl, furazanyl, benzotriazolyl, pyrazolopyridinyl and purinyl.

In this specification, unless stated otherwise, the term "alkylene-aryl", "alkylene-heteroaryl" and "alkylene-cycloalkyl" refers respectively to a substituent that is attached via the alkyl radical to an aryl, heteroaryl or cycloalkyl radical, respectively. The term "$(C_1-C_6)$alkylene-aryl" includes aryl-$C_1$-$C_6$-alkyl radicals such as benzyl, 1-phenylethyl, 2-phenylethyl, 1-phenylpropyl, 2-phenylpropyl, 3-phenylpropyl, 1-naphthylmethyl and 2-naphthylmethyl. The term "$(C_1-C_6)$alkylene-heteroaryl" includes heteroaryl-$C_1$-$C_6$-alkyl radicals, wherein examples of heteroaryl are the same as those illustrated in the above definition, such as 2-furylmethyl, 3-furylmethyl, 2-thienylmethyl, 3-thienylmethyl, 1-imidazolylmethyl, 2-imidazolylmethyl, 3-imidazolylmethyl, 2-oxazolylmethyl, 3-oxazolylmethyl, 2-thiazolylmethyl, 3-thiazolylmethyl, 2-pyridylmethyl, 3-pyridylmethyl, 4-pyridylmethyl, 1-quinolylmethyl or the like.

In this specification, unless stated otherwise, the term "heterocycle" refers to an optionally substituted, monocyclic or bicyclic saturated, partially saturated or unsaturated ring system containing at least one heteroatom selected independently from N, O and S.

In this specification, unless stated otherwise, a 5- or 6-membered ring containing one or more atoms independently selected from C, N, O and S, includes aromatic and heteroaromatic rings as well as carbocyclic and heterocyclic rings which may be saturated or unsaturated. Examples of such rings may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, tetrahydrothiopyranyl, oxazolidinonyl, thiomorpholinyl, oxadiazolyl, thiadiazolyl, tetrazolyl, phenyl, cyclohexyl, cyclopentyl, cyclohexenyl and cyclopentenyl.

In this specification, unless stated otherwise, a 3- to 10-membered ring containing one or more atoms independently selected from C, N, O and S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, tetrahydrothiopyranyl, furyl, pyrrolyl, isoxazolyl, isothiazolyl, oxazolyl, oxazolidinonyl, pyrazinyl, pyrazolyl, pyridazinyl, pyridyl, pyrimidyl, pyrrolyl, thiazolyl, thienyl, imidazolyl, triazolyl, phenyl, cyclopropyl, aziridinyl, cyclobutyl, azetidinyl, oxadiazolyl, thiadiazolyl, tetrazolyl, cyclopentyl, cyclopentenyl, cyclohexyl, cyclohexenyl, cycloheptyl, cycloheptenyl, cyclooctyl and cyclooctenyl.

In this specification, unless stated otherwise, the term "halo" or "halogen" may be fluoro, chloro, bromo or iodo.

In this specification, unless stated otherwise, the term "haloalkyl" means an alkyl radical as defined above, substituted with one or more halo radicals. The term "$(C_1-C_6)$ haloalkyl" may include, but is not limited to, fluoromethyl, difluoromethyl, trifluoromethyl, fluoroethyl and difluoroethyl. The term "$O-C_1-C_6$-haloalkyl" may include, but is not limited to, fluoromethoxy, difluoromethoxy, trifluoromethoxy and fluoro ethoxy.

In this specification, unless stated otherwise, the term "haloalkylene" means an alkylene radical as defined above, substituted with one or more halo radicals. The term "$(C_1-C_6)$haloalkylene" may include, but is not limited to, fluoromethylene, difluoromethylene, fluoroethylene and difluoroethylene. The term "$O-C_1-C_6$-haloalkylene" may include, but is not limited to, fluoromethylenoxy, difluoromethylenoxy and fluoroethylenoxy.

In this specification, unless stated otherwise, the term "cyanoalkyl" means an alkyl radical as defined above, substituted with one or more cyano.

In this specification, unless stated otherwise, the term "optionally substituted" refers to radicals further bearing one or more substituents which may be, $(C_1-C_6)$alkyl, hydroxy, $(C_1-C_6)$alkylene-oxy, mercapto, aryl, heterocycle, halogen, trifluoromethyl, pentafluoroethyl, cyano, cyanomethyl, nitro, amino, amido, amidinyl, carboxyl, carboxamide, $(C_1-C_6)$ alkylene-oxycarbonyl, carbamate, sulfonamide, ester and sulfonyl.

In this specification, unless stated otherwise, the term "solvate" refers to a complex of variable stoichiometry formed by a solute (e.g. a compound of Formula (I)) and a solvent. The solvent is a pharmaceutically acceptable solvent as preferably water; such solvent may not interfere with the biological activity of the solute.

In this specification, unless stated otherwise, the term "positive allosteric modulator of mGluR4" or "allosteric modulator of mGluR4" refers also to a pharmaceutically acceptable acid or base addition salt thereof, a stereochemically isomeric form thereof and an N-oxide form thereof.

In one embodiment, the term "compound" also embraces or includes pharmaceutically acceptable acid or base addition salts thereof, and/or stereochemically isomeric forms thereof and/or N-oxide forms thereof.

Pharmaceutical Compositions

Allosteric modulators of mGluR4 described herein, and the pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The allosteric modulators of mGluR4 will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

The amount of allosteric modulators of mGluR4, administered to the subject will depend on the type and severity of the disease or condition and on the characteristics of the subject, such as general health, age, sex, body weight and tolerance to drugs. The skilled artisan will be able to determine appropriate dosages depending on these and other factors. Effective dosages for commonly used CNS drugs are well known to the skilled person. The total daily dose usually ranges from about 0.05-2000 mg.

The present invention relates to pharmaceutical compositions which provide from about 0.01 to 1000 mg of the active ingredient per unit dose. The compositions may be administered by any suitable route. For example orally in the form of capsules and the like, parenterally in the form of solutions for injection, topically in the form of onguents or lotions, ocularly in the form of eye-drops, rectally in the form of suppositories, intranasally or transcutaneously in the form of delivery system like patches.

For oral administration, the allosteric modulators of mGluR4 thereof can be combined with a suitable solid or liquid carrier or diluent to form capsules, tablets, pills, powders, syrups, solutions, suspensions and the like.

The tablets, pills, capsules, and the like contain from about 0.01 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parenteral administration the disclosed allosteric modulators of mGluR4 can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

Preferably disclosed allosteric modulators of mGluR4 or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Classical treatment of Parkinsonism typically involves the use of levodopa combined with carbidopa (SINEMET™) or benserazide (MADOPAR™). Dopamine agonists such as bromocriptine (PARLODEL™), lisuride and pergolide (CELANCE™) act directly on dopamine receptors and are also used for the treatment of Parkinsonism.

Methods of Synthesis

The compounds according to the invention, in particular the compounds according to the Formula (I), may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (Green T. W. and Wuts P. G. M., (1991) *Protecting Groups in Organic Synthesis*, John Wiley & Sons). These groups are removed at a convenient stage of the compound synthesis using methods that are readily apparent to those skilled in the art. The selection of process as well as the reaction conditions and order of their execution shall be consistent with the preparation of compounds of Formula (I).

The compounds according to the invention may be represented as a mixture of enantiomers, which may be resolved into the individual pure R- or S-enantiomers. If for instance, a particular enantiomer is required, it may be prepared by asymmetric synthesis or by derivation with a chiral auxiliary, where the resulting diastereomeric mixture is separated and the auxiliary group cleaved to provide the pure desired enantiomers. Alternatively, where the molecule contains a basic functional group such as an amino or an acidic functional group such as carboxyl, this resolution may be conveniently performed by fractional crystallization from various solvents as the salts of an optical active acid or by other methods known in the literature (e.g. chiral column chromatography).

Resolution of the final product, an intermediate or a starting material may be performed by any suitable method known in the art (Eliel E. L., Wilen S. H. and Mander L. N., (1984) *Stereochemistry of Organic Compounds*, Wiley-Interscience).

Many of the heterocyclic compounds of the invention can be prepared using synthetic routes well known in the art (Katrizky A. R. and. Rees C. W., (1984) *Comprehensive Heterocyclic Chemistry*, Pergamon Press).

The product from the reaction can be isolated and purified employing standard techniques, such as extraction, chromatography, crystallization and distillation.

The compounds of the invention may be prepared by general route of synthesis as disclosed in the following methods.

In one embodiment of the present invention compounds of Formula (I) may be prepared according to the synthetic sequences illustrated in Scheme 1. A well known procedure to synthetise pyrazole is from ketoester g1 which is condensed with 1,1-dimethoxy-N,N-dimethylmethanamine followed by cyclisation in the presence of hydrazine. Pyrazole g3 can be protected by p-methoxybenzyl using standard conditions. Then compound g4 may be hydrolyzed by standard procedures followed by reaction with oxalyl chloride to yield compound g6. Subsequently, the acid chloride can be transformed into bromoketone g7 via formation of diazoketone. Then cyclization reaction may be performed between thiourea g8 and bromoketone g7 to yield aminothiazole g9. Finally, g9 can be deprotected with classical conditions well known for people skilled in the art.

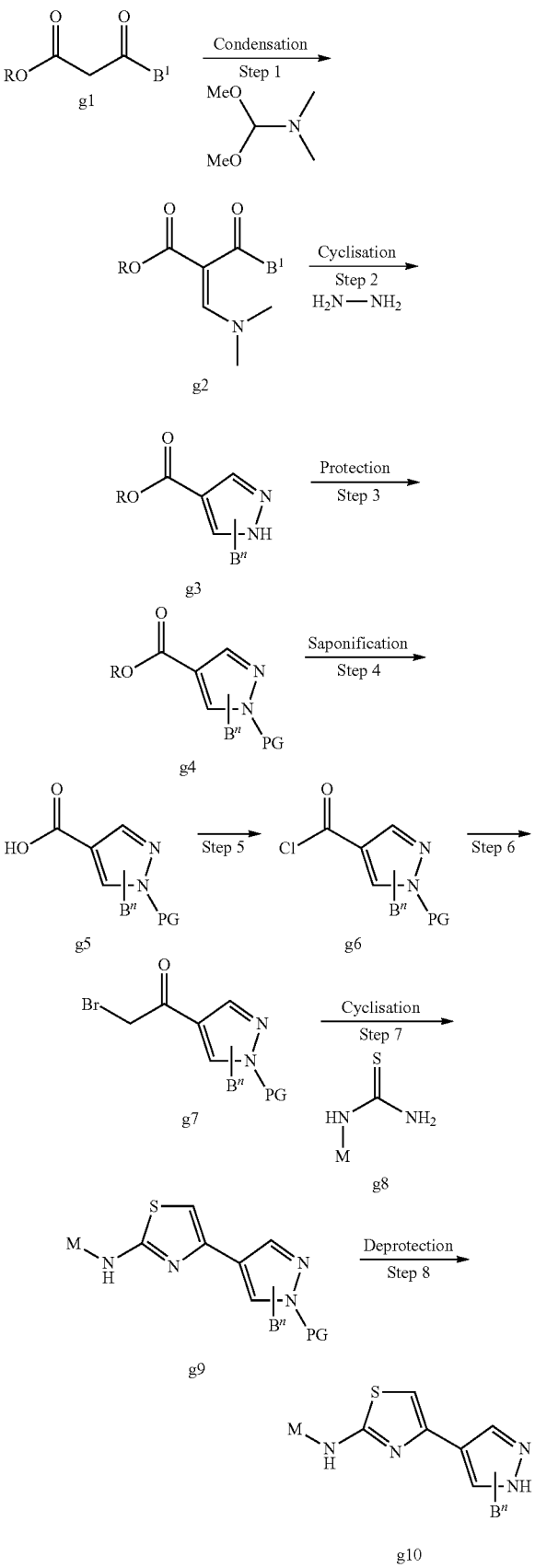

Scheme 1

In one embodiment of the present invention, the compounds of Formula (I) may be prepared according to the synthetic sequences illustrated in Scheme 2. Compound g5 may be converted into Weinreb amide g11 which undergoes addition of Grignard reagent to yield ketone g12. Subsequently ketone g12 can be transformed into bromoketone g13 in presence of $CuBr_2$. Then the cyclization reaction may be performed between bromoketone g13 and thiourea g8 to yield the aminothiazole g14. Finally, g14 can be deprotected under classical conditions.

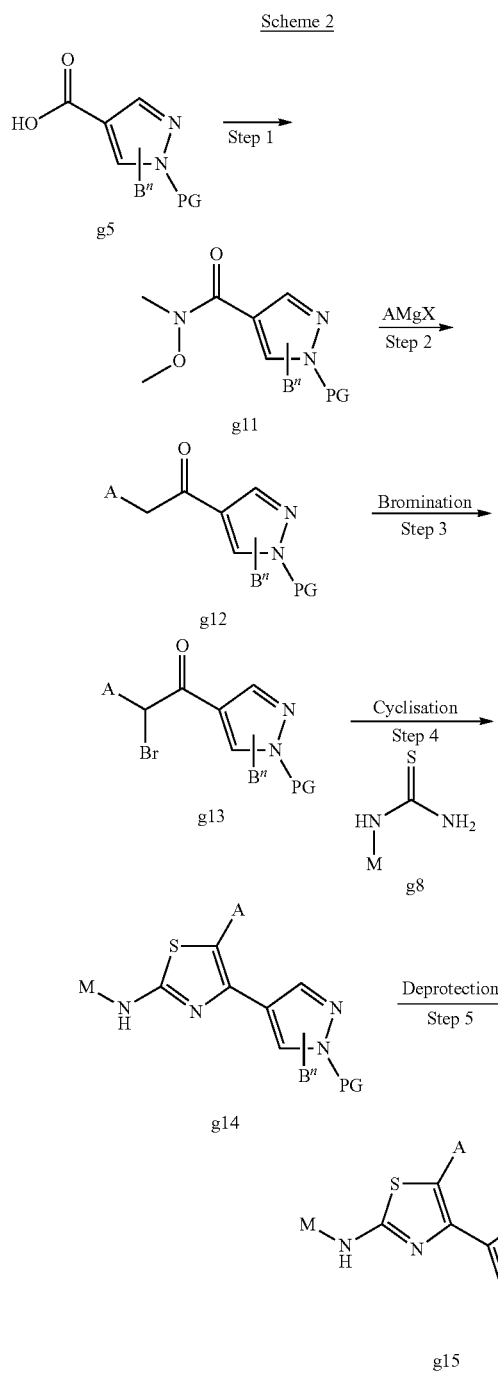

In one embodiment of the present invention, the compounds of Formula (I) may be prepared according to the synthetic sequences illustrated in Scheme 3. Cyclization may be performed between bromoketone g13 and thiourea g16. The resulting aminothiazole g17 can be coupled to MX via Buchwald coupling followed finally by deprotection under classical conditions to yield g15.

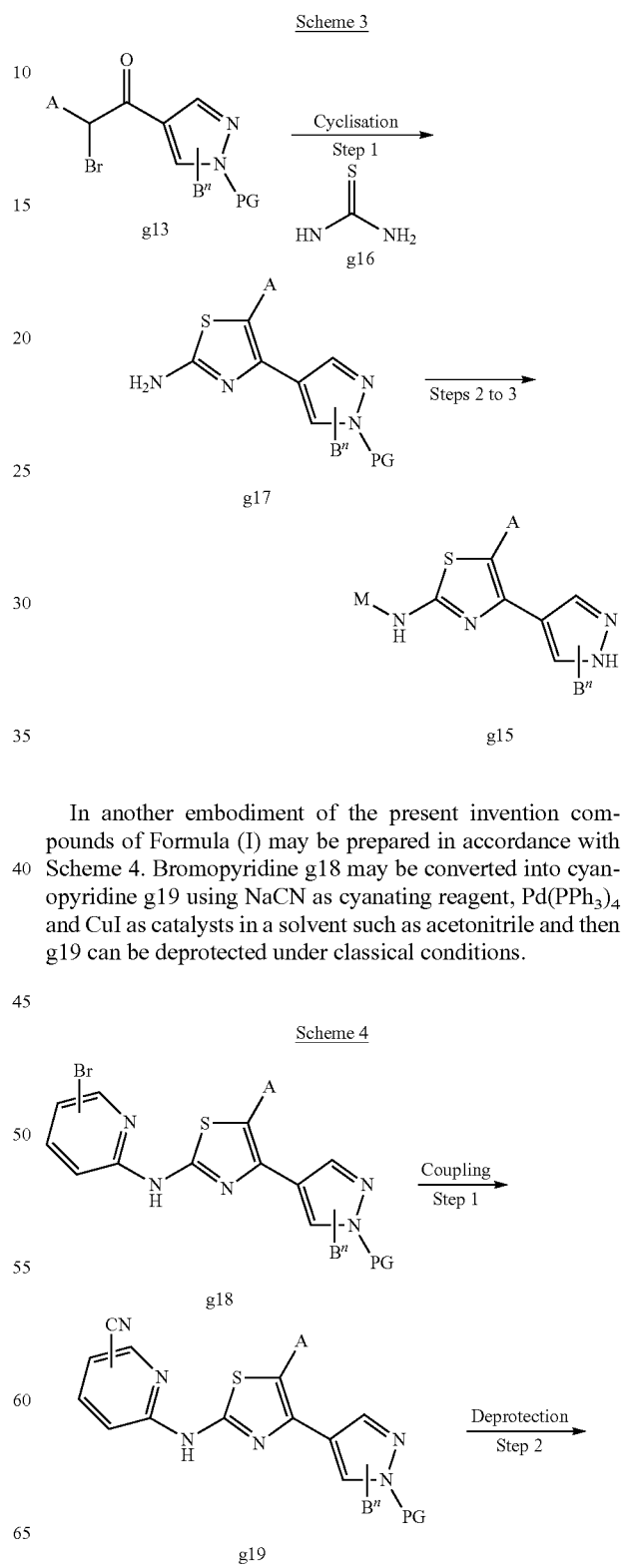

In another embodiment of the present invention compounds of Formula (I) may be prepared in accordance with Scheme 4. Bromopyridine g18 may be converted into cyanopyridine g19 using NaCN as cyanating reagent, $Pd(PPh_3)_4$ and CuI as catalysts in a solvent such as acetonitrile and then g19 can be deprotected under classical conditions.

Scheme 6

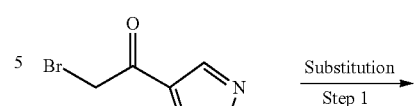
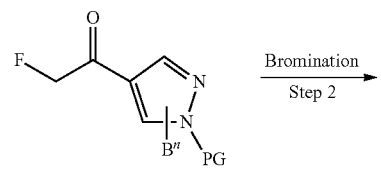
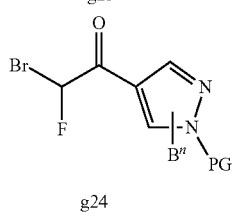

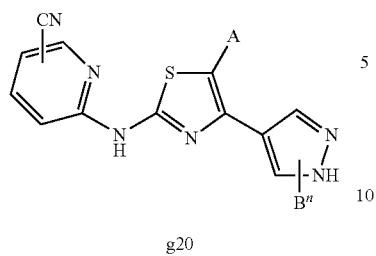

g20

In another embodiment of the present invention compounds of Formula (I) may be prepared in accordance with Scheme 5. Thiazole ring in compound g9 in the presence of N-bromosuccinimide can be substituted by bromide using standard conditions. Then compound g21 can be substituted by primary or secondary amine in DMF under microwave conditions and can finally be deprotected using classical conditions well known for people skilled in the art to yield g22.

Scheme 5

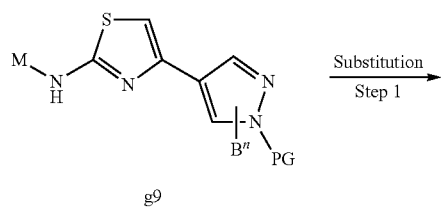

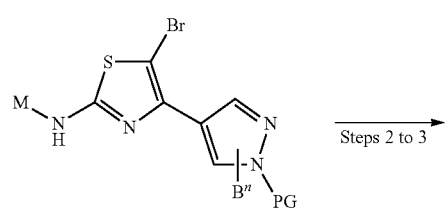

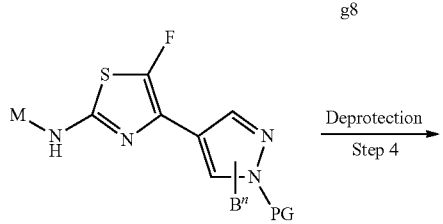

g26

In another embodiment of the present invention compounds of Formula (I) may be prepared in accordance with Scheme 7. Thiazole ring in compound g9 can be substituted by fluoride using Selectfluor or by chlorine using NCS to yield g27. Then compound g28 can be obtained after deprotection of g27 in the presence of TFA using thermic or microwave conditions.

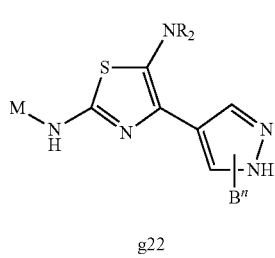

g22

In another embodiment of the present invention compounds of Formula (I) may be prepared in accordance with Scheme 6. Bromoketone g7 can be converted into fluoroketone g23 using KF as fluorinating reagent in the presence of crown ether (18-crown-6) in a solvent such as acetonitrile. Then g23 can be transformed into bromoketone g24 in the presence of $CuBr_2$. Then the cyclization reaction may be performed between bromoketone g24 and thiourea g8 to yield the aminothiazole g25. Finally, g25 can be deprotected under classical conditions well known for people skilled in the art.

Scheme 7

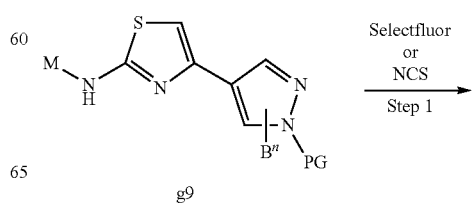

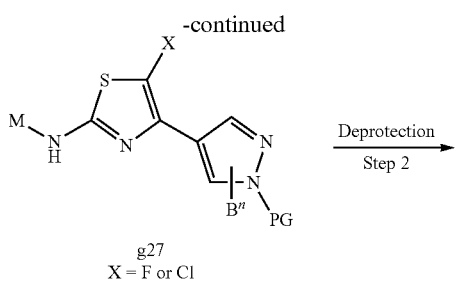

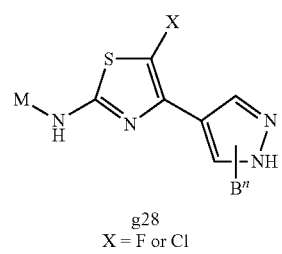

In another embodiment of the present invention compounds of Formula (I) may be prepared in accordance with Scheme 8. Methyl alcohol can be introduced on the thiazole ring from compound g10 using formaldehyde in the presence of a base such as $Et_3N$ under microwaved conditions as described in WO2007/031440A2. Alcohol g29 in the presence first of $PBr_3$, can then be converted into compound g30 by addition of either an alcohol or an amine.

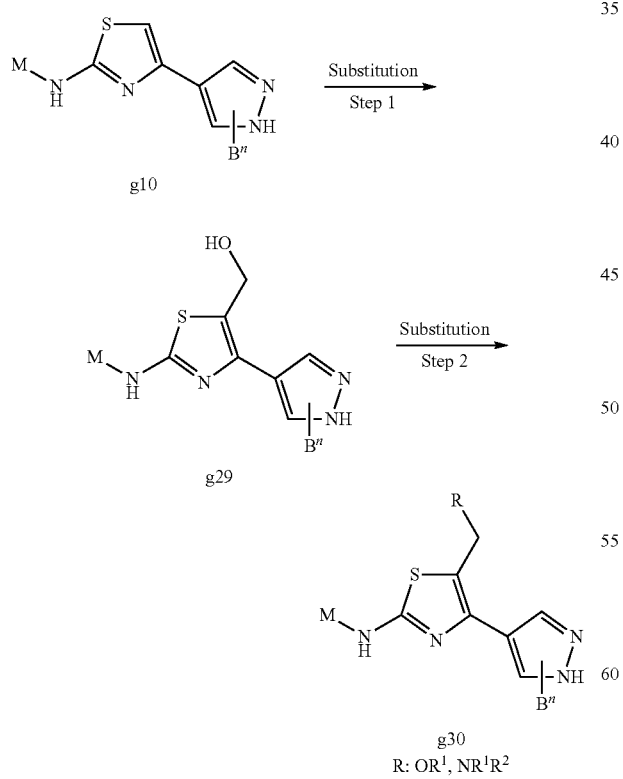

In another embodiment of the present invention compounds of Formula (I) may be prepared in accordance with Scheme 9. After protection with p-methoxybenzyl using standard conditions, pyrazole g32 undergoes coupling with (Z)-3,3,3-trifluoro-1-methoxyprop-1-ene in the presence of $Pd(OAc)_2$ and silver carbonate. The subsequent ketone g33 in the presence of thiourea g8 may be cyclized into thiazole g34. Then compound g35 can be obtained after deprotection of g34 in the presence of TFA using thermic or microwave conditions.

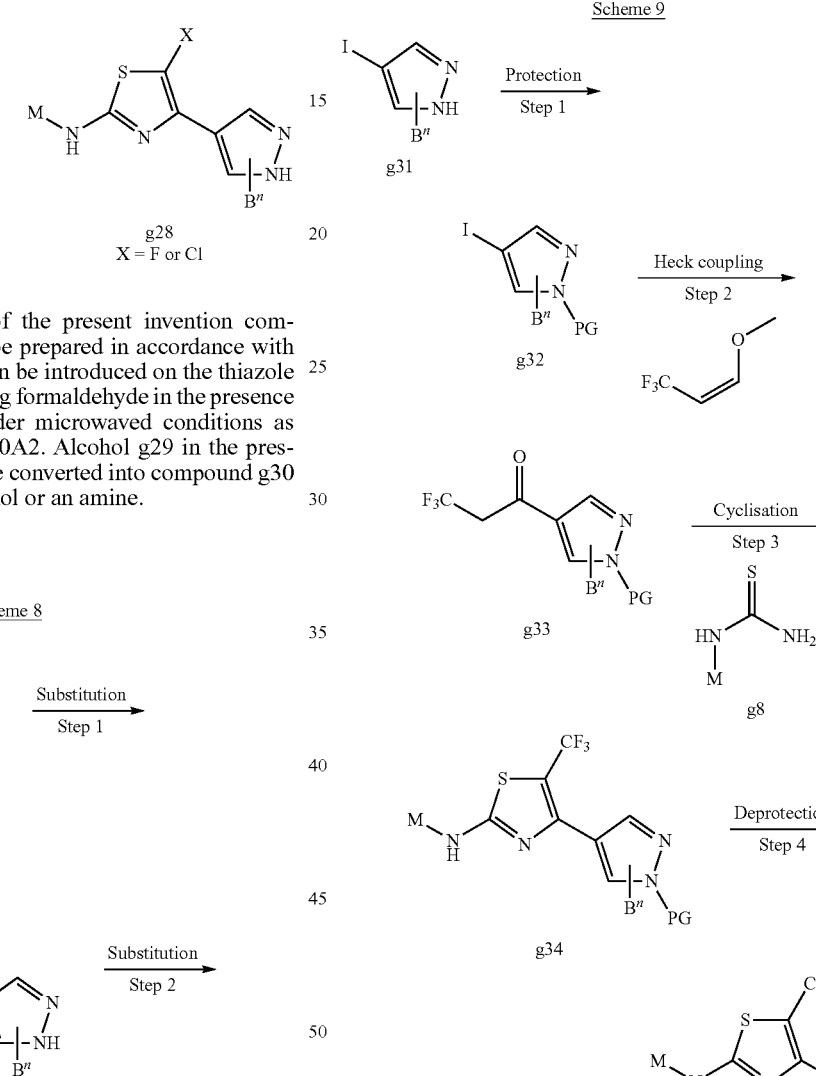

In one embodiment of the present invention, the compounds of Formula (I) may be prepared according to Scheme 10. Functionalised pyrazole g36 can be obtained from deprotonation of pyrazole g4 using LDA as a base in THF at −78° C. followed by the addition of the corresponding electrophile (N-fluoro-N-(phenylsulfonyl)benzenesulfonamide, hexachloroethane, tetrachlorodibromoethane or iodine). g36 can then be used in the Schemes described above in order to synthesize compounds of Formula (I).

Scheme 10

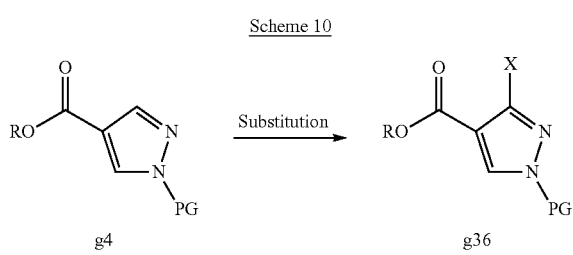

X = F, Cl, Br, I, SO$_2$Ph

In one embodiment of the present invention, the compounds of Formula (I) may be prepared according to the synthetic sequences illustrated in Scheme 11. Iodoropyrazole g37 may undergo Suzuki coupling using boronic ester or boronic acid derivative, Pd(dppf)Cl$_2$ as catalyst and DIPEA as base in a solvent such as a mixture of dioxane and water. g38 can subsequently be used in the Schemes described above in order to synthesize compounds of Formula (I).

Scheme 11

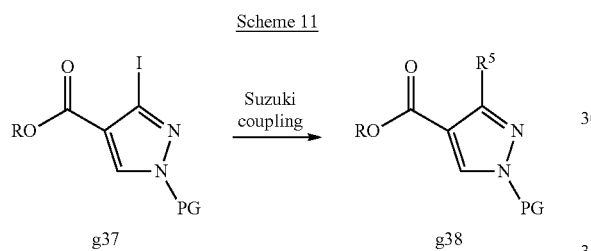

In one embodiment of the present invention, the compounds of Formula (I) may be prepared according to the synthetic sequences illustrated in Scheme 12. Bromoropyrazole g39 may undergo Suzuki coupling using boronic ester or boronic acid derivative, Pd(PPh$_3$)$_4$ as catalyst and a saturated solution of NaHCO$_3$ as base in a solvent such as dioxane. Then compound g41 can be obtained after deprotection of g40 in the presence of TFA using thermic or microwave conditions.

Scheme 12

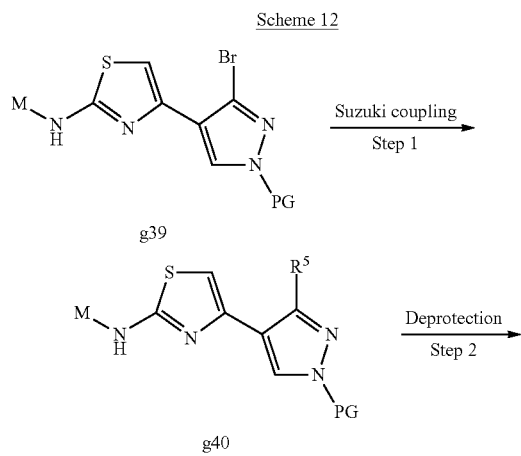

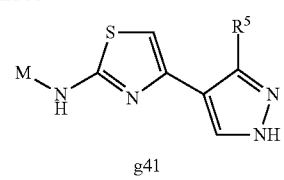

In one embodiment of the present invention, the compounds of Formula (I) may be prepared according to the synthetic sequences illustrated in Scheme 13. Chloropyrazole g42 may be converted into cyanopyrazole g43 using KCN as cyanating reagent, Pd(PPh$_3$)$_4$ and CuI as catalysts in a solvent such as acetonitrile and then g43 can be deprotected under classical conditions.

Scheme 13

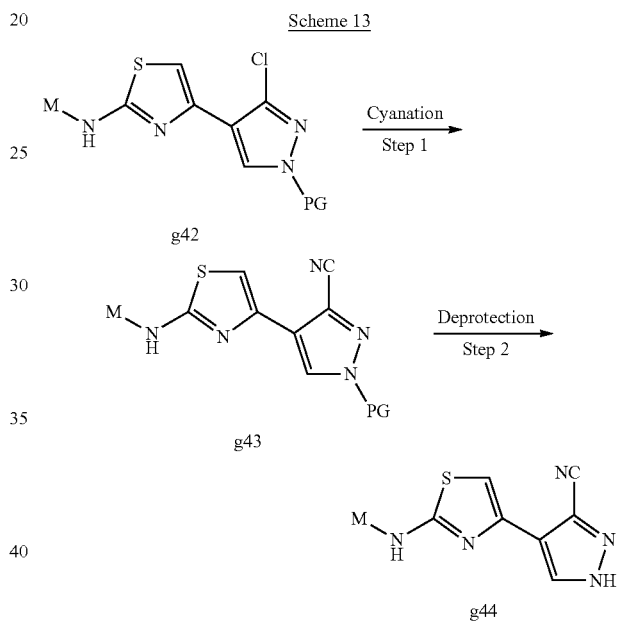

In one embodiment of the present invention, the compounds of Formula (I) may be prepared according to the synthetic sequences illustrated in Scheme 14.

Functionalised pyrazole g46 can be obtained from deprotonation of pyrazole g45 using LDA as a base in THF at −78° C. followed by the addition of hexachloroethane. The subsequent chloropyrazole g46 may be substituted by primary or secondary amine into aminopyrazole g47 which can subsequently be used in the Schemes described above in order to synthesize compounds of Formula (I).

Scheme 14

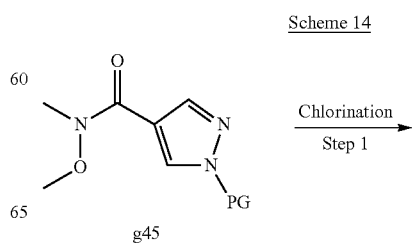

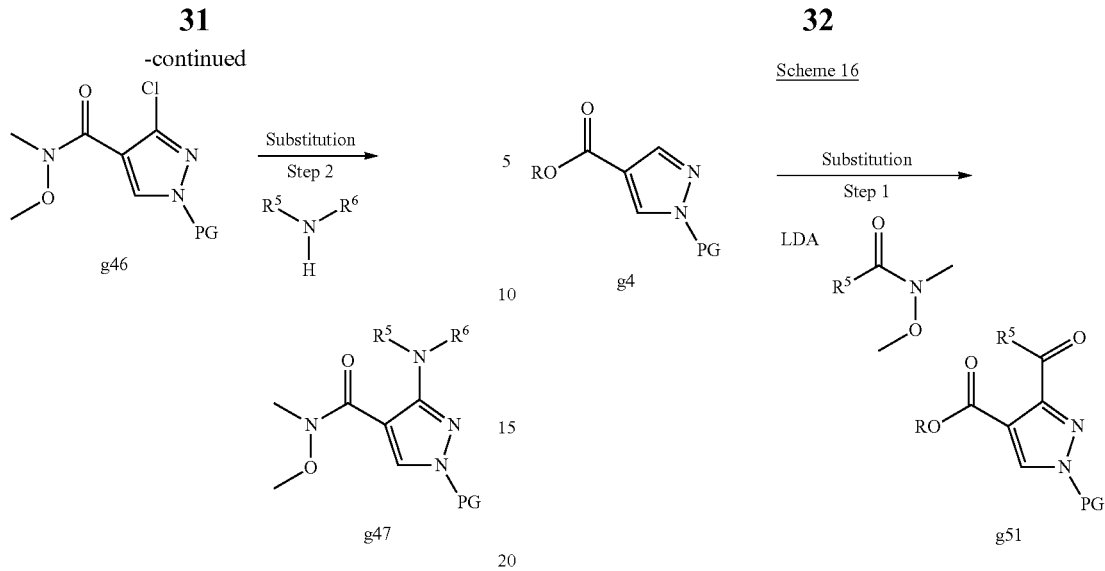

In one embodiment of the present invention, the compounds of Formula (I) may be prepared according to the synthetic sequences illustrated in Scheme 15. Pyrazole g48 can be protected by p-methoxybenzyl using standard conditions. The primary amine g49 may be converted into tertiary amine g50 using reductive amination reaction condition such as Eschweiler Clarke conditions. g50 can then be used in the Schemes described above in order to synthesize compounds of Formula (I).

In another embodiment of the present invention compounds of Formula (I) may be prepared in accordance with Scheme 17. Aldehyde can be introduced on the pyrazole ring from compound g4 using DMF in the presence of LDA. Aldehyde g52 may undergo Wittig reaction using (methoxymethyl)triphenylphosphonium chloride and a base such as KOtBu. Then enol ether g53 could be reduced into g54 using the H-Cube®. 54 can then be used in the Schemes described above in order to synthesize compounds of Formula (I).

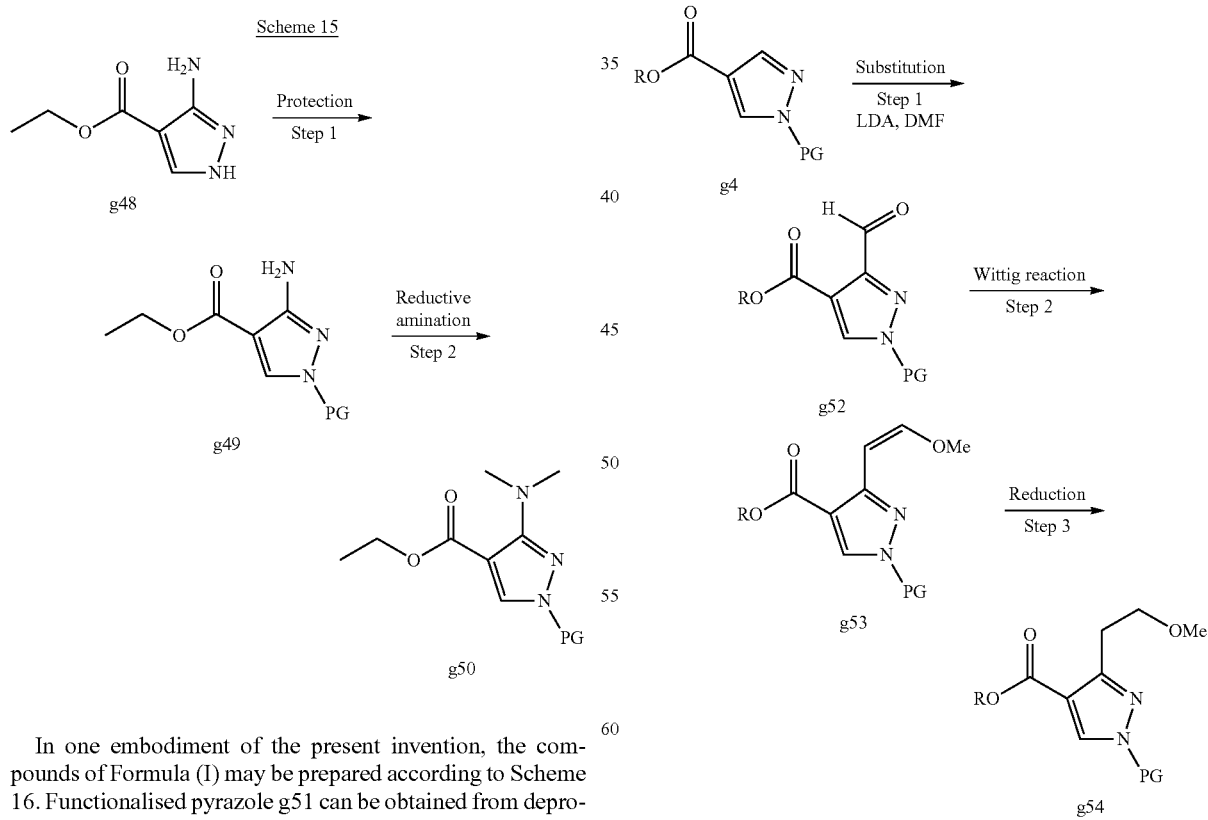

In one embodiment of the present invention, the compounds of Formula (I) may be prepared according to Scheme 16. Functionalised pyrazole g51 can be obtained from deprotonation of pyrazole g4 using LDA as a base in THF at −78° C. followed by the addition of Weinreb amine. g51 can subsequently be used in the Schemes described above in order to synthesize compounds of Formula (I).

In one embodiment of the present invention compounds of Formula (I) may be prepared according to Scheme 18. g55 may be substituted by bromoester in the presence of a base such as K$_2$CO$_3$ and in a solvent such as DMSO. Ester g56 can be converted into amide g57 by using classical conditions well known for people skilled in the art.

may be sulfonylated by sulfonyl chloride in the presence of a base such as Et$_3$N to yield pyrazole g59.

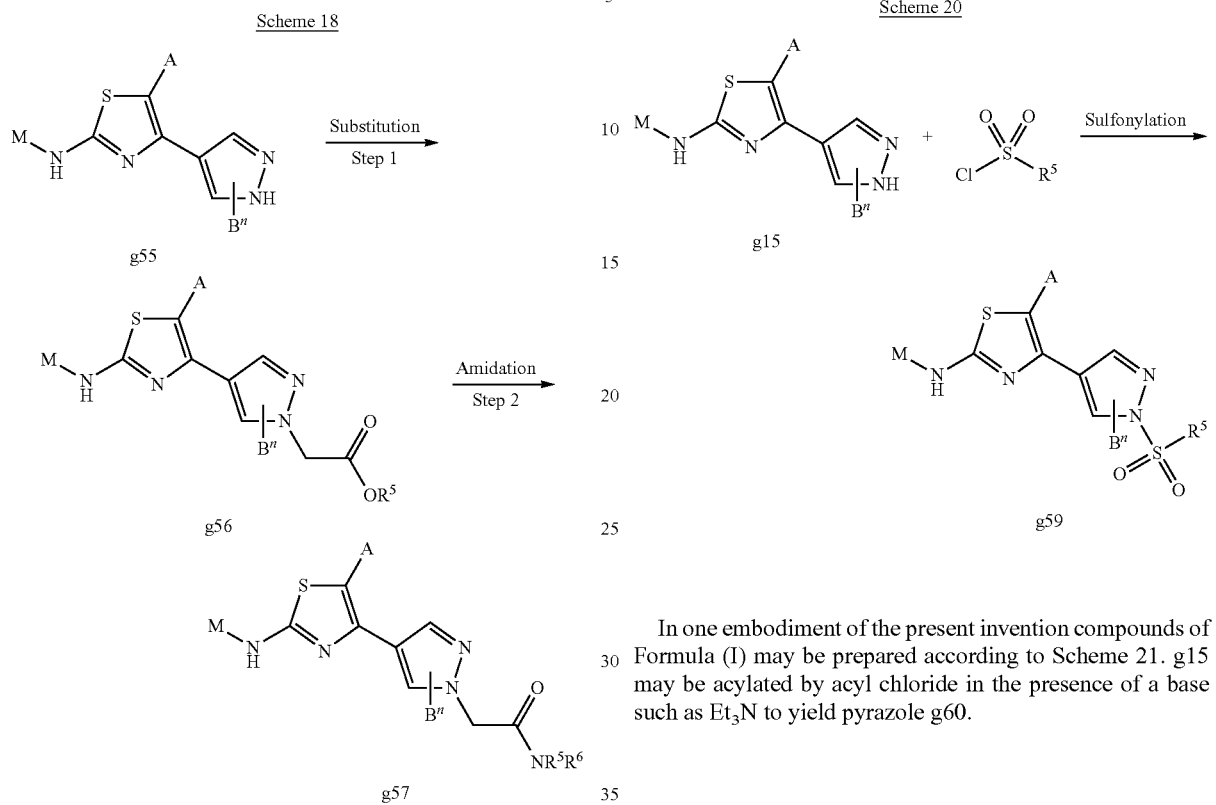

In one embodiment of the present invention compounds of Formula (I) may be prepared according to Scheme 19. g15 may be converted into urea g58 either by treatment with potassium cyanate as described in Yang et al., (2004) J. Med. Chem., 47 (6):1547-1552 or by treatment with the corresponding carbamic chloride using classical conditions well known for people skilled in the art.

In one embodiment of the present invention compounds of Formula (I) may be prepared according to Scheme 20. g15

In one embodiment of the present invention compounds of Formula (I) may be prepared according to Scheme 21. g15 may be acylated by acyl chloride in the presence of a base such as Et$_3$N to yield pyrazole g60.

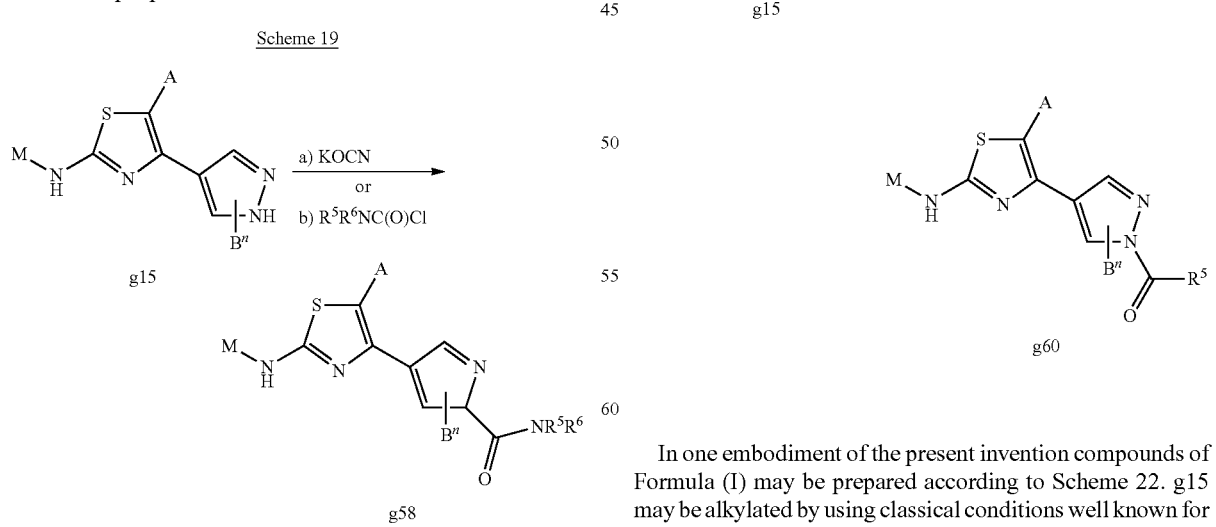

In one embodiment of the present invention compounds of Formula (I) may be prepared according to Scheme 22. g15 may be alkylated by using classical conditions well known for people skilled in the art to yield difunctionalised compound g61. The tertiary amine g61 can be selectively cleaved into secondary amine g62 using a 1N solution of HCl.

Scheme 22

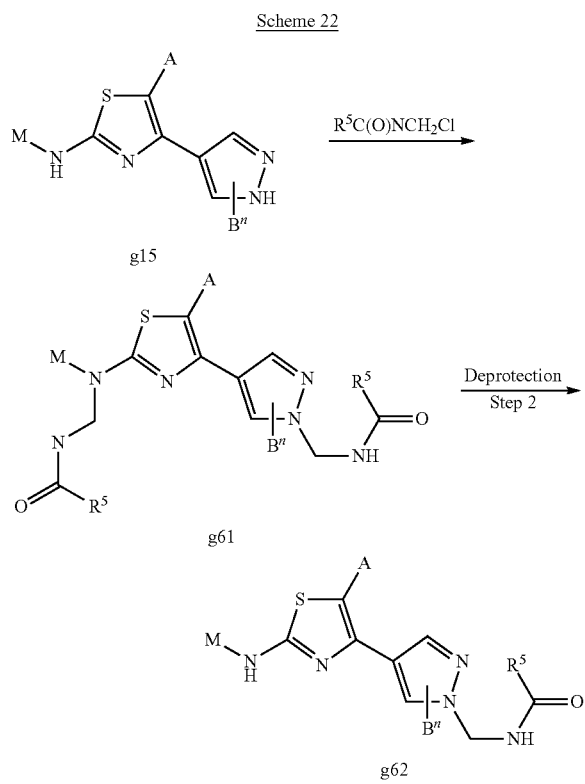

EXPERIMENTAL

Unless otherwise noted, all starting materials were obtained from commercial suppliers and used without further purification.

Specifically, the following abbreviations may be used in the examples and throughout the specification.

| | |
|---|---|
| AcOEt (Ethyl acetate) | mmol (Millimoles) |
| AcOH (Acetic acid) | M.p. (Melting point) |
| $CuBr_2$ (Copper (II) bromide) | $NH_3$ (Ammonia) |
| CuI (Copper (I) iodide) | $NH_4Cl$ (Ammonium chloride) |
| DCM (Dichloromethane) | NMP (N-Methylpyrrolidone) |
| DMF (Dimethylformamide) | NaCl (Sodium chloride) |
| EtOH (Ethanol) | NaCN (Sodium cyanide) |
| $Et_2O$ (Diethyl ether) | $NaHCO_3$ (Sodium hydrogenocarbonate) |
| $Et_3N$ (Triethyl amine) | NaOH (Sodium hydroxide) |
| HBr (Hydrobromic acid) | $Na_2CO_3$ (Sodium carbonate) |
| HCl (Hydrochloric acid) | $Na_2SO_4$ (Sodium sulphate) |
| KCN (Potassium cyanide) | $PBr_3$ (Phosphorous tribromide) |
| KF (Potassium fluoride) | $PPh_3$ (Triphenylphosphine) |
| $K_2CO_3$ (Potassium carbonate) | $Pd(dppf)Cl_2$ (1,1'-bis(diphenylphosphino)ferrocenepalladium(II) chloride) |
| LCMS (Liquid Chromatography Mass Spectrum) | $Pd(OAc)_2$ (Palladium(II)acetate) |
| LDA (Lithium diisopropylamide) | $Pd(PPh_3)_4$ (Tetrakis(triphenylphosphine)palladium(0)) |
| LiOH (Lithium hydroxide) | RT (Retention Time) |
| M (Molar) | Selectfluor (1-Chloromethyl-4-fluoro-1,4-diazoniabicyclo[2.2.2]octane bis {tetrafluoroborate}) |
| MeOH (Methanol) | TFA (Trifluoroacetic acid) |
| mg (Milligrams) | THF (Tetrahydrofuran) |
| $MgSO_4$ (Magnesium sulphate) | UPLC-MS (Ultra Performance Liquid Chromatography Mass Spectrum) |
| μL (Microliters) | Xantphos (4,5-Bis(diphenylphosphino)-9,9-dimethylxanthene) |
| mL (Milliliters) | |

All references to brine refer to a saturated aqueous solution of NaCl. Unless otherwise indicated, all temperatures are expressed in ° C. (degrees Centigrade). All reactions are conducted not under an inert atmosphere at room temperature unless otherwise noted.

Most of the reaction were monitored by thin-layer chromatography on 0.25 mm Merck silica gel plates (60F-254), visualized with UV light. Flash column chromatography was performed on prepacked silica gel cartridges (15-40 μM, Merck).

Melting point determination was performed on a Buchi B-540 apparatus.

EXAMPLES

Example 1

4-(3-Isobutyl-1H-pyrazol-4-yl)-N-(pyridin-2-yl)thiazol-2-amine (Final Compound 1.7)

Ethyl 2-((dimethylamino)methylene)-5-methyl-3-oxohexanoate

According to Scheme 1 Step 1: A solution of ethyl 5-methyl-3-oxohexanoate (11.6 mmol, 2.00 g) and of 1,1-dimethoxy-N,N-dimethylmethanamine (11.6 mmole, 1.54 mL) in DMF (10 mL) was microwaved for 30 minutes at 120° C. After evaporation of the solvent, 2.64 g (11.6 mmol) of ethyl 2-((dimethylamino)methylene)-5-methyl-3-oxohexanoate as an orange oil were obtained and used without further purification.

Ethyl 3-isobutyl-1H-pyrazole-4-carboxylate

According to Scheme 1 Step 2: A solution of ethyl 2-((dimethylamino)methylene)-5-methyl-3-oxohexanoate (11.6 mmol, 2.64 g) and hydrazine (11.6 mmol, 1.47 mL) in EtOH (10 mL) was stirred for 1 hour at room temperature. After evaporation of the solvent, the resulting crude product was purified by flash chromatography over silica gel using cyclohexane/AcOEt (80:20) as eluent to yield ethyl 3-isobutyl-1H-pyrazole-4-carboxylate (8.66 mmol, 1.70 g, 75%) as a yellow oil.
UPLC-MS: RT=0.82 min; MS m/z ES$^+$=197.

Ethyl 1-(4-methoxybenzyl)-5-isobutyl-1H-pyrazole-4-carboxylate and ethyl 1-(4-methoxybenzyl)-3-isobutyl-1H-pyrazole-4-carboxylate According to Scheme 1 Step 3: 1-(Chloromethyl)-4-methoxybenzene (9.53 mmol, 1.29 mL) was added to a suspension of ethyl 3-isobutyl-1H-pyrazole-4-carboxylate (8.66 mmol, 1.70 g) and K$_2$CO$_3$ (26.0 mmol, 3.59 g) in acetone (30 mL) and then the reaction mixture was heated at 60° C. overnight. After evaporation of the solvent, water was added and the aqueous phase was extracted with DCM. The organic phase was dried over Na$_2$SO$_4$, was filtered and was concentrated under reduced pressure. The crude product was purified by flash chromatography over silica gel using cyclohexane/AcOEt (90:10) as eluent to afford a mixture of ethyl 1-(4-methoxybenzyl)-5-isobutyl-1H-pyrazole-4-carboxylate and of ethyl 1-(4-methoxybenzyl)-3-isobutyl-1H-pyrazole-4-carboxylate (3.16 mmol, 1.00 g, 37%) as a yellow oil.
UPLC-MS: RT=1.16 min; MS m/z ES$^+$=317.

1-(4-Methoxybenzyl)-3-isobutyl-1H-pyrazole-4-carboxylic acid and 1-(4-methoxybenzyl)-5-isobutyl-1H-pyrazole-4-carboxylic acid According to Scheme 1 Step 4: LiOH (9.48 mmol, 405 mg) was added to a solution of a mixture of ethyl 1-(4-methoxybenzyl)-5-isobutyl-1H-pyrazole-4-carboxylate and of ethyl 1-(4-methoxybenzyl)-3-isobutyl-1H-pyrazole-4-carboxylate (3.16 mmol, 1.00 g) in water/MeOH (1:1, 10 mL) and the reaction mixture was heated at 80° C. for 3 hours. After evaporation of the solvent, HCl 2 M was added and the aqueous phase was extracted with DCM. The organic phase was washed with brine, was dried over Na$_2$SO$_4$, was filtered and was concentrated under reduced pressure to yield a mixture of 1-(4-methoxybenzyl)-3-isobutyl-1H-pyrazole-4-carboxylic acid and of 1-(4-methoxybenzyl)-5-isobutyl-1H-pyrazole-4-carboxylic acid (3.16 mmol, 0.91 g, 100%) as a white solid. The crude product was used without purification.

1-(4-Methoxybenzyl)-3-isobutyl-1H-pyrazole-4-carbonyl chloride and of 1-(4-methoxybenzyl)-5-isobutyl-1H-pyrazole-4-carbonyl chloride According to Scheme 1 Step 5: A solution of a mixture of 1-(4-methoxybenzyl)-3-isobutyl-1H-pyrazole-4-carboxylic acid and of 1-(4-methoxybenzyl)-5-isobutyl-1H-pyrazole-4-carboxylic acid (3.16 mmol, 911 mg), thionyl chloride (9.48 mmol, 0.69 mL) and drops of DMF in DCM (15 mL) was stirred for 1 hour at room temperature. Thionyl chloride (13.7 mmol, 1.00 mL) was added and the reaction mixture was stirred at room temperature for 1 hour. After evaporation of the solvent, the crude residue was treated with toluene and was coevaporated to dryness to yield a mixture of 1-(4-methoxybenzyl)-3-isobutyl-1H-pyrazole-4-carbonyl chloride and of 1-(4-methoxybenzyl)-5-isobutyl-1H-pyrazole-4-carbonyl chloride (3.16 mmol, 969 mg). The crude product was used without purification.

1-(1-(4-Methoxybenzyl)-3-isobutyl-1H-pyrazol-4-yl)-2-bromoethanone and 1-(1-(4-methoxybenzyl)-5-isobutyl-1H-pyrazol-4-yl)-2-bromoethanone According to Scheme 1 Step 6: A solution of TMSdiazomethane (6.95 mmol, 3.47 mL) was added to a solution of a mixture of 1-(4-methoxybenzyl)-3-isobutyl-1H-pyrazole-4-carbonyl chloride and of 1-(4-methoxybenzyl)-5-isobutyl-1H-pyrazole-4-carbonyl chloride (3.16 mmol, 969 mg) in acetonitrile (6 mL) at 0° C. The reaction mixture was stirred at room temperature overnight. HBr (11.0 mmol, 1.24 mL, 48%) was added at 0° C. to the reaction mixture. The reaction mixture was stirred at room temperature overnight. After evaporation of the solvent, the crude product was purified by flash chromatography over silica gel using cyclohexane/AcOEt (90:10) as eluent to yield after evaporation a mixture of 1-(1-(4-methoxybenzyl)-3-isobutyl-1H-pyrazol-4-yl)-2-bromoethanone and of 1-(1-(4-methoxybenzyl)-5-isobutyl-1H-pyrazol-4-yl)-2-bromoethanone (0.55 mmol, 200 mg, 17%) as a yellow oil.
UPLC-MS: RT=1.11 min; MS m/z ES$^+$=366.

N-(4-(1-(4-Methoxybenzyl)-3-isobutyl-1H-pyrazol-4-yl)thiazol-2-yl)pyridin-2-amine and N-(4-(1-(4-methoxybenzyl)-5-isobutyl-1H-pyrazol-4-yl)thiazol-2-yl)pyridin-2-amine According to Scheme 1 Step 7: A solution of a mixture of 1-(1-(4-methoxybenzyl)-3-isobutyl-1H-pyrazol-4-yl)-2-bromoethanone and of 1-(1-(4-methoxybenzyl)-5-isobutyl-1H-pyrazol-4-yl)-2-bromoethanone (0.55 mmol, 200 mg) and of 1-(pyridin-2-yl)thiourea (0.55 mmol, 84 mg) in EtOH (15 mL) was stirred under reflux for 2 hours. After evaporation of the solvent, the crude residue was purified by flash chromatography over silica gel using cyclohexane/AcOEt (70:30) as eluent to yield a mixture of N-(4-(1-(4-methoxybenzyl)-3-isobutyl-1H-pyrazol-4-yl)thiazol-2-yl)pyridin-2-amine and of N-(4-(1-(4-methoxybenzyl)-5-isobutyl-1H-pyrazol-4-yl)thiazol-2-yl)pyridin-2-amine (0.11 mmol, 48 mg, 21%) as a yellow oil.
UPLC-MS: RT=1.13 min; MS m/z ES$^+$=420.

4-(3-Isobutyl-1H-pyrazol-4-yl)-N-(pyridin-2-yl)thiazol-2-amine

According to Scheme 1 Step 8: A solution of a mixture of N-(4-(1-(4-methoxybenzyl)-3-isobutyl-1H-pyrazol-4-yl)thiazol-2-yl)pyridin-2-amine and of N-(4-(1-(4-methoxybenzyl)-5-isobutyl-1H-pyrazol-4-yl)thiazol-2-yl)pyridin-2-amine (0.11 mmol, 48 mg) in TFA (1.5 mL) was microwaved for 5 minutes at 140° C. The crude residue was neutralized with a saturated solution of Na$_2$CO$_3$ and the aqueous phase was extracted with DCM. The organic phase was dried over Na$_2$SO$_4$, was filtered and was concentrated. The resulting orange oil was purified by flash chromatography over silica gel using DCM/MeOH (100:0 to 90:10) as eluent to yield after evaporation 4-(3-isobutyl-1H-pyrazol-4-yl)-N-(pyridin-2-yl)thiazol-2-amine (40 μmol, 12 mg, 35%) as a yellow solid.
UPLC-MS: RT=0.82 min; MS m/z ES$^+$=300.

Example 2

N-(6-Iodopyridin-2-yl)-5-methyl-4-(1H-pyrazol-4-yl)thiazol-2-amine (Final Compound 1-14)

N-Methoxy-1-(4-methoxybenzyl)-N-methyl-1H-pyrazole-4-carboxamide

According to Scheme 2 Step 1: A solution of 1-(4-methoxybenzyl)-1H-pyrazole-4-carboxylic acid (34.4 mmol, 8.00 g), oxalyl chloride (68.9 mmol, 5.92 mL) and a drop of DMF in DCM (80 mL) was stirred for 1 hour at room temperature.

After evaporation, the crude product was dissolved in DCM (30 mL) and was added at 0° C. to a solution of N,O-dimethylhydroxylamine hydrochloride (103 mmol, 6.31 g) in DCM (100 mL) followed by Et$_3$N (138 mmol, 19.2 mL). The reaction mixture was stirred for 1 hour at room temperature. The reaction was quenched with a saturated solution of Na$_2$CO$_3$ (300 mL) and the aqueous phase was extracted with DCM. The organic phase was dried over MgSO$_4$, was filtered and was concentrated to yield N-methoxy-1-(4-methoxybenzyl)-N-methyl-1H-pyrazole-4-carboxamide (33.8 mmol, 9.30 g, 98%) as a beige solid.

LC-MS: RT=1.78 min; MS m/z ES$^+$=276.

1-(1-(4-Methoxybenzyl)-1H-pyrazol-4-yl)propan-1-one

According to Scheme 2 Step 2: Ethylmagnesium bromide (3N, 37.2 mmol, 12.4 mL) was added dropwise at room temperature to a solution of N-methoxy-1-(4-methoxybenzyl)-N-methyl-1H-pyrazole-4-carboxamide (33.8 mmol, 9.30 g) in THF (80 mL) and the reaction mixture was stirred for 1 hour. Then ethylmagnesium bromide (3N, 37.2 mmol, 12.4 mL) was added and the reaction mixture was stirred for 1 hour. Finally some more ethylmagnesium bromide (3N, 74.4 mmol, 24.8 mL) was added and the reaction mixture was stirred for 1.5 hour at 50° C. The reaction was quenched with HCl (1 N, 300 mL) and the aqueous phase was extracted with DCM. The organic phase was dried over MgSO$_4$, was filtered and was concentrated to yield 1-(1-(4-methoxybenzyl)-1H-pyrazol-4-yl)propan-1-one (32.7 mmol, 8.00 g, 97%) as a yellow oil.

LC-MS: RT=2.04 min; MS m/z ES$^+$=245.

2-Bromo-1-(1-(4-methoxybenzyl)-1H-pyrazol-4-yl)propan-1-one

According to Scheme 2 Step 3: A solution of 1-(1-(4-methoxybenzyl)-1H-pyrazol-4-yl)propan-1-one (32.7 mmol, 8.00 g) and CuBr$_2$ (55.7 mmol, 12.4 g) in AcOEt (130 mL) was stirred under reflux for 2 hours. After addition of silica and evaporation, the crude residue was purified by flash chromatography over silica gel using DCM/MeOH (99:1) as eluent to yield after evaporation 2-bromo-1-(1-(4-methoxybenzyl)-1H-pyrazol-4-yl)propan-1-one (23.8 mmol, 7.70 g, 73%) as a colorless oil.

LC-MS: RT=2.39 min; MS m/z ES$^+$=324.

N-(4-(1-(4-Methoxybenzyl)-1H-pyrazol-4-yl)-5-methylthiazol-2-yl)-6-iodopyridin-2-amine hydrobromide According to Scheme 2 Step 4: A solution of 2-bromo-1-(1-(4-methoxybenzyl)-1H-pyrazol-4-yl)propan-1-one (0.36 mmol, 116 mg) and of 1-(6-iodopyridin-2-yl)thiourea (0.36 mmol, 100 mg) in acetone (1.8 mL) was stirred at 60° C. for 2 days. The precipitate formed was filtered and was washed with Et$_2$O to yield N-(4-(1-(4-methoxybenzyl)-1H-pyrazol-4-yl)-5-methylthiazol-2-yl)-6-iodopyridin-2-amine hydrobromide (0.23 mmol, 136 mg, 65%) as a white solid.

UPLC-MS: RT=1.26 min; MS m/z ES$^+$=504.

N-(6-Iodopyridin-2-yl)-5-methyl-4-(1H-pyrazol-4-yl)thiazol-2-amine

According to Scheme 2 Step 5: A solution of N-(4-(1-(4-methoxybenzyl)-1H-pyrazol-4-yl)-5-methylthiazol-2-yl)-6-iodopyridin-2-amine (0.27 mmol, 136 mg) in TFA (1.4 mL) was microwaved for 5 minutes at 140° C. The reaction mixture was neutralized with a saturated solution of Na$_2$CO$_3$ and the aqueous phase was extracted with DCM. The organic phase was dried over MgSO$_4$, was filtered and was concentrated. The resulting crude product was purified by flash chromatography over silica gel using DCM/MeOH (100:0 to 90:10) as eluent to yield N-(6-iodopyridin-2-yl)-5-methyl-4-(1H-pyrazol-4-yl)thiazol-2-amine (91 μmol, 34 mg, 34%) as a white solid.

M.p.: >260° C.;
UPLC-MS: RT=1.02 min; MS m/z ES$^+$=384.

Example 3

N-(4-Fluoropyridin-2-yl)-5-methyl-4-(1H-pyrazol-4-yl)thiazol-2-amine (Final Compound 1-19)

4-(1-(4-Methoxybenzyl)-1H-pyrazol-4-yl)-5-methylthiazol-2-amine

According to Scheme 3 Step 1: A solution of 2-bromo-1-(1-(4-methoxybenzyl)-1H-pyrazol-4-yl)propan-1-one (13.9 mmol, 4.50 g, described in Example 2) and of thiourea (13.9 mmol, 1.06 g) in acetone (30 mL) was stirred at 60° C. for 3 hours. After evaporation of the solvent, the crude residue was dissolved in DCM. The organic phase was washed with a saturated solution of NaHCO$_3$, water and brine, was dried over Na$_2$SO$_4$, was filtered and was concentrated. The resulting crude product was purified by flash chromatography over silica gel using DCM/AcOEt (80:20) as eluent to yield after evaporation 4-(1-(4-methoxybenzyl)-1H-pyrazol-4-yl)-5-methylthiazol-2-amine (13.3 mmol, 4.00 g, 96%) as a yellow solid.

UPLC-MS: RT=0.56 min; MS m/z ES$^+$=301.

N-(4-(1-(4-Methoxybenzyl)-1H-pyrazol-4-yl)-5-methylthiazol-2-yl)-4-fluoropyridin-2-amine According to Scheme 3 Step 2: A solution of 4-(1-(4-methoxybenzyl)-1H-pyrazol-4-yl)-5-methylthiazol-2-amine (0.47 mmol, 140 mg), 2-chloro-4-fluoropyridine (0.47 mmol, 61 mg), Xantphos (70 μmol, 40.5 mg), Pd(OAc)$_2$ (46 μmol, 10.5 mg) and cesium carbonate (0.93 mmol, 304 mg) in dioxane (6.5 mL) was microwaved at 135° C. for 2 hours under nitrogen. After evaporation of the solvent, the resulting crude product was purified by flash chromatography over silica gel using cyclohexane/AcOEt (80:20) as eluent to afford N-(4-(1-(4-methoxybenzyl)-1H-pyrazol-4-yl)-5-methylthiazol-2-yl)-4-fluoropyridin-2-amine (0.33 mmol, 132 mg, 71%).

UPLC-MS: RT=1.15 min; MS m/z ES$^+$=396.

N-(4-Fluoropyridin-2-yl)-5-methyl-4-(1H-pyrazol-4-yl)thiazol-2-amine

According to Scheme 3 Step 3: A solution of N-(4-(1-(4-methoxybenzyl)-1H-pyrazol-4-yl)-5-methylthiazol-2-yl)-4-fluoropyridin-2-amine (0.33 mmol, 132 mg) in TFA (1.5 mL) was microwaved for 2 minutes at 150° C. A precipitate was formed after addition of a saturated solution of Na$_2$CO$_3$ and water. After filtration, the solid was washed with water and recrystallized in Et$_2$O to yield N-(4-fluoropyridin-2-yl)-5-methyl-4-(1H-pyrazol-4-yl)thiazol-2-amine (0.17 mmol, 47 mg, 51%) as a beige solid.

M.p.: 283° C.;
UPLC-MS: RT=0.87 min; MS m/z ES$^+$=276.

Example 4

6-(5-Methyl-4-(1H-pyrazol-4-yl)thiazol-2-ylamino) picolinonitrile (Final Compound 1-1)

*6-(4-(1-(4-Methoxybenzyl)-1H-pyrazol-4-yl)-5-methylthiazol-2-ylamino)picolinonitrile*

According to Scheme 4 Step 1: A solution of N-(4-(1-(4-methoxybenzyl)-1H-pyrazol-4-yl)-5-methylthiazol-2-yl)-6-bromopyridin-2-amine (0.94 mmol, 430 mg), NaCN (3.54 mmol, 174 mg), Pd(PPh$_3$)$_4$ (0.42 mmol, 487 mg) and CuI (0.18 mmol, 34 mg) in acetonitrile (22 mL) was microwaved at 180° C. for 6 hours under nitrogen. After evaporation of the solvent, the resulting crude product was purified by flash chromatography over silica gel using DCM/MeOH (80:20) as eluent to afford 6-(4-(1-(4-methoxybenzyl)-1H-pyrazol-4-yl)-5-methylthiazol-2-ylamino)picolinonitrile (0.69 mmol, 277 mg, 73%).

LC-MS: RT=2.59 min; MS m/z ES$^+$=403.

*6-(5-Methyl-4-(1H-pyrazol-4-yl)thiazol-2-ylamino) picolinonitrile*

According to Scheme 4 Step 2: A solution of 6-(4-(1-(4-methoxybenzyl)-1H-pyrazol-4-yl)-5-methylthiazol-2-ylamino)picolinonitrile (0.69 mmol, 277 mg) in TFA (4 mL) was microwaved for 7 minutes at 100° C. After evaporation of the solvent, the resulting residue was neutralized with a saturated solution of Na$_2$CO$_3$. The compound precipitated and after filtration, the solid was washed with water and dried. The solid was finally triturated in Et$_2$O, DCM and MeOH to yield 6-(5-methyl-4-(1H-pyrazol-4-yl)thiazol-2-ylamino)picolinonitrile (90 μmol, 25 mg, 12%) as a beige solid.

M.p.: 331° C.;
LC-MS: RT=1.90 min; MS m/z ES$^+$=283.

Example 5

5-(Piperidin-1-yl)-4-(1H-pyrazol-4-yl)-N-(pyridin-2-yl)thiazol-2-amine (Final Compound 1-4)

*N-(4-(1-(4-Methoxybenzyl)-1H-pyrazol-4-yl)-5-bromothiazol-2-yl)pyridin-2-amine*

According to Scheme 5 Step 1: A solution of N-(4-(1-(4-methoxybenzyl)-1H-pyrazol-4-yl)thiazol-2-yl)pyridin-2-amine (4.20 mmol, 1.53 g) and N-bromosuccinimide (4.40 mmol, 782 mg) in DMF (76 mL) was stirred for 1.5 hour at 50° C. The reaction mixture was diluted with a saturated solution of Na$_2$CO$_3$ and water. The precipitate formed was recovered and washed with DCM. The aqueous phase was extracted with DCM and the organic phase was washed. The organic phase was dried over MgSO$_4$, was filtered and was concentrated to yield with the addition of the precipitate N-(4-(1-(4-methoxybenzyl)-1H-pyrazol-4-yl)-5-bromothiazol-2-yl)pyridin-2-amine (4.02 mmol, 1.78 g, 96%) as a beige solid.

LC-MS: RT=2.97 min; MS m/z ES$^+$=443.

*N-(4-(1-(4-Methoxybenzyl)-1H-pyrazol-4-yl)-5-(piperidin-1-yl)thiazol-2-yl)pyridin-2-amine*

According to Scheme 5 Step 2: A solution of N-(4-(1-(4-methoxybenzyl)-1H-pyrazol-4-yl)-5-bromothiazol-2-yl)pyridin-2-amine (2.16 mmol, 1.00 g), piperidine (8.64 mmol, 0.89 mL) and Et$_3$N (12.9 mmol, 1.81 mL) in DMF (10 mL) was microwaved for 30 minutes at 150° C. The reaction mixture was diluted with AcOEt and water. The aqueous phase was extracted with AcOEt. The organic phase was dried over Na$_2$SO$_4$, was filtered and was concentrated to yield N-(4-(1-(4-methoxybenzyl)-1H-pyrazol-4-yl)-5-(piperidin-1-yl)thiazol-2-yl)pyridin-2-amine (0.58 mmol, 263 mg, 26%) as a beige solid.

UPLC-MS: RT=1.09 min; MS m/z ES$^+$=447.

*5-(Piperidin-1-yl)-4-(1H-pyrazol-4-yl)-N-(pyridin-2-yl)thiazol-2-amine*

According to Scheme 5 Step 3: A solution N-(4-(1-(4-methoxybenzyl)-1H-pyrazol-4-yl)-5-(piperidin-1-yl)thiazol-2-yl)pyridin-2-amine (0.58 mmol, 260 mg) in TFA (4 mL) was microwaved for 8 minutes at 140° C. After evaporation of the solvent, the crude residue was neutralized with a solution of NaOH (1 M). The aqueous phase was extracted with DCM. The organic phase was dried over MgSO$_4$, was filtered and was concentrated to yield 5-(piperidin-1-yl)-4-(1H-pyrazol-4-yl)-N-(pyridin-2-yl)thiazol-2-amine (0.60 mmol, 195 mg, 99%) as a pale yellow solid.

M.p.: 238° C.;
UPLC-MS: RT=0.81 min; MS m/z ES$^+$=327.

Example 6

5-Fluoro-N-(6-methylpyridin-2-yl)-4-(1H-pyrazol-4-yl)thiazol-2-amine (Final Compound 1-11)

*1-(1-(4-Methoxybenzyl)-1H-pyrazol-4-yl)-2-fluoroethanone*

According to Scheme 6 Step 1: A solution of 1-(1-(4-methoxybenzyl)-1H-pyrazol-4-yl)-2-bromoethanone (8.39 mmol, 3.00 g), KF (33.6 mmol, 1.97 g) and 18-crown-6 (4.20 mmol, 1.12 g) in acetonitrile (25 mL) was stirred under reflux for 3 hours. After the evaporation of solvent, the crude residue was dissolved in AcOEt. The organic phase was washed with water, was dried over Na$_2$SO$_4$, was filtered and was concentrated. The resulting crude product was purified by flash chromatography over silica gel using DCM/MeOH (100:0 to 95:5) as eluent to yield 1-(1-(4-methoxybenzyl)-1H-pyrazol-4-yl)-2-fluoroethanone (3.62 mmol, 900 mg, 78%) as a white solid.

UPLC-MS: RT=0.75 min; MS m/z ES$^+$=249.

*1-(1-(4-Methoxybenzyl)-1H-pyrazol-4-yl)-2-bromo-2-fluoroethanone*

According to Scheme 6 Step 2: A solution of 1-(1-(4-methoxybenzyl)-1H-pyrazol-4-yl)-2-fluoroethanone (2.20 mmol, 700 mg) and CuBr$_2$ (3.98 mmol, 890 mg) in AcOEt (20 mL) was stirred at 90° C. for 6 hours. After evaporation of the solvent, the resulting crude product was purified by flash chromatography over silica gel using DCM as eluent to yield 1-(1-(4-methoxybenzyl)-1H-pyrazol-4-yl)-2-bromo-2-fluoroethanone (23.8 mmol, 7.70 g, 73%) as a pale green oil.

UPLC-MS: RT=0.92 min; MS m/z ES$^+$=328.

*N-(4-(1-(4-Methoxybenzyl)-1H-pyrazol-4-yl)-5-fluorothiazol-2-yl)-6-methylpyridin-2-amine*

According to Scheme 6 Step 3: A solution of 1-(1-(4-methoxybenzyl)-1H-pyrazol-4-yl)-2-bromo-2-fluoroethanone (0.26 mmol, 110 mg) and of 1-(6-methylpyridin-2-yl) thiourea (0.26 mmol, 44 mg) in acetone (3 mL) was stirred at 50° C. for 5 hours. A precipitate was formed, was filtered and was washed with Et₂O to yield N-(4-(1-(4-methoxybenzyl)-1H-pyrazol-4-yl)-5-fluorothiazol-2-yl)-6-methylpyridin-2-amine (0.24 mmol, 95 mg, 92%) as a beige solid.

UPLC-MS: RT=1.23 min; MS m/z ES$^+$=396.

5-Fluoro-N-(6-methylpyridin-2-yl)-4-(1H-pyrazol-4-yl)thiazol-2-amine

According to Scheme 6 Step 4: A solution of N-(4-(1-(4-methoxybenzyl)-1H-pyrazol-4-yl)-5-fluorothiazol-2-yl)-6-methylpyridin-2-amine (0.24 mmol, 95 mg) in TFA (3 mL) was microwaved for 8 minutes at 140° C. After evaporation of the solvent, the reaction mixture was neutralized with a solution of NaOH (1 M). The aqueous phase was extracted with DCM and with AcOEt. The organic phase was dried over MgSO₄, was filtered and was concentrated. The resulting crude product was washed with Et₂O to yield 5-fluoro-N-(6-methylpyridin-2-yl)-4-(1H-pyrazol-4-yl)thiazol-2-amine (0.12 mmol, 33 mg, 50%) as a beige solid.

M.p.: 204° C.;

UPLC-MS: RT=0.94 min; MS m/z ES$^+$=276.

Example 7

5-Fluoro-N-(5-fluoropyridin-2-yl)-4-(1H-pyrazol-4-yl)thiazol-2-amine (Final Compound 1-28)

N-(4-(1-(4-Methoxybenzyl)-1H-pyrazol-4-yl)-5-fluorothiazol-2-yl)-5-fluoropyridin-2-amine According to Scheme 7 Step 1: Selectfluor (3.28 mmol, 1.16 g) was added portionwise to a solution of N-(4-(1-(4-methoxybenzyl)-1H-pyrazol-4-yl)thiazol-2-yl)-5-fluoropyridin-2-amine (2.18 mmol, 833 mg) and of 2,6-dimethylpyridine (2.18 mmol, 0.25 mL) in DMF (25 mL) at 0° C. The reaction mixture was stirred at room temperature for 12 hours. The reaction was quenched with water (70 mL). A precipitate was formed, was filtered and was dried to yield N-(4-(1-(4-methoxybenzyl)-1H-pyrazol-4-yl)-5-fluorothiazol-2-yl)-5-fluoropyridin-2-amine (1.85 mmol, 739 mg, 85%).

UPLC-MS: RT=1.16 min; MS m/z ES$^+$=400.

5-Fluoro-N-(5-fluoropyridin-2-yl)-4-(1H-pyrazol-4-yl)thiazol-2-amine

According to Scheme 7 Step 2: A solution of N-(4-(1-(4-methoxybenzyl)-1H-pyrazol-4-yl)-5-fluorothiazol-2-yl)-5-fluoropyridin-2-amine (1.85 mmol, 739 mg) in TFA (2 mL) was microwaved for 8 minutes at 120° C. The reaction mixture was neutralized with a saturated solution of Na₂CO₃ (100 mL). The aqueous phase was filtered to afford a brown solid. The resulting crude product was purified by flash chromatography over silica gel using DCM as eluent to yield 5-fluoro-N-(5-fluoropyridin-2-yl)-4-(1H-pyrazol-4-yl)thiazol-2-amine (0.21 mmol, 60 mg, 95%) as a yellow solid.

M.p.: 239° C.;

UPLC-MS: RT=0.89 min; MS m/z ES$^+$=280.

Example 8

5-(Methoxymethyl)-4-(1H-pyrazol-4-yl)-N-(pyridin-2-yl)thiazol-2-amine (Final Compound 1-18)

(2-(Pyridin-2-ylamino)-4-(1-tosyl-1H-pyrazol-4-yl)thiazol-5-yl)methanol

According to Scheme 8 Step 1: A solution of N-(4-(1-tosyl-1H-pyrazol-4-yl)thiazol-2-yl)pyridin-2-amine (0.65 mmol, 260 mg), formaldehyde (0.5 mL, 30% in water) and Et₃N (0.2 mL) in THF (0.5 mL) was microwaved for 10 minutes at 100° C. The reaction mixture was quenched with water (50 mL) and the aqueous phase was extracted with AcOEt. The organic phase was washed with a solution of NaOH (1 M), was dried over MgSO₄, was filtered and was concentrated. The resulting crude product was purified by flash chromatography over silica gel using cyclohexane/AcOEt (90:10 to 30:70) as eluent to yield after evaporation (2-(pyridin-2-ylamino)-4-(1-tosyl-1H-pyrazol-4-yl)thiazol-5-yl)methanol (0.37 mmol, 160 mg, 57%) as a beige solid.

UPLC-MS: RT=0.88 min; MS m/z ES$^+$=428.

5-(Methoxymethyl)-4-(1H-pyrazol-4-yl)-N-(pyridin-2-yl)thiazol-2-amine

According to Scheme 8 Step 2: PBr₃ (53 μmol, 14 mg) was added to a solution of (2-(pyridin-2-ylamino)-4-(1-tosyl-1H-pyrazol-4-yl)thiazol-5-yl)methanol (105 mmol, 45 mg) in DCM (1.5 mL) at 0° C. and the reaction mixture was stirred for 20 minutes at room temperature. Then MeOH (7 mL) was added and the reaction mixture was stirred at room temperature for 30 minutes. Finally a solution of NaOH (1 M, 0.84 mmol) was added and the solution was stirred for 2 hours. After evaporation of the solvent, the crude residue was dissolved in AcOEt. The organic phase was washed with a saturated solution of NaHCO₃, was dried over MgSO₄, was filtered and was concentrated. The resulting crude product was purified by flash chromatography over silica gel using DCM/MeOH (100:0 to 96:4) as eluent to yield after evaporation 5-(methoxymethyl)-4-(1H-pyrazol-4-yl)-N-(pyridin-2-yl)thiazol-2-amine (70 μmol, 20 mg, 66%) as a white solid.

UPLC-MS: RT=0.75 min; MS m/z ES$^+$=288.

Example 9

5-Chloro-4-(1H-pyrazol-4-yl)-N-(pyrimidin-2-yl)thiazol-2-amine (Final Compound 1-45)

5-Chloro-4-(1-(4-methoxybenzyl)-1H-pyrazol-4-yl)-N-(pyrimidin-2-yl)thiazol-2-amine According to Scheme 7, Step 1: To a solution of 4-(1-(4-methoxybenzyl)-1H-pyrazol-4-yl)-N-(pyrimidin-2-yl)thiazol-2-amine (0.85 mmol, 0.31 g) in DMF (1 mL) was added 1-chloropyrrolidine-2,5-dione (0.64 mmol, 85 mg). The reaction mixture was stirred for 1 hour at room temperature. The reaction was quenched with a saturated aqueous solution of Na₂CO₃ and extracted with AcOEt. The combined organic layers were dried over MgSO₄, were filtered and were evaporated under reduced pressure to afford 5-chloro-4-(1-(4-methoxybenzyl)-1H-pyrazol-4-yl)-N-(pyrimidin-2-yl)thiazol-2-amine (0.33 mmol, 130 mg, 38%) as an orange solid.

UPLC-MS: RT=1.09 min; MS m/z ES$^+$=399.

5-Chloro-4-(1H-pyrazol-4-yl)-N-(pyrimidin-2-yl) thiazol-2-amine

According to Scheme 7, Step 2: A mixture of 5-chloro-4-(1-(4-methoxybenzyl)-1H-pyrazol-4-yl)-N-(pyrimidin-2-yl) thiazol-2-amine (0.33 mmol, 130 mg) in TFA (1 mL) was stirred for 8 minutes at 120° C. under microwave activation. The reaction mixture was neutralized with a saturated aqueous solution of $Na_2CO_3$ and extracted with AcOEt. The combined organic layers were dried over $MgSO_4$, were filtered and were evaporated under reduced pressure. The crude compound was purified by flash chromatography with silica gel using DCM/MeOH (96:4) as eluent to afford 5-chloro-4-(1H-pyrazol-4-yl)-N-(pyrimidin-2-yl)thiazol-2-amine (0.26 mmol, 74 mg, 81%) as a beige solid.

UPLC-MS: RT=0.78 min; MS m/z $ES^+$=279.

Example 10

N-(4-Methylpyrimidin-2-yl)-4-(1H-pyrazol-4-yl)-5-(trifluoromethyl)thiazol-2-amine (Final Compound 1-58)

4-Iodo-1-(4-methoxybenzyl)-1H-pyrazole

According to Scheme 9 Step 1: A suspension of 4-iodo-1H-pyrazole (26.3 mmol, 5.11 g), 1-(chloromethyl)-4-methoxybenzene (29.0 mmol, 3.95 mL) and $K_2CO_3$ (39.5 mmol, 5.46 g) in acetonitrile (150 mL) was heated at 60° C. overnight. The reaction mixture was cooled to room temperature and was filtered. The filtrate was concentrated under reduced pressure. The crude product was purified by flash chromatography over silica gel using DCM as eluent to afford 4-iodo-1-(4-methoxybenzyl)-1H-pyrazole (23.2 mmol, 7.3 g, 88%) as a yellow solid.

UPLC-MS: RT=1.02 min; MS m/z $ES^+$=315.

3,3,3-Trifluoro-1-(1-(4-methoxybenzyl)-1H-pyrazol-4-yl)propan-1-one

According to Scheme 9 Step 2: A solution of 4-iodo-1-(4-methoxybenzyl)-1H-pyrazole (6.05 mmol, 1.90 g), (Z)-3,3,3-trifluoro-1-methoxyprop-1-ene (18.1 mmol, 2.29 g), silver carbonate (6.05 mmol, 1.67 g), $Pd(OAc)_2$ (0.18 mmol, 41 mg) and $PPh_3$ (0.36 mmol, 95 mg) in DMF (30 mL) was stirred at 80° C. for 2 days. After addition of HCl (1 N, 100 mL), the reaction mixture was stirred at room temperature for 2 hours. The reaction was quenched with water (100 mL) and the aqueous phase was extracted with DCM. The organic phase was dried over $MgSO_4$, was filtered and was concentrated to yield a brown solid. The resulting crude product was purified by flash chromatography over silica gel using cyclohexane/AcOEt (70:30) as eluent to yield after evaporation 3,3,3-trifluoro-1-(1-(4-methoxybenzyl)-1H-pyrazol-4-yl)propan-1-one (3.25 mmol, 970 mg, 54%) as a beige solid.

UPLC-MS: RT=0.93 min; MS m/z $ES^+$=299.

4-(1-(4-Methoxybenzyl)-1H-pyrazol-4-yl)-N-(4-methylpyrimidin-2-yl)-5-(trifluoromethyl)thiazol-2-amine According to Scheme 9 Step 3: To a solution of 1-(4-methylpyrimidin-2-yl)thiourea (0.79 mmol, 133 mg) in pyridine (1 mL) was added iodine (0.79 mmol, 200 mg). The solution was stirred at 80° C. for 15 minutes and then 3,3,3-trifluoro-1-(1-(4-methoxybenzyl)-1H-pyrazol-4-yl)propan-1-one (0.79 mmol, 235 mg) was added. The reaction mixture was stirred for 2 hours at 80° C. The solvent was removed under reduced pressure. The crude mixture was partitioned between AcOEt and a saturated aqueous solution of $Na_2CO_3$. The aqueous layer was extracted with AcOEt. The combined organic layers were dried over $MgSO_4$, were filtered and were evaporated under reduced pressure. The resulting crude product was purified by flash chromatography over silica gel using DCM/MeOH (99:1) to afford 4-(1-(4-methoxybenzyl)-1H-pyrazol-4-yl)-N-(4-methylpyrimidin-2-yl)-5-(trifluoromethyl)thiazol-2-amine (0.40 mmol, 180 mg, 51%).

UPLC-MS: RT=1.18 min; MS m/z $ES^+$=447.

N-(4-Methylpyrimidin-2-yl)-4-(1H-pyrazol-4-yl)-5-(trifluoromethyl)thiazol-2-amine According to Scheme 9 Step 4: A solution of 4-(1-(4-methoxybenzyl)-1H-pyrazol-4-yl)-N-(4-methylpyrimidin-2-yl)-5-(trifluoromethyl)thiazol-2-amine (0.40 mmol, 180 mg) and trifluoromethanesulfonic acid (4.84 mmol, 430 µL) in TFA (1 mL) was stirred for 8 minutes at 80° C. under microwave activation. The reaction solution was neutralized with a saturated aqueous solution of $Na_2CO_3$ and extracted with AcOEt. The combined organic layers were dried over $MgSO_4$, were filtered and were evaporated under reduced pressure to give a brown solid. The resulting crude product was purified by flash chromatography over silica gel using DCM/MeOH (100:0 to 95:5) to yield N-(4-methylpyrimidin-2-yl)-4-(1H-pyrazol-4-yl)-5-(trifluoromethyl)thiazol-2-amine (22 µmol, 7 mg, 5.5%) as a white solid.

UPLC-MS: RT=0.92 min; MS m/z $ES^+$=328.

Example 11

4-(5-Chloro-1H-pyrazol-4-yl)-N-(pyridin-2-yl)thiazol-2-amine (Final Compound 1-17)

Ethyl 1-(4-methoxybenzyl)-3-chloro-1H-pyrazole-4-carboxylate

According to Scheme 10, General procedure: Butyl lithium 2.5 M (0.92 mmol, 0.37 mL) was added to a solution of diisopropylamine (0.92 mmol, 0.13 mL) in THF (2 mL) at −78° C. and the reaction mixture was stirred at −78° C. for 5 minutes and then at room temperature. The resulting LDA solution was added at −78° C. to a solution of 1-(4-methoxybenzyl)-1H-pyrazole-4-carboxylate (0.7 mmol, 200 mg) in THF (2 mL) and the reaction mixture was stirred for 5 minutes at −78° C. Then a solution of hexachloroethane (1.15 mmol, 273 mg) in THF (2 mL) was added to the reaction mixture at −78° C. and the solution was stirred for 5 minutes at −78° C. and for 1 hour at room temperature. The reaction mixture was quenched with water (50 mL) and the aqueous phase was extracted with DCM. The organic phase was dried over $MgSO_4$, was filtered and was concentrated to yield a brown oil. The resulting crude product was purified by flash chromatography over silica gel using DCM as eluent to yield after evaporation ethyl 1-(4-methoxybenzyl)-3-chloro-1H-pyrazole-4-carboxylate (0.36 mmol, 105 mg, 46%) as a beige solid.

UPLC-MS: RT=1.09 min; MS m/z $ES^+$=294.

4-(5-Chloro-1H-pyrazol-4-yl)-N-(pyridin-2-yl)thiazol-2-amine was obtained as a white solid following the same experimental part as described for Example 1.

M.p.: 299-304° C.;

UPLC-MS: RT=0.84 min; MS m/z $ES^+$=278.

Example 12

4-(3-Fluoro-1H-pyrazol-4-yl)-N-(pyridin-2-yl)thiazol-2-amine and 4-(3-(phenylsulfonyl)-1H-pyrazol-4-yl)-N-(pyridin-2-yl)thiazol-2-amine (Final Compounds 1-35 and 1-39)

Ethyl 3-fluoro-1-(4-methoxybenzyl)-1H-pyrazole-4-carboxylate and ethyl 1-(4-methoxybenzyl)-3-(phenylsulfonyl)-1H-pyrazole-4-carboxylate According to Scheme 10: The reaction was done following the general procedure described for Example 9 using ethyl 1-(4-methoxybenzyl)-1H-pyrazole-4-carboxylate (3.84 mmol, 1.00 g) as starting material and N-fluoro-N-(phenylsulfonyl)benzenesulfonamide (3.84 mmol, 1.21 g) as electrophile. The resulting crude product was purified by flash chromatography over silica gel using cyclohexane/AcOEt (90:10) as eluent to yield after evaporation a mixture of ethyl 3-fluoro-1-(4-methoxybenzyl)-1H-pyrazole-4-carboxylate and ethyl 1-(4-methoxybenzyl)-3-(phenylsulfonyl)-1H-pyrazole-4-carboxylate (330 mg, 50/50).

4-(3-Fluoro-1H-pyrazol-4-yl)-N-(pyridin-2-yl)thiazol-2-amine was obtained as a white solid following the same experimental part as described for Example 1.

UPLC-MS: RT=0.76 min; MS m/z ES$^+$=262.

4-(3-(Phenylsulfonyl)-1H-pyrazol-4-yl)-N-(pyridin-2-yl)thiazol-2-amine was obtained as a white solid following the same experimental part as described for Example 1.

UPLC-MS: RT=0.76 min; MS m/z ES$^+$=384.

Example 13

4-(5-(4-Fluorophenyl)-1H-pyrazol-4-yl)-N-(4-methylpyrimidin-2-yl)thiazol-2-amine (Final Compound 1-73)

3-(4-Fluorophenyl)-N-methoxy-1-(4-methoxybenzyl)-N-methyl-1H-pyrazole-4-carboxamide According to Scheme 11 Step 1: A solution of 3-iodo-N-methoxy-1-(4-methoxybenzyl)-N-methyl-1H-pyrazole-4-carboxamide (2.49 mmol, 1.00 g), 4-fluorophenylboronic acid (2.99 mmol, 419 mg), Pd(dppf)Cl$_2$ (0.25 mmol, 204 mg) and N-ethyl-N-isopropylpropan-2-amine (4.99 mmol, 850 µL) in a mixture of dioxane/water (5 mL, 1:1) was heated at 180° C. for 50 minutes under microwave heating and a nitrogen atmosphere. AcOEt was added and the organic phase was washed with a saturated aqueous solution of Na$_2$CO$_3$. The organic layer was dried over MgSO$_4$, was filtered and was concentrated. The crude compound was purified by flash chromatography with silica gel using cyclohexane/AcOEt (100:0 to 50:50) to yield 3-(4-fluorophenyl)-N-methoxy-1-(4-methoxybenzyl)-N-methyl-1H-pyrazole-4-carboxamide (2.26 mmol, 833 mg, 90%).

LC-MS: RT=0.94 min; MS m/z ES$^+$=371.

4-(5-(4-Fluorophenyl)-1H-pyrazol-4-yl)-N-(4-methylpyrimidin-2-yl)thiazol-2-amine was obtained as a white solid following the same experimental part as described for Example 3.

UPLC-MS: RT=0.92 min; MS m/z ES$^+$=353.

Example 14

N-(4-Methylpyrimidin-2-yl)-4-(3-phenyl-1H-pyrazol-4-yl)thiazol-2-amine (Final Compound 1-79)

4-(1-(4-Methoxybenzyl)-3-phenyl-1H-pyrazol-4-yl)-N-(4-methylpyrimidin-2-yl)thiazol-2-amine According to Scheme 12 Step 1: A solution of 4-(3-bromo-1-(4-methoxybenzyl)-1H-pyrazol-4-yl)-N-(4-methylpyrimidin-2-yl)thiazol-2-amine (0.33 mmol, 150 mg), phenylboronic acid (0.39 mmol, 48 mg), Pd(PPh$_3$)$_4$ (49 µmol, 57 mg) and a saturated aqueous solution of NaHCO$_3$ (0.5 mL) in dioxane (0.5 mL) was stirred at 120° C. for 2 hours under microwave heating. The crude mixture was filtered through celite pad and washed with DCM. The filtrate was washed with water. The organic layer was dried over MgSO$_4$, was filtered and was concentrated. The crude compound was purified by flash chromatography with silica gel using DCM/AcOEt (100:0 to 70:30) to yield 4-(1-(4-methoxybenzyl)-3-phenyl-1H-pyrazol-4-yl)-N-(4-methylpyrimidin-2-yl)thiazol-2-amine (0.17 mmol, 77 mg, 52%).

LC-MS: RT=1.19 min; MS m/z ES$^+$=455.

N-(4-Methylpyrimidin-2-yl)-4-(3-phenyl-1H-pyrazol-4-yl)thiazol-2-amine

According to Scheme 12 Step 2: A solution of 4-(1-(4-methoxybenzyl)-3-phenyl-1H-pyrazol-4-yl)-N-(4-methylpyrimidin-2-yl)thiazol-2-amine (0.17 mmol, 77 mg) in TFA (1 mL) was stirred at 150° C. for 5 minutes under microwave heating. Water was added and was extracted with DCM. The organic layer was dried over MgSO$_4$, was filtered and was concentrated. The crude compound was purified by flash chromatography with silica gel using DCM/AcOEt (100:10 to 50:50) to yield N-(4-methylpyrimidin-2-yl)-4-(3-phenyl-1H-pyrazol-4-yl)thiazol-2-amine (90 µmol, 30 mg, 50%) as a yellow solid.

UPLC-MS: RT=0.9 min; MS m/z ES$^+$=335.

Example 15

4-(2-(Pyridin-2-ylamino)thiazol-4-yl)-1H-pyrazole-5-carbonitrile (Final Compound 1-26)

1-(4-Methoxybenzyl)-4-(2-(pyridin-2-ylamino)thiazol-4-yl)-1H-pyrazole-3-carbonitrile According to Scheme 13 Step 1: A solution of N-(4-(1-(4-methoxybenzyl)-3-chloro-1H-pyrazol-4-yl)thiazol-2-yl)pyridin-2-amine (75 µmol, 30 mg), KCN (75 µmol, 4.9 mg), Pd(PPh$_3$)$_4$ (7.5 µmol, 8.7 mg) and CuI (75 µmol, 14.4 mg) in acetonitrile (2 mL) was microwaved at 180° C. for 50 minutes under nitrogen. After evaporation of the solvent, the crude residue was dissolved in AcOEt. The organic phase was washed with a saturated aqueous solution of Na$_2$CO$_3$, was dried over MgSO$_4$, was filtered and was concentrated to yield 1-(4-methoxybenzyl)-4-(2-(pyridin-2-ylamino)thiazol-4-yl)-1H-pyrazole-3-carbonitrile (51 µmol, 20 mg, 68%).

LC-MS: RT=1.04 min; MS m/z ES$^+$=389.

4-(2-(Pyridin-2-ylamino)thiazol-4-yl)-1H-pyrazole-5-carbonitrile

According to Scheme 13 Step 2: A solution of 1-(4-methoxybenzyl)-4-(2-(pyridin-2-ylamino)thiazol-4-yl)-1H-pyrazole-3-carbonitrile (31 μmol, 12 mg) in TFA (1 mL) was microwaved for 3 minutes at 130° C. After evaporation of the solvent, the crude residue was dissolved in AcOEt. The organic phase was washed with a saturated aqueous solution of $Na_2CO_3$, was dried over $MgSO_4$, was filtered and was concentrated. The resulting crude product was purified by flash chromatography over silica gel using DCM/MeOH (100:0 to 95:5) as eluent to yield 4-(2-(pyridin-2-ylamino)thiazol-4-yl)-1H-pyrazole-5-carbonitrile (15 μmol, 4 mg, 48%) as a white solid.

UPLC-MS: RT=0.65 min; MS m/z ES+=269.

Example 16

N-(Pyrimidin-2-yl)-4-(3-(pyrrolidin-1-yl)-1H-pyrazol-4-yl)thiazol-2-amine (Final Compound 1-76)

N-Methoxy-1-(4-methoxybenzyl)-N-methyl-3-(pyrrolidin-1-yl)-1H-pyrazole-4-carboxamide According to Scheme 14 Step 1: A solution of 3-chloro-N-methoxy-1-(4-methoxybenzyl)-N-methyl-1H-pyrazole-4-carboxamide (0.97 mmol, 300 mg) and pyrrolidine (14.5 mmol, 1.03 g) in NMP (10 mL) was stirred at 220° C. for 40 minutes under microwave heating. AcOEt was then added and the organic phase was washed with water. The organic layer was dried over $MgSO_4$, was filtered and was concentrated. The crude compound was purified by flash chromatography with silica gel using cyclohexane/AcOEt (100:0 to 50:50) to yield N-methoxy-1-(4-methoxybenzyl)-N-methyl-3-(pyrrolidin-1-yl)-1H-pyrazole-4-carboxamide (0.87 mmol, 300 mg, 90%) as an oil.

LC-MS: RT=0.95 min; MS m/z ES+=345.

N-(Pyrimidin-2-yl)-4-(3-(pyrrolidin-1-yl)-1H-pyrazol-4-yl)thiazol-2-amine was obtained as a beige solid following the same experimental part as described for Example 3.

UPLC-MS: RT=0.6 min; MS m/z ES+=314.

Example 17

Cyclopropyl(4-(2-(pyrimidin-2-ylamino)thiazol-4-yl)-1H-pyrazol-5-yl)methanone (Final Compound 1-66)

Ethyl 3-(cyclopropanecarbonyl)-1-(4-methoxybenzyl)-1H-pyrazole-4-carboxylate According to Scheme 16: Butyl lithium 2.5 M (9.9 mmol, 4 mL) was added to a solution of diisopropylamine (9.9 mmol, 1.4 mL) in THF (20 mL) at −78° C. and the reaction mixture was stirred at −78° C. for 5 minutes and then at room temperature. To the resulting LDA solution was added at −78° C. a solution of ethyl 1-(4-methoxybenzyl)-1H-pyrazole-4-carboxylate (7.61 mmol, 1.98 g) in THF (30 mL) and the reaction mixture was stirred for 15 minutes at −78° C. Then N-methoxy-N-methylcyclopropanecarboxamide (9.14 mmol, 1.18 g) in THF (10 mL) was added and the reaction mixture was stirred at room temperature. The reaction mixture was diluted with AcOEt and washed with a saturated aqueous solution of $NH_4Cl$. The combined organic phases were dried over $MgSO_4$, were filtered and solvents were evaporated. The crude mixture was purified by flash chromatography over silica gel using cyclohexane/AcOEt (90:10) as eluent to yield ethyl 3-(cyclopropanecarbonyl)-1-(4-methoxybenzyl)-1H-pyrazole-4-carboxylate (0.74 mmol, 244 mg, 9%).

UPLC-MS: RT=1.08 min; MS m/z ES+=329.

Cyclopropyl(4-(2-(pyrimidin-2-ylamino)thiazol-4-yl)-1H-pyrazol-5-yl)methanone was obtained as a white solid following the same experimental part as described for Example 1.

M.p.: 244° C.;

UPLC-MS: RT=0.76 min; MS m/z ES+=313.

Example 18

4-(1-(4-Methoxybenzyl)-3-(2-methoxyethyl)-1H-pyrazol-4-yl)-N-(4-methylpyrimidin-2-yl)thiazol-2-amine (Final Compound 1-83)

Ethyl 5-formyl-1-(4-methoxybenzyl)-1H-pyrazole-4-carboxylate

According to Scheme 17 Step 1: Butyl lithium 2.5 M (16.9 mmol, 8.45 mL) was added to a solution of diisopropylamine (16.9 mmol, 2.37 mL) in THF (10 mL) at −78° C. and the reaction mixture was stirred at −78° C. for 5 minutes and then at room temperature. To the resulting LDA solution was added at −78° C. a solution of ethyl 1-(4-methoxybenzyl)-1H-pyrazole-4-carboxylate (7.68 mmol, 2 g) in THF (30 mL) and the reaction mixture was stirred for 5 minutes at −78° C. N,N-Dimethylformamide (61.5 mmol, 4.73 mL) was added and then the reaction mixture was stirred at room temperature. The reaction mixture was diluted with AcOEt and was washed with a saturated aqueous solution of $NH_4Cl$. The combined organic phases were dried over $MgSO_4$, were filtered and were evaporated. The crude mixture was purified by flash chromatography over silica gel using cyclohexane/AcOEt (100:0 to 80:20) as eluent to yield ethyl 5-formyl-1-(4-methoxybenzyl)-1H-pyrazole-4-carboxylate (4.62 mmol, 1.33 g, 60%).

UPLC-MS: RT=1.06 min; MS m/z ES+=289.

(E)-Ethyl 1-(4-methoxybenzyl)-5-(2-methoxyvinyl)-1H-pyrazole-4-carboxylate

According to Scheme 17 Step 2: To a solution of (methoxymethyl)triphenylphosphonium chloride (10.4 mmol, 3.57 g) in THF (3 mL) was added, at 0° C., potassium 2-methylpropan-2-olate (10.4 mmol, 1.17 g). After stirring for 45 minutes, ethyl 5-formyl-1-(4-methoxybenzyl)-1H-pyrazole-4-carboxylate (3.47 mmol, 1.00 g) in THF (2 mL) was added to the reaction mixture and the resulting solution was stirred at room temperature. The reaction mixture was carefully quenched at 0° C. with a saturated aqueous solution of $NH_4Cl$. The aqueous layer was extracted with AcOEt and the organic layer washed with water and brine.

The combined organic phases were dried over $MgSO_4$, were filtered and were evaporated. The crude material was triturated with $Et_2O$ at 0° C. and filtered. The filtrate was concentrated to afford (E)-ethyl 1-(4-methoxybenzyl)-5-(2-methoxyvinyl)-1H-pyrazole-4-carboxylate (1.30 g, 70% purity, 83%) which was used in the next step without further purification.

UPLC-MS: RT=0.98 min; MS m/z ES+=317.

Ethyl 1-(4-methoxybenzyl)-5-(2-methoxyethyl)-1H-pyrazole-4-carboxylate

According to Scheme 17 Step 3: To a mixture of (E)-ethyl 1-(4-methoxybenzyl)-5-(2-methoxyvinyl)-1H-pyrazole-4-carboxylate (1.58 mmol, 500 mg) in MeOH (7.9 mL) was hydrogenated in a H-Cube® with Pd/C under a 20 bar $H_2$ atmosphere. The reaction mixture was filtered through celite and the filtrate was concentrated to dryness to afford ethyl 1-(4-methoxybenzyl)-5-(2-methoxyethyl)-1H-pyrazole-4-carboxylate (1.57 mmol, 500 mg, 99%).

UPLC-MS: RT=1.03 min; MS m/z $ES^+$=319.

4-(1-(4-Methoxybenzyl)-3-(2-methoxyethyl)-1H-pyrazol-4-yl)-N-(4-methylpyrimidin-2-yl)thiazol-2-amine was obtained as a yellow solid following the same experimental part as described for Example 3.

UPLC-MS: RT=0.73 min; MS m/z $ES^+$=317.

Example 19

N-Methyl-2-(4-(5-methyl-2-(pyridin-2-ylamino)thiazol-4-yl)-1H-pyrazol-1-yl)acetamide (Final Compound 1-32)

Ethyl 2-(4-(5-methyl-2-(pyridin-2-ylamino)thiazol-4-yl)-1H-pyrazol-1-yl)acetate

According to Scheme 18 Step 1: Ethyl-2-bromoacetate (0.27 mmol, 45.4 mg) was added to a suspension of N-(5-methyl-4-(1H-pyrazol-4-yl)thiazol-2-yl)pyridin-2-amine (0.27 mmol, 70 mg) and $K_2CO_3$ (0.54 mmol, 82 mg) in DMSO (4 mL) and then the reaction mixture was heated at 70° C. for 3 hours. Water was added and the aqueous phase was extracted with AcOEt. The organic phase was dried over $MgSO_4$, was filtered and was concentrated under reduced pressure. The crude product was purified by flash chromatography over silica gel using cyclohexane/AcOEt (90:10 to 30:70) as eluent to afford ethyl 2-(4-(5-methyl-2-(pyridin-2-ylamino)thiazol-4-yl)-1H-pyrazol-1-yl)acetate (87 μmol, 30 mg, 32%) as a white powder.

UPLC-MS: RT=0.78 min; MS m/z $ES^+$=344.

N-Methyl-2-(4-(5-methyl-2-(pyridin-2-ylamino)thiazol-4-yl)-1H-pyrazol-1-yl)acetamide According to Scheme 18 Step 2: A solution of ethyl 2-(4-(5-methyl-2-(pyridin-2-ylamino)thiazol-4-yl)-1H-pyrazol-1-yl)acetate (87 μmol, 30 mg) and methylamine (0.26 mmol, 8.1 mg) in MeOH (4 mL) was heated at 60° C. for 4 hours. After evaporation, the crude product was purified by flash chromatography over silica gel using DCM/MeOH (100:0 to 90:10) as eluent to afford N-methyl-2-(4-(5-methyl-2-(pyridin-2-ylamino)thiazol-4-yl)-1H-pyrazol-1-yl)acetamide (40 μmol, 13 mg, 45%) as a white powder.

UPLC-MS: RT=0.60 min; MS m/z $ES^+$=329.

Example 20

4-(5-Fluoro-2-(6-methylpyridin-2-ylamino)thiazol-4-yl)-1H-pyrazole-1-carboxamide (Final Compound 1-30)

According to Scheme 19: A solution of N-(5-fluoro-4-(1H-pyrazol-4-yl)thiazol-2-yl)-6-methylpyridin-2-amine (1.22 mmol, 337 mg), potassium cyanate (1.47 mmol, 119 mg), AcOH (5 mL) and water (5 mL) was stirred for 2.5 hours at room temperature. The reaction mixture was quenched with water (100 mL) and the precipitate was filtered. The resulting crude product was purified by flash chromatography over silica gel using DCM/EDA (80:20; EDA: DCM/EtOH/$NH_3$ 90:9:1) as eluent to yield 4-(5-fluoro-2-(6-methylpyridin-2-ylamino)thiazol-4-yl)-1H-pyrazole-1-carboxamide (31 μmol, 10 mg, 3%) as a yellow solid.

UPLC-MS: RT=0.99 min; MS m/z $ES^+$=319.

Example 21

N,N-Dimethyl-4-(5-methyl-2-(pyridin-2-ylamino)thiazol-4-yl)-1H-pyrazole-1-carboxamide (Final Compound 1-36)

According to Scheme 19: A solution of 5-methyl-4-(1H-pyrazol-4-yl)-N-(pyridin-2-yl)thiazol-2-amine (0.39 mmol, 100 mg), 2,3,4,6,7,8,9,10-octahydropyrimido[1,2-a]azepine (0.39 mmol, 58 μL) and dimethylcarbamic chloride (0.39 mmol, 36 μL) in THF (5 mL) was stirred at room temperature during one day. Then, 2,3,4,6,7,8,9,10-octahydropyrimido[1,2-a]azepine (0.39 mmol, 58 μL) and dimethylcarbamic chloride (0.39 mmol, 36 μL) were added and the mixture was stirred at room temperature during 3 days. The solution was diluted with water (50 mL) and the aqueous layer was extracted twice with DCM. The organic phases were dried over $MgSO_4$, were filtered and were concentrated to afford a beige solid. The crude compound was purified by flash chromatography with silica gel using DCM/MeOH (98:2) as eluent to afford N,N-dimethyl-4-(5-methyl-2-(pyridin-2-ylamino)thiazol-4-yl)-1H-pyrazole-1-carboxamide (0.23 mmol, 76 mg, 60%) as a beige solid.

M.p.: 181-185° C.;
HPLC-MS: RT=1.91 min; MS m/z $ES^+$=329.

Example 22

4-(1-(4-Chlorophenylsulfonyl)-1H-pyrazol-4-yl)-5-methyl-N-(pyridin-2-yl)thiazol-2-amine (Final Compound 1-9)

According to Scheme 20: 4-Chlorobenzene-1-sulfonyl chloride (0.39 mmol, 82 mg) was added dropwise to a solution of N-(5-methyl-4-(1H-pyrazol-4-yl)thiazol-2-yl)pyridin-2-amine (0.39 mmol, 100 mg), $Et_3N$ (0.39 mmol, 54 μL) in THF (3 mL) and the reaction mixture was stirred for 5 hours at 70° C. The reaction mixture was quenched with water (50 mL) and the aqueous phase was extracted with DCM. The organic phase was dried over $MgSO_4$, was filtered and was concentrated to yield a brown solid. The resulting crude product was purified by flash chromatography over silica gel using DCM/MeOH (99:1) as eluent and washed with $Et_2O$ to yield after evaporation 4-(1-(4-chlorophenylsulfonyl)-1H-pyrazol-4-yl)-5-methyl-N-(pyridin-2-yl)thiazol-2-amine (0.16 mmol, 70 mg, 42%) as a white solid.

M.p.: 232-233° C.;
UPLC-MS: RT=1.12 min; MS m/z ES$^+$=432.

Example 23

(4-(5-Methyl-2-(pyridin-2-ylamino)thiazol-4-yl)-1H-pyrazol-1-yl)(pyridin-2-yl)methanone (Final Compound 1-63)

According to Scheme 21: To a solution of 5-methyl-4-(1H-pyrazol-4-yl)-N-(pyridin-2-yl)thiazol-2-amine (0.19 mmol, 50 mg) in DCM (2 mL) was added Et$_3$N (0.78 mmol, 108 µL). After stirring for 10 minutes, picolinoyl chloride hydrochloride (0.39 mmol, 69.2 mg) was added. The reaction mixture was stirred for 3 hours at room temperature. The solvent was then removed under reduced pressure to afford a yellow solid. The crude mixture was solubilised in DMF. A white solid was precipitated, was filtered and was washed with MeOH. After evaporation, 4-(5-methyl-2-(pyridin-2-ylamino)thiazol-4-yl)-1H-pyrazol-1-yl)(pyridin-2-yl)methanone (50 µmol, 18 mg, 25%) was obtained as a white solid.

M.p.: 226-228° C.;
UPLC-MS: RT=0.84 min; MS m/z ES$^+$=363.

Example 24

N-((4-(5-Methyl-2-(pyridin-2-ylamino)thiazol-4-yl)-1H-pyrazol-1-yl)methyl)acetamide (Final Compound 1-61)

N-((4-(2-((Acetamidomethyl)(pyridin-2-yl)amino)-5-methylthiazol-4-yl)-1H-pyrazol-1-yl)methyl)acetamide According to Scheme 22, Step 1: A mixture of 5-methyl-4-(1H-pyrazol-4-yl)-N-(pyridin-2-yl)thiazol-2-amine (0.17 mmol, 45 mg), formaldehyde (1.40 mmol, 42 mg) and acetamide (1.40 mmol, 83 mg) was heated at 150° C. for 1 hour. After cooling the reaction mixture to room temperature, AcOEt was added and the organic phase was washed with a saturated aqueous solution of NaHCO$_3$. The organic phases were dried over MgSO$_4$, were filtered and were concentrated to afford N-((4-(2-((acetamidomethyl)(pyridin-2-yl)amino)-5-methylthiazol-4-yl)-1H-pyrazol-1-yl)methyl)acetamide (75 µmol, 30 mg, 43%).

UPLC-MS: RT=0.73 min; MS m/z ES$^+$=400.

N-((4-(5-Methyl-2-(pyridin-2-ylamino)thiazol-4-yl)-1H-pyrazol-1-yl)methyl)acetamide According to Scheme 22, Step 2: A solution of N-((4-(2-((acetamidomethyl)(pyridin-2-yl)amino)-5-methylthiazol-4-yl)-1H-pyrazol-1-yl)methyl)acetamide (75 µmol, 30 mg) in 1 mL of HCl (1 N) was stirred at room temperature for 1 hour. The solution was then basified to pH 8 and the aqueous phase was extracted with AcOEt. The organic phases were dried over MgSO$_4$, were filtered and were concentrated. The crude compound was purified by flash chromatography with silica gel using DCM/MeOH (100:0 to 95:5) and then by SCX-2 with a catch and release methodology to afford N-((4-(5-methyl-2-(pyridin-2-ylamino)thiazol-4-yl)-1H-pyrazol-1-yl)methyl)acetamide (55 mmol, 18 mg, 73%) as a beige solid.

M.p.: 175° C.;
UPLC-MS: RT=0.6 min; MS m/z ES$^+$=329.

Example 25

4-(5-(Dimethylamino)-1H-pyrazol-4-yl)-N-(4-methylpyrimidin-2-yl)thiazol-2-amine (Final Compound 1-56)

Ethyl 3-amino-1-(4-methoxybenzyl)-1H-pyrazole-4-carboxylate

According to Scheme 15 Step 1: 1-(Chloromethyl)-4-methoxybenzene (12.9 mmol, 2.02 g) followed by K$_2$CO$_3$ (25.8 mmol, 3.56 g) were added to a solution of ethyl 3-amino-1H-pyrazole-4-carboxylate (12.9 mmol, 2.00 g) in acetonitrile (10 mL) and then the reaction mixture was heated at 60° C. for 3 hours. After evaporation of the solvent, a saturated solution of Na$_2$CO$_3$ was added and the aqueous phase was extracted with AcOEt. The organic phase was dried over Na$_2$SO$_4$, was filtered and was concentrated under reduced pressure. The crude product was purified by flash chromatography over silica gel using cyclohexane/AcOEt (100:0 to 20:80) as eluent to afford ethyl 3-amino-1-(4-methoxybenzyl)-1H-pyrazole-4-carboxylate (6.90 mmol, 1.90 g, 53%) as a white powder.

UPLC-MS: RT=0.82 min; MS m/z ES$^+$=276.

Ethyl 3-(dimethylamino)-1-(4-methoxybenzyl)-1H-pyrazole-4-carboxylate

According to Scheme 15 Step 2: NaBH$_3$CN (7.26 mmol, 456 mg) was added to a solution of ethyl 3-amino-1-(4-methoxybenzyl)-1H-pyrazole-4-carboxylate (3.63 mmol, 1.00 g) and formaldehyde (109 mmol, 8.84 g) in acetic acid (10 mL). The reaction mixture was stirred for 4 hours at room temperature and was then extracted with AcOEt. After neutralization of the aqueous phase, it was extracted with AcOEt. The organic phase was dried over MgSO$_4$, was filtered and was concentrated under reduced pressure. The crude product was purified by flash chromatography over silica gel using cyclohexane/AcOEt (90:10 to 0:100) as eluent to afford ethyl 3-(dimethylamino)-1-(4-methoxybenzyl)-1H-pyrazole-4-carboxylate (1.98 mmol, 600 mg, 54%) as an oil.

UPLC-MS: RT=0.97 min; MS m/z ES$^+$=304.

4-(5-(Dimethylamino)-1H-pyrazol-4-yl)-N-(4-methylpyrimidin-2-yl)thiazol-2-amine was obtained as a beige solid following the same experimental part as described for Example 2.

UPLC-MS: RT=0.64 min; MS m/z ES$^+$=302.

The compounds in the following Tables have been synthesized according to the same methods as previous examples 1 to 25, as denoted in the column denoted as "Exp. nr". The compounds denoted with the asterisk have been exemplified in the Examples.

TABLE 1
Compounds prepared according to the Examples.
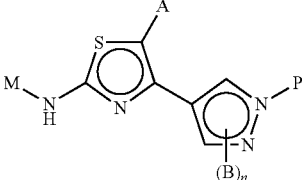
| Co. nr. | Exp nr. | M | A | |
|---|---|---|---|---|
| 1-1* | 4 | NC-pyridin-2-yl | Me— | 1H-pyrazol-4-yl |
| 1-2 | 5 | pyridin-2-yl | morpholin-4-yl | 1H-pyrazol-4-yl |
| 1-3 | 4 | 3-CN-pyridin-2-yl | Me— | 1H-pyrazol-4-yl |
| 1-4* | 5 | pyridin-2-yl | piperidin-1-yl | 1H-pyrazol-4-yl |
| 1-5 | 1 | pyridin-2-yl | H— | 5-(furan-2-yl)-1H-pyrazol-4-yl |
| 1-6 | 1 | pyridin-2-yl | H— | 5-(cyclopropylmethyl)-1H-pyrazol-4-yl |
| 1-7* | 1 | pyridin-2-yl | H— | 5-isobutyl-1H-pyrazol-4-yl |
| 1-8 | 5 | pyridin-2-yl | pyrrolidin-1-yl | 1H-pyrazol-4-yl |

TABLE 1-continued
Compounds prepared according to the Examples.
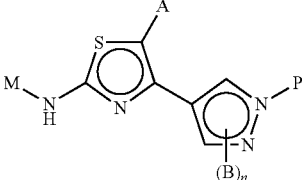
| Co. nr. | Exp nr. | M | A | |
|---|---|---|---|---|
| 1-9* | 22 | 2-pyridyl | Me— | 1-(4-chlorophenylsulfonyl)pyrazol-4-yl |
| 1-10 | 6 | 6-fluoropyridin-2-yl | F— | 1H-pyrazol-4-yl |
| 1-11* | 6 | 6-methylpyridin-2-yl | F— | 1H-pyrazol-4-yl |
| 1-12 | 5 | 2-pyridyl | Me₂N— | 1H-pyrazol-4-yl |
| 1-13 | 6 | 6-chloropyridin-2-yl | F— | 1H-pyrazol-4-yl |
| 1-14* | 2 | 6-iodopyridin-2-yl | Me— | 1H-pyrazol-4-yl |
| 1-15 | 2 | 3-iodopyridin-2-yl | Me— | 1H-pyrazol-4-yl |
| 1-16 | 3 | 2-pyrimidinyl | Me— | 1H-pyrazol-4-yl |

TABLE 1-continued

Compounds prepared according to the Examples.

| Co. nr. | Exp nr. | M | A | (pyrazole with P, B) |
|---|---|---|---|---|
| 1-17* | 11 | 2-pyridyl | H— | 3-Cl-pyrazol-4-yl, NH |
| 1-18* | 8 | 2-pyridyl | MeOCH₂— | pyrazol-4-yl, NH |
| 1-19* | 3 | 4-F-2-pyridyl | Me— | pyrazol-4-yl, NH |
| 1-20 | 8 | 2-pyridyl | Et₂NCH₂— | pyrazol-4-yl, NH |
| 1-21 | 8 | 2-pyridyl | morpholinyl-CH₂— | pyrazol-4-yl, NH |
| 1-22 | 8 | 2-pyridyl | EtOCH₂— | pyrazol-4-yl, NH |
| 1-23 | 3 | 3-F-6-Me-2-pyridyl | Me— | pyrazol-4-yl, NH |
| 1-24 | 3 | 5-MeO-2-pyridyl | Me— | pyrazol-4-yl, NH |

TABLE 1-continued

Compounds prepared according to the Examples.

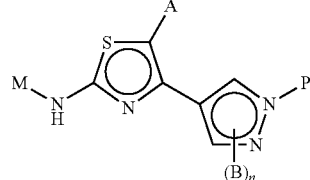

| Co. nr. | Exp nr. | M | A | |
|---|---|---|---|---|
| 1-25 | 6 | pyrazinyl | F— | 1H-pyrazol-4-yl |
| 1-26* | 15 | pyridin-2-yl | H— | 3-cyano-1H-pyrazol-4-yl |
| 1-27 | 1 | 1-methyl-1H-pyrazol-3-yl | H— | 1H-pyrazol-4-yl |
| 1-28* | 7 | 5-fluoropyridin-2-yl | F— | 1H-pyrazol-4-yl |
| 1-29 | 1 | pyridin-2-yl | H— | 3-(2,2,2-trifluoroethyl)-1H-pyrazol-4-yl |
| 1-30* | 20 | 6-methylpyridin-2-yl | F— | 1-carbamoyl-1H-pyrazol-4-yl |
| 1-31 | 1 | 4-methylpyrimidin-2-yl | H— | 1H-pyrazol-4-yl |
| 1-32* | 19 | pyridin-2-yl | Me— | 1-(methylcarbamoylmethyl)-1H-pyrazol-4-yl |

TABLE 1-continued

Compounds prepared according to the Examples.

| Co. nr. | Exp nr. | M | A | (pyrazole-P/B) |
|---|---|---|---|---|
| 1-33 | 3 | 4-methylpyrimidin-2-yl | Me— | 1H-pyrazol-4-yl |
| 1-34 | 3 | 5-methylpyrimidin-2-yl | Me— | 1H-pyrazol-4-yl |
| 1-35* | 12 | pyridin-2-yl | H— | 3-F-1H-pyrazol-4-yl |
| 1-36* | 21 | pyridin-2-yl | Me— | 1-(N,N-dimethylcarbamoyl)pyrazol-4-yl |
| 1-37 | 1 | pyridin-2-yl | H— | 3-Ph-1H-pyrazol-4-yl |
| 1-38 | 3 | pyrimidin-4-yl | Me— | 1H-pyrazol-4-yl |
| 1-39* | 12 | pyridin-2-yl | H— | 3-(PhO₂S)-1H-pyrazol-4-yl |
| 1-40 | 1 | pyridin-2-yl | H— | 3-(MeOCH₂)-1H-pyrazol-4-yl |

TABLE 1-continued

Compounds prepared according to the Examples.

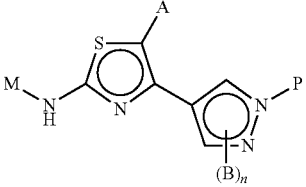

| Co. nr. | Exp nr. | M—⌇ | A—⌇ | (pyrazole-P/B) |
|---|---|---|---|---|
| 1-41 | 1 | 2-methylthiazol-4-yl | H— | 1H-pyrazol-4-yl |
| 1-42 | 1 | 4-methylthiazol-2-yl | H— | 1H-pyrazol-4-yl |
| 1-43 | 3 | 6-(fluoromethyl)pyridin-2-yl | Me— | 1H-pyrazol-4-yl |
| 1-44 | 3 | 6-(difluoromethyl)pyridin-2-yl | Me— | 1H-pyrazol-4-yl |
| 1-45* | 9 | pyrimidin-2-yl | Cl— | 1H-pyrazol-4-yl |
| 1-46 | 1 | 4-ethylpyrimidin-2-yl | Me— | 1H-pyrazol-4-yl |
| 1-47 | 1 | 5-fluoropyrimidin-2-yl | Me— | 1H-pyrazol-4-yl |
| 1-48 | 25 | pyridin-2-yl | H— | 3-(dimethylamino)-1H-pyrazol-4-yl |

TABLE 1-continued

Compounds prepared according to the Examples.

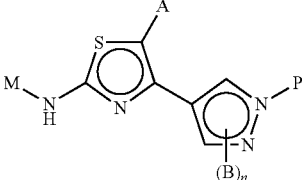

| Co. nr. | Exp nr. | M⸺ | A⸺ | [pyrazole with P, (B)ₙ] |
|---|---|---|---|---|
| 1-49 | 9 | 4-methylpyrimidin-2-yl | Cl⸺ | pyrazol-4-yl, NH |
| 1-50 | 1 | 1-methyl-2-oxopyrrolidin-3-yl | H⸺ | pyrazol-4-yl, NH |
| 1-51 | 10 | pyrimidin-2-yl | F₃C⸺ | pyrazol-4-yl, NH |
| 1-52 | 3 | 4-iPr-pyrimidin-2-yl | Me⸺ | pyrazol-4-yl, NH |
| 1-53 | 1 | 4-MeO-pyrimidin-2-yl | H⸺ | pyrazol-4-yl, NH |
| 1-54 | 17 | 4-methylpyrimidin-2-yl | H⸺ | 3-acetyl-pyrazol-4-yl, NH |
| 1-55 | 1 | 5-F-pyrimidin-2-yl | H⸺ | pyrazol-4-yl, NH |
| 1-56* | 25 | 4-methylpyrimidin-2-yl | H⸺ | 3-(dimethylamino)-pyrazol-4-yl, NH |

TABLE 1-continued

Compounds prepared according to the Examples.

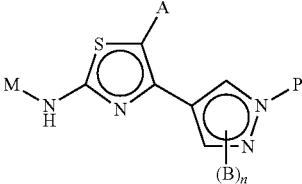

| Co. nr. | Exp nr. | M | A | (pyrazole group) |
|---|---|---|---|---|
| 1-57 | 16 | 4-methylpyrimidin-2-yl | H— | 3-(piperidin-1-yl)-1H-pyrazol-4-yl |
| 1-58* | 10 | 4-methylpyrimidin-2-yl | F₃C— | 1H-pyrazol-4-yl |
| 1-59 | 1 | pyrimidin-2-yl | H— | 1H-pyrazol-4-yl |
| 1-60 | 16 | 4-methylpyrimidin-2-yl | H— | 3-(morpholin-4-yl)-1H-pyrazol-4-yl |
| 1-61* | 24 | pyridin-2-yl | Me— | 1-(acetamidomethyl)-1H-pyrazol-4-yl |
| 1-62 | 1 | 4-cyclopropylpyrimidin-2-yl | Me— | 1H-pyrazol-4-yl |
| 1-63* | 23 | pyridin-2-yl | Me— | 1-(pyridin-2-ylcarbonyl)-1H-pyrazol-4-yl |

TABLE 1-continued

Compounds prepared according to the Examples.

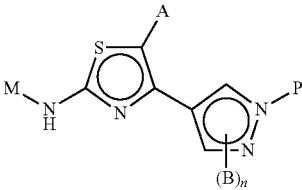

| Co. nr. | Exp nr. | M— | A— | (pyrazole with P, B) |
|---|---|---|---|---|
| 1-64 | 16 | 4-methylpyrimidin-2-yl | H— | 3-(diethylamino)-1H-pyrazol-4-yl |
| 1-65 | 25 | pyrimidin-2-yl | H— | 3-(dimethylamino)-1H-pyrazol-4-yl |
| 1-66* | 17 | pyrimidin-2-yl | H— | 3-(cyclopropanecarbonyl)-1H-pyrazol-4-yl |
| 1-67* | 17 | pyrimidin-2-yl | H— | 3-acetyl-1H-pyrazol-4-yl |
| 1-68 | 5 | pyrimidin-2-yl | N(Me)CH₂CH₂OMe | 1H-pyrazol-4-yl |
| 1-69 | 1 | 5-fluoro-4-methylpyrimidin-2-yl | H— | 1H-pyrazol-4-yl |
| 1-70 | 3 | 5-fluoro-4-methylpyrimidin-2-yl | Me— | 1H-pyrazol-4-yl |

TABLE 1-continued

Compounds prepared according to the Examples.

| Co. nr. | Exp nr. | M | A | (B)n pyrazole |
|---|---|---|---|---|
| 1-71 | 16 | pyrimidin-2-yl | H— | 4-(dimethylamino-methyl)-1H-pyrazol-... |
| 1-72 | 16 | pyrimidin-2-yl | H— | 3-(methylamino)-1H-pyrazol-4-yl |
| 1-73* | 13 | pyrimidin-2-yl | H— | 3-(4-fluorophenyl)-1H-pyrazol-4-yl |
| 1-74 | 1 | pyrimidin-2-yl | H— | 3-(methoxymethyl)-1H-pyrazol-4-yl |
| 1-75 | 3 | pyrimidin-2-yl | cyclobutyl | 1H-pyrazol-4-yl |
| 1-76* | 16 | pyrimidin-2-yl | H— | 3-(pyrrolidin-1-yl)-1H-pyrazol-4-yl |
| 1-77 | 16 | pyrimidin-2-yl | H— | 3-[(2-methoxyethyl)(methyl)amino]-1H-pyrazol-4-yl |

TABLE 1-continued

Compounds prepared according to the Examples.

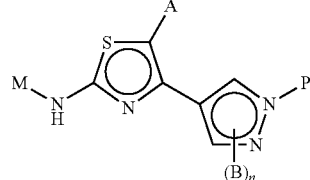

| Co. nr. | Exp nr. | M | A | (pyrazole group) |
|---|---|---|---|---|
| 1-78 | 16 | 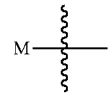 | H— | 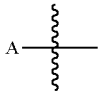 |
| 1-79* | 14 | 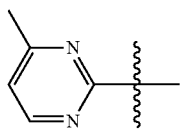 [SMILES: *c1nccc(C)n1] | H— | 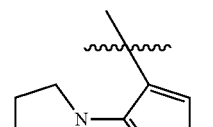 |
| 1-80 | 1 | 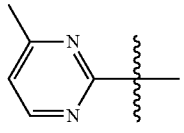 | H— | 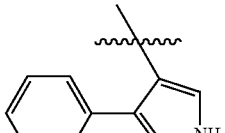 |
| 1-81 | 1 | 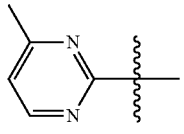 | H— | 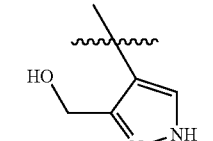 |
| 1-82 | 16 | 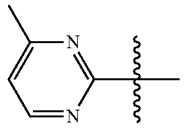 | H— | 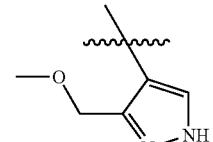 |
| 1-83* | 18 | 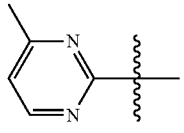 | H— | 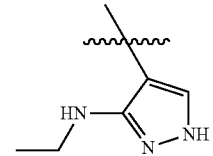 [SMILES: *c1c[nH]nc1NCC] |

LC-MS and UPLC-MS Methods:
Method 1

LC-MS were recorded on Waters Micromass ZQ 2996 system with the following conditions: Reversed phase HPLC was carried out on Zorbax SB-C18 cartridge (1.8 μm, 4.6×30 mm) from Agilent, with a flow rate of 1.5 mL/min. The gradient conditions used are: 90% A (water+0.1% of formic acid), 10% B (acetonitrile+0.1% of formic acid) to 100% B at 3.5 minutes, kept till 3.7 minutes and equilibrated to initial conditions at 3.8 minutes until 4.5 minutes. Injection volume 5-20 μL. ES MS detector was used, acquiring both in positive and negative ionization modes. Cone voltage was 30 V for both positive and negative ionization modes.

Method 2

UPLC-MS were recorded on Waters ACQUITY HPLC with the following conditions: Reversed phase HPLC was carried out on BEH-C18 cartridge (1.7 μm, 2.1×50 mm) from Waters, with a flow rate of 0.8 mL/min. The gradient conditions used are: 90% A (water+0.1% of formic acid), 10% B (acetonitrile+0.1% of formic acid) to 100% B at 1.3 minutes, kept till 1.6 minutes and equilibrated to initial conditions at 1.7 minutes until 2.0 minutes. Injection volume 5 μL. ES MS detector was used, acquiring both in positive and negative ionization modes.

All mass spectra were taken under electrospray ionisation (ESI) methods.

TABLE 2

Physico-chemical data for some compounds (nd = not determined).

| Co. Nr | Melting point (° C.) | MW (theor) | [MH+] | RT (min) | LCMS Method | Physical form |
| --- | --- | --- | --- | --- | --- | --- |
| 1-1 | 331 | 282.32 | 283 | 1.90 | Method 1 | Beige solid |
| 1-2 | 230-231 | 328.39 | 329 | 0.58 | Method 2 | Beige solid |
| 1-3 | nd | 282.32 | 283 | 0.78 | Method 2 | Yellow solid |
| 1-4 | 238 | 326.42 | 327 | 0.81 | Method 2 | Pale yellow solid |
| 1-5 | nd | 309.35 | 310 | 0.70 | Method 2 | White solid |
| 1-6 | nd | 297.38 | 298 | 0.75 | Method 2 | White solid |
| 1-7 | nd | 299.39 | 300 | 0.82 | Method 2 | Yellow solid |
| 1-8 | 209 | 312.39 | 313 | 0.72 | Method 2 | Pale yellow solid |
| 1-9 | 232-233 | 431.92 | 432 | 1.12 | Method 2 | White solid |
| 1-10 | 237 | 279.27 | 280 | 0.94 | Method 2 | Pale yellow solid |
| 1-11 | 204 | 275.30 | 276 | 0.94 | Method 2 | Beige solid |
| 1-12 | 232 | 286.36 | 287 | 0.74 | Method 2 | Yellow solid |
| 1-13 | 239 | 295.72 | 296 | 0.74 | Method 2 | Yellow solid |
| 1-14 | >260 | 383.21 | 384 | 1.02 | Method 2 | White solid |
| 1-15 | 243-245 | 383.21 | 384 | 1.02 | Method 2 | White solid |
| 1-16 | 298-300 | 258.30 | 259 | 0.75 | Method 2 | Beige solid |
| 1-17 | 299-304 | 277.73 | 278 | 0.84 | Method 2 | White solid |
| 1-18 | nd | 287.34 | 288 | 0.75 | Method 2 | White solid |
| 1-19 | 283 | 275.30 | 276 | 0.87 | Method 2 | Beige solid |
| 1-20 | nd | 328.44 | 329 | 0.59 | Method 2 | Beige solid |
| 1-21 | nd | 342.42 | 343 | 0.56 | Method 2 | White solid |
| 1-22 | nd | 301.37 | 302 | 0.82 | Method 2 | White solid |
| 1-23 | 323 | 289.33 | 290 | 0.96 | Method 2 | Beige solid |
| 1-24 | 229 | 287.34 | 288 | 0.76 | Method 2 | Beige solid |
| 1-25 | 279 | 262.27 | 263 | 0.74 | Method 2 | Beige solid |
| 1-26 | nd | 268.30 | 269 | 0.65 | Method 2 | White powder |
| 1-27 | 209-211 | 246.29 | 247 | 0.54 | Method 2 | Beige solid |
| 1-28 | 239 (dec) | 279.27 | 280 | 0.89 | Method 2 | Yellow solid |
| 1-29 | nd | 325.31 | 326 | 0.80 | Method 2 | Grey powder |
| 1-30 | 209 | 318.33 | 319 | 0.99 | Method 2 | Yellow solid |
| 1-31 | 307-310 | 258.30 | 259 | 0.68 | Method 2 | White solid |
| 1-32 | nd | 328.39 | 329 | 0.60 | Method 2 | White solid |
| 1-33 | 255 | 272.33 | 273 | 0.70 | Method 2 | Beige solid |
| 1-34 | >410 | 272.33 | 273 | 0.73 | Method 2 | White solid |
| 1-35 | nd | 261.28 | 262 | 0.76 | Method 2 | White solid |
| 1-36 | 181-185 | 328.39 | 329 | 1.91 | Method 1 | Beige solid |
| 1-37 | 229-231 | 319.38 | 320 | 1.94 | Method 1 | Yellow solid |
| 1-38 | nd | 258.30 | 259 | 0.47 | Method 2 | Red solid |
| 1-39 | nd | 383.44 | 384 | 0.76 | Method 2 | White solid |
| 1-40 | 190 | 287.34 | 288 | 0.57 | Method 2 | White solid |
| 1-41 | 236-239 | 263.34 | 264 | 0.68 | Method 2 | Yellow solid |
| 1-42 | 277-280 | 249.31 | 250 | 0.53 | Method 2 | White solid |
| 1-43 | 270-280 | 289.33 | 290 | 0.77 | Method 2 | Beige solid |
| 1-44 | 269-271 | 307.32 | 308 | 0.83 | Method 2 | Brown solid |
| 1-45 | 310-313 | 278.72 | 279 | 0.78 | Method 2 | White solid |
| 1-46 | 223-225 | 286.35 | 287 | 0.80 | Method 2 | Beige solid |
| 1-47 | nd | 276.29 | 277 | 0.73 | Method 2 | Brown solid |
| 1-48 | nd | 286.35 | 287 | 0.61 | Method 2 | Brown solid |
| 1-49 | 243 | 292.74 | 293 | 0.86 | Method 2 | Beige solid |
| 1-50 | 196-204 | 263.32 | 264 | 0.39 | Method 2 | White solid |
| 1-51 | nd | 312.27 | 313 | 0.86 | Method 2 | Yellow solid |
| 1-52 | 249-252 | 300.38 | 301 | 0.90 | Method 2 | Beige solid |
| 1-53 | nd | 274.30 | 275 | 0.59 | Method 2 | Brown solid |

TABLE 2-continued

Physico-chemical data for some compounds (nd = not determined).

| Co. Nr | Melting point (° C.) | MW (theor) | [MH+] | RT (min) | LCMS Method | Physical form |
| --- | --- | --- | --- | --- | --- | --- |
| 1-54 | 305-310 | 300.34 | 301 | 0.72 | Method 2 | Brown solid |
| 1-55 | 256 | 262.26 | 263 | 0.69 | Method 2 | Brown solid |
| 1-56 | nd | 301.37 | 302 | 0.64 | Method 2 | Beige solid |
| 1-57 | 256 | 341.43 | 342 | 0.76 | Method 2 | White solid |
| 1-58 | nd | 326.30 | 328 | 0.92 | Method 2 | White solid |
| 1-59 | 311-312 | 244.27 | 245 | 0.61 | Method 2 | Beige solid |
| 1-60 | 260 | 343.40 | 344 | 0.73 | Method 2 | Beige solid |
| 1-61 | 180 | 328.39 | 329 | 0.60 | Method 2 | Beige solid |
| 1-62 | 228-231 | 298.37 | 299 | 0.78 | Method 2 | Beige solid |
| 1-63 | 226-227 | 362.41 | 363 | 0.83 | Method 2 | Yellow solid |
| 1-64 | nd | 329.42 | 330 | 0.66 | Method 2 | White solid |
| 1-65 | nd | 287.34 | 288 | 0.56 | Method 2 | Beige solid |
| 1-66 | 244 | 312.35 | 313 | 0.73 | Method 2 | Yellow solid |
| 1-67 | 287 | 286.31 | 287 | 0.66 | Method 2 | White solid |
| 1-68 | nd | 331.39 | 332 | 0.71 | Method 2 | White solid |
| 1-69 | nd | 276.29 | 277 | 0.75 | Method 2 | White solid |
| 1-70 | nd | 290.32 | 291 | 0.79 | Method 2 | White solid |
| 1-71 | nd | 301.37 | 302 | 0.57 | Method 2 | Beige solid |
| 1-72 | nd | 273.32 | 274 | 0.56 | Method 2 | Beige solid |
| 1-73 | nd | 338.36 | 339 | 0.85 | Method 2 | White solid |
| 1-74 | nd | 288.33 | 289 | 0.64 | Method 2 | White solid |
| 1-75 | nd | 298.36 | 299 | 0.81 | Method 2 | Orange solid |
| 1-76 | nd | 313.38 | 314 | 0.60 | Method 2 | White solid |
| 1-77 | nd | 331.39 | 332 | 0.60 | Method 2 | Beige solid |
| 1-78 | nd | 327.41 | 328 | 0.67 | Method 2 | Beige solid |
| 1-79 | nd | 334.40 | 335 | 0.90 | Method 2 | Yellow solid |
| 1-80 | nd | 288.33 | 289 | 0.64 | Method 2 | White solid |
| 1-81 | nd | 302.35 | 303 | 0.70 | Method 2 | White solid |
| 1-82 | nd | 301.37 | 302 | 0.69 | Method 2 | Beige solid |
| 1-83 | nd | 316.38 | 317 | 0.73 | Method 2 | Yellow solid |

Pharmacology

The compounds provided in the present invention are positive allosteric modulators of mGluR4. As such, these compounds do not appear to bind to the orthosteric glutamate recognition site, and do not activate the mGluR4 by themselves. Instead, the response of mGluR4 to a concentration of glutamate or mGluR4 agonist is increased when compounds of Formula I are present. Compounds of Formula I are expected to have their effect at mGluR4 by virtue of their ability to enhance the function of the receptor.

mGluR4 Assay on HEK-Expressing Human mGluR4

The compounds of the present invention are positive allosteric modulators of mGluR4 receptor. Their activity was examined on recombinant human mGluR4a receptors by detecting changes in intracellular $Ca^{2+}$ concentration, using the fluorescent $Ca^{2+}$-sensitive dye Fluo-4-(AM) and a Fluorometric Imaging Plate Reader (FLIPR, Molecular Devices, Sunnyvale, Calif.).

Transfection and Cell Culture

The cDNA encoding the human metabotropic glutamate receptor (hmGluR4), (accession number NM_000841.1, NCBI Nucleotide database browser), was subcloned into an expression vector containing also the hygromycin resistance gene. In parallel, the cDNA encoding a G protein allowing redirection of the activation signal to intracellular calcium flux was subcloned into a different expression vector containing also the puromycin resistance gene. Transfection of both these vectors into HEK293 cells with PolyFect reagent (Qiagen) according to supplier's protocol, and hygromycin and puromycin treatment allowed selection of antibiotic resistant cells which had integrated stably one or more copies of the plasmids. Positive cellular clones expressing hmGluR4 were identified in a functional assay measuring changes in calcium fluxes in response to glutamate or selective known mGluR4 orthosteric agonists and antagonists.

HEK-293 cells expressing hmGluR4 were maintained in media containing DMEM, dialyzed Fetal Calf Serum (10%), Glutamax™ (2 mM), Penicillin (100 units/mL), Streptomycin (100 µg/mL), Geneticin (100 µg/mL) and Hygromycin-B (40 µg/mL) and puromycin (1 µg/mL) at 37° C./5% $CO_2$.

Fluorescent Cell Based-$Ca^{2+}$ Mobilization Assay

Human mGluR4 HEK-293 cells were plated out 24 hours prior to FLIPR[384] assay in black-walled, clear-bottomed, poly-L-ornithine-coated 384-well plates at a density of 25,000 cells/well in a glutamine/glutamate free DMEM medium containing foetal bovine serum (10%), penicillin (100 units/mL) and streptomycin (100 µg/mL) at 37° C./5% $CO_2$.

On the day of the assay, the medium was aspirated and the cells were loaded with a 3 µM solution of Fluo4-AM (LuBioScience, Lucerne, Switzerland) in 0.03% pluronic acid. After 1 hour at 37° C./5% $CO_2$, the non incorporated dye was removed by washing cell plate with the assay buffer and the cells were left in the dark at room temperature for six hours before testing. All assays were performed in a pH 7.4 buffered-solution containing 20 mM HEPES, 143 mM NaCl, 6 mM KCl, 1 mM $MgSO_4$, 1 mM $CaCl_2$, 0.125 mM sulfapyrazone and 0.1% glucose.

After 10 s of basal fluorescence recording, various concentrations of the compounds of the invention were added to the cells. Changes in fluorescence levels were first monitored for 180 s in order to detect any agonist activity of the compounds. Then the cells were stimulated by an $EC_{25}$ glutamate concentration for an additional 110 s in order to measure enhancing activities of the compounds of the invention. $EC_{25}$ glutamate concentration is the concentration giving 25% of the maximal glutamate response.

The concentration-response curves of representative compounds of the present invention were generated using the Prism GraphPad software (Graph Pad Inc, San Diego, USA). The curves were fitted to a four-parameter logistic equation:

$$Y = Bottom + (Top - Bottom)/(1 + 10\hat{}((\log EC_{50} - X) * Hill\ Slope))$$

allowing the determination of $EC_{50}$ values.

The Table 3 below represents the mean $EC_{50}$ obtained from at least three independent experiments of selected molecules performed in duplicate.

TABLE 3

Activity data for selected compounds

| Compound no. | $Ca^{2+}$ Flux* |
|---|---|
| 1-1 | ++ |
| 1-6 | ++ |
| 1-8 | + |
| 1-10 | +++ |
| 1-16 | +++ |
| 1-17 | +++ |
| 1-18 | ++ |
| 1-21 | + |
| 1-26 | ++ |
| 1-27 | + |
| 1-61 | + |
| 1-65 | + |

*Table legend:
(+): 1 µM < $EC_{50}$ < 10 µM
(++): 100 nM < $EC_{50}$ 1 µM
(+++): $EC_{50}$ < 100 nM The results shown in Table 3 demonstrate that the compounds described in the present invention are positive allosteric modulators of human mGluR4 receptors. These compounds do not have activity by themselves but they rather increase the functional activity and/or maximal efficacy of glutamate or mGluR4 agonist.

Thus, the positive allosteric modulators provided in the present invention are expected to increase the effectiveness of glutamate or mGluR4 agonists at mGluR4 receptor. Therefore, these positive allosteric modulators are expected to be useful for treatment of various neurological and psychiatric disorders associated with glutamate dysfunction described to be treated herein and others that can be treated by such positive allosteric modulators.

The compounds of the invention can be administered either alone, or in combination with other pharmaceutical agents effective in the treatment of conditions mentioned above.

FORMULATION EXAMPLES

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced by the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 mL.

3. Injectable

A parenteral composition is prepared by stirring 1.5% by weight of active ingredient of the invention in 10% by volume propylene glycol and water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:
1. A compound having the Formula (I):

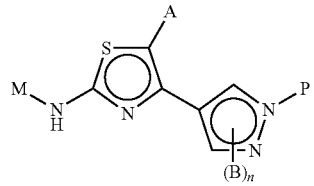

a pharmaceutically acceptable acid or base addition salt thereof, a stereochemically isomeric form thereof and an N-oxide form thereof, wherein:

A radical is selected from the group of hydrogen, halogen, —CN, —OH, —$CF_3$, —SH, —$NH_2$ and an optionally substituted radical selected from the group of —($C_1$-$C_6$)alkyl, —($C_1$-$C_6$)haloalkyl, —($C_3$-$C_7$)cycloalkyl, —($C_1$-$C_6$)cyanoalkyl, —($C_1$-$C_6$)alkylene-heteroaryl, —($C_1$-$C_6$)alkylene-aryl, aryl, heteroaryl, heterocycle, —($C_0$-$C_6$)alkyl-$OR^1$, —O—($C_2$-$C_6$)alkylene-$OR^1$, —$NR^1$($C_2$-$C_6$)alkylene-$OR^2$, —($C_3$-$C_7$)cycloalkyl-($C_1$-$C_6$)alkyl, —O—($C_3$-$C_7$)cycloalkyl-($C_1$-$C_6$)alkyl, —$NR^1$—($C_3$-$C_7$)cycloalkyl-($C_1$-$C_6$)alkyl, —($C_1$-$C_6$)haloalkylene-$OR^1$, —($C_1$-$C_6$)haloalkylene-$NR^1R^2$, —($C_0$-$C_6$)alkyl-S—$R^1$, —O—($C_2$-$C_6$)alkylene-S—$R^1$, —$NR^1$—($C_2$-$C_6$)alkylene-S—$R^2$, —($C_0$-$C_6$)alkyl-S(=O)—$R^1$, —O—($C_1$-$C_6$)alkylene-S(=O)—$R^1$, —$NR^1$—($C_1$-$C_6$)alkylene-S(=O)—$R^2$, —($C_0$-$C_6$)alkyl-S(=O)$_2$—$R^1$, —O—($C_1$-$C_6$)alkylene-S(=O)$_2$—$R^1$, —$NR^1$—($C_1$-$C_6$)alkylene-S(=O)$_2$—$R^2$, —($C_0$-$C_6$)alkyl-$NR^1R^2$, —O—($C_2$-$C_6$)alkylene-$NR^1R^2$, —$NR^1$—($C_2$-$C_6$)alkylene-$NR^2R^3$, —($C_0$-$C_6$)alkyl-S(=O)$_2$$NR^1R^2$, —O—($C_1$-$C_6$)alkylene-S(=O)$_2$$NR^1R^2$, —$NR^1$—($C_1$-$C_6$)alkylene-S(=O)$_2$$NR^2R^3$, —($C_0$-$C_6$)alkyl-$NR^1$—S(=O)$_2$$R^2$, —O—($C_2$-$C_6$)alkylene-$NR^1$—S(=O)$_2$$R^2$, —$NR^1$—($C_2$-$C_6$)alkylene-$NR^2$—S(=O)$_2$$R^3$, —($C_0$-$C_6$)alkyl-C(=O)—$NR^1R^2$, —O—($C_1$-$C_6$)alkylene-C(=O)—$NR^1R^2$, —$NR^1$—($C_1$-$C_6$)alkylene-C(=O)—$NR^2R^3$, —($C_0$-$C_6$)alkyl-$NR^1$C(=O)—$R^2$, —O—($C_2$-$C_6$)alkylene-$NR^1$C(=O)—$R^2$, —$NR^1$—($C_2$-$C_6$)alkylene-$NR^2$C(=O)—$R^3$, —($C_0$-$C_6$)alkyl-C(=O)—$R^1$, —O—($C_1$-$C_6$)alkylene-C(=O)—$R^1$, —$NR^1$—($C_1$-$C_6$)alkylene-C(=O)—$R^2$, —($C_0$-$C_6$)alkyl-$NR^1$—C(=O)—$NR^2R^3$, —O—($C_2$-$C_6$)alkylene-$NR^1$—C(=O)—$NR^2R^3$ and —$NR^1$—($C_2$-$C_6$)alkylene-$NR^2$—C(=O)—$NR^3R^4$;

$R^1$, $R^2$, $R^3$ and $R^4$ are each independently hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl;

Any two radicals of $R^1$, $R^2$, $R^3$ or $R^4$ may be taken together to form an optionally substituted 3 to 10 membered carbocyclic or heterocyclic ring;

n is an integer ranging from 1 to 2;

B radicals are each independently selected from the group of hydrogen, halogen, —CN, —OH, —$CF_3$, —SH, —$NH_2$ and an optionally substituted radical selected from the group of —($C_1$-$C_6$)alkyl, —($C_1$-$C_6$)haloalkyl, —($C_3$-$C_7$)cycloalkyl, —($C_1$-$C_6$)cyanoalkyl, —($C_1$-$C_6$)alkylene-heteroaryl, —($C_1$-$C_6$)alkylene-aryl, aryl, heteroaryl, heterocycle, —($C_0$-$C_6$)alkyl-$OR^5$, —O—($C_2$-$C_6$)alkylene-$OR^5$, —$NR^5$($C_2$-$C_6$)alkylene-$OR^6$, —($C_3$-$C_7$)cycloalkyl-($C_1$-$C_6$)alkyl, —O—($C_3$-$C_7$)cycloalkyl-($C_1$-$C_6$)alkyl, —$NR^5$—($C_3$-$C_7$)cycloalkyl-($C_1$-$C_6$)alkyl, —($C_1$-$C_6$)haloalkylene-$OR^5$, —($C_1$-$C_6$)haloalkylene-$NR^5R^6$, —($C_0$-$C_6$)alkyl-S—$R^5$, —O—($C_2$-$C_6$)alkylene-S—$R^5$, —$NR^5$—($C_2$-$C_6$)alkylene-S—$R^6$, —($C_0$-$C_6$)alkyl-S(=O)—$R^5$, —O—($C_1$-$C_6$)alkylene-S(=O)—$R^5$, —$NR^5$—($C_1$-$C_6$)alkylene-S(=O)—$R^6$, —($C_0$-$C_6$)alkyl-S(=O)$_2$—$R^5$, —O—($C_1$-$C_6$)alkylene-S(=O)$_2$—$R^5$, —$NR^5$—($C_1$-$C_6$)alkylene-S(=O)$_2$—$R^6$, —($C_0$-$C_6$)alkyl-$NR^5R^6$, —O—($C_2$-$C_6$)alkylene-$NR^5R^6$, —$NR^5$($C_2$-$C_6$)alkylene-$NR^6R^7$, —($C_0$-$C_6$)alkyl-S(=O)$_2$$NR^5R^6$, —O—($C_1$-$C_6$)alkylene-S(=O)$_2$$NR^5R^6$, —$NR^5$—($C_1$-$C_6$)alkylene-S(=O)$_2$$NR^6R^7$, —($C_0$-$C_6$)alkyl-$NR^5$—S(=O)$_2$$R^6$, —O—($C_2$-$C_6$)alkylene-$NR^5$—S(=O)$_2$$R^6$, —$NR^5$—($C_2$-$C_6$)alkylene-$NR^6$—S(=O)$_2$$R^7$, —($C_0$-$C_6$)alkyl-C(=O)—$NR^5R^6$, —O—($C_1$-$C_6$)alkylene-C(=O)—$NR^5R^6$, —$NR^5$—($C_1$-$C_6$)alkylene-C(=O)—$NR^6R^7$, —($C_0$-$C_6$)alkyl-$NR^5$C(=O)—$R^6$, —O—($C_2$-$C_6$)alkylene-$NR^5$C(=O)—$R^6$, —$NR^5$—($C_2$-$C_6$)alkylene-$NR^6$C(=O)—$R^7$, —($C_0$-$C_6$)alkyl-C(=O)—$R^5$, —O—($C_1$-$C_6$)alkylene-C(=O)—$R^5$, —$NR^5$—($C_1$-$C_6$)alkylene-C(=O)—$R^6$, —($C_0$-$C_6$)alkyl-$NR^5$—C(=O)—$NR^6R^7$, —O—($C_2$-$C_6$)alkylene-$NR^5$—C(=O)—$NR^6R^7$ and —$NR^5$—($C_2$-$C_6$)alkylene-$NR^6$—C(=O)—$NR^7R^8$;

$R^5$, $R^6$, $R^7$ and $R^8$ are each independently hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl;

M is selected from an optionally substituted 3 to 10 membered ring selected from the group of aryl, heteroaryl, heterocyclic and cycloalkyl;

P is selected from the group of a hydrogen or an optionally substituted radical selected from the group of —($C_0$-$C_6$)alkyl-C(=O)—$R^9$, —($C_1$-$C_6$)alkyl-CN, —($C_2$-$C_6$)alkyl-S(O)—$R^9$, —($C_0$-$C_6$)alkyl-C(=O)$NR^9R^{10}$, —($C_2$-$C_6$)alkyl-$NR^9$C(=O)$R^{10}$ and —($C_0$-$C_6$)alkyl-S(O)$_2$—$R^9$; and $R^9$ and $R^{10}$ are selected from the group of a hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl;

with the proviso (i) that:
  when P is H, A is H, n is 1 and B is —CN then M can not be an aryl substituted by octyloxy; and with the proviso that the compound is not:
4-(3-Methyl-1H-pyrazol-4-yl)-N-phenylthiazol-2-amine;
4-(3-Methyl-1H-pyrazol-4-yl)-N-(pyridin-2-yl)thiazol-2-amine;
N-(Pyridin-2-yl)-4-(3-(trifluoromethyl)-1H-pyrazol-4-yl)thiazol-2-amine;
4-(3-Isopropyl-1H-pyrazol-4-yl)-N-(pyridin-2-yl)thiazol-2-amine;
N-(2,6-Difluorophenyl)-4-(3-methyl-1H-pyrazol-4-yl)thiazol-2-amine;
5-Methyl-4-(3-methyl-1H-pyrazol-4-yl)-N-(pyridin-2-yl)thiazol-2-amine;
5-Methyl-4-(1H-pyrazol-4-yl)-N-(pyridin-2-yl)thiazol-2-amine;
N-(2,5-Difluorophenyl)-4-(3-methyl-1H-pyrazol-4-yl)thiazol-2-amine;

5-Methyl-N-(6-methylpyridin-2-yl)-4-(1H-pyrazol-4-yl)thiazol-2-amine;
5-Methyl-N-(4-methylpyridin-2-yl)-4-(1H-pyrazol-4-yl)thiazol-2-amine;
N-(3,5-Difluoropyridin-2-yl)-5-methyl-4-(1H-pyrazol-4-yl)thiazol-2-amine;
4-(3-Methyl-1H-pyrazol-4-yl)-N-(4-methylpyridin-2-yl)thiazol-2-amine;
5-Ethyl-4-(1H-pyrazol-4-yl)-N-(pyridin-2-yl)thiazol-2-amine;
4-(3-Methyl-1H-pyrazol-4-yl)-N-(6-methylpyridin-2-yl)thiazol-2-amine;
N-(5-Fluoropyridin-2-yl)-5-methyl-4-(1H-pyrazol-4-yl)thiazol-2-amine;
4-(1H-Pyrazol-4-yl)-N-(pyridin-2-yl)thiazol-2-amine;
2-Methyl-1-(4-(5-methyl-2-(pyridin-2-ylamino)thiazol-4-yl)-1H-pyrazol-1-yl)propan-1-one;
4-(5-Methyl-2-(pyridin-2-ylamino)thiazol-4-yl)-1H-pyrazole-1-carboxamide;
Cyclohexyl(4-(5-methyl-2-(pyridin-2-ylamino)thiazol-4-yl)-1H-pyrazol-1-yl)methanone;
N-Cyclohexyl-5-methyl-4-(1H-pyrazol-4-yl)thiazol-2-amine;
2-Methyl-1-(4-(5-methyl-2-(6-methylpyridin-2-ylamino)thiazol-4-yl)-1H-pyrazol-1-yl)propan-1-one;
N-(6-Chloropyridin-2-yl)-5-methyl-4-(1H-pyrazol-4-yl)thiazol-2-amine;
5-Chloro-4-(1H-pyrazol-4-yl)-N-(pyridin-2-yl)thiazol-2-amine;
N-(6-Fluoropyridin-2-yl)-5-methyl-4-(1H-pyrazol-4-yl)thiazol-2-amine;
(4-(5-Methyl-2-(pyridin-2-ylamino)thiazol-4-yl)-1H-pyrazol-1-yl)(piperidin-1-yl)methanone;
N-Cyclopentyl-5-methyl-4-(1H-pyrazol-4-yl)thiazol-2-amine;
5-Methyl-N-(pyrazin-2-yl)-4-(1H-pyrazol-4-yl)thiazol-2-amine;
5-Methyl-4-(1-(methylsulfonyl)-1H-pyrazol-4-yl)-N-(pyridin-2-yl)thiazol-2-amine;
N-(3-Fluoropyridin-2-yl)-5-methyl-4-(1H-pyrazol-4-yl)thiazol-2-amine;
4-(1H-Pyrazol-4-yl)-2-(pyridin-2-ylamino)thiazol-5-carbonitrile;
N-(6-Ethylpyridin-2-yl)-5-methyl-4-(1H-pyrazol-4-yl)thiazol-2-amine;
N-(6-Chloropyridin-2-yl)-4-(1H-pyrazol-4-yl)thiazol-2-amine;
N-Isopropyl-4-(5-methyl-2-(pyridin-2-ylamino)thiazol-4-yl)-1H-pyrazole-1-carboxamide;
N-(6-Fluoropyridin-2-yl)-4-(1H-pyrazol-4-yl)thiazol-2-amine;
5-Chloro-N-(6-methylpyridin-2-yl)-4-(1H-pyrazol-4-yl)thiazol-2-amine;
N-(6-Methylpyridin-2-yl)-4-(1H-pyrazol-4-yl)thiazol-2-amine;
4-(1H-Pyrazol-4-yl)-N-(pyridin-2-yl)-5-(trifluoromethyl)thiazol-2-amine;
5-Phenyl-4-(1H-pyrazol-4-yl)-N-(pyridin-2-yl)thiazol-2-amine;
5-Fluoro-4-(1H-pyrazol-4-yl)-N-(pyridin-2-yl)thiazol-2-amine;
(4-(1H-Pyrazol-4-yl)-2-(pyridin-2-ylamino)thiazol-5-yl)methanol;
N-(6-Methoxypyridin-2-yl)-5-methyl-4-(1H-pyrazol-4-yl)thiazol-2-amine;
N-Cyclopropyl-4-(5-methyl-2-(pyridin-2-ylamino)thiazol-4-yl)-1H-pyrazole-1-carboxamide;
4-(3-Cyclopropyl-1H-pyrazol-4-yl)-N-(pyridin-2-yl)thiazol-2-amine;
4-(3-Ethyl-1H-pyrazol-4-yl)-N-(pyridin-2-yl)thiazol-2-amine; and
4-(2-(6-Fluoropyridin-2-ylamino)-5-methylthiazol-4-yl)-1H-pyrazole-1-carboxamide.

2. A compound according to claim 1 having the Formula (I) wherein:
M is an optionally substituted pyridyl ring;
with the proviso that the compound is not:
4-(3-Methyl-1H-pyrazol-4-yl)-N-(pyridin-2-yl)thiazol-2-amine;
N-(Pyridin-2-yl)-4-(3-(trifluoromethyl)-1H-pyrazol-4-yl)thiazol-2-amine;
4-(3-Isopropyl-1H-pyrazol-4-yl)-N-(pyridin-2-yl)thiazol-2-amine;
5-Methyl-4-(3-methyl-1H-pyrazol-4-yl)-N-(pyridin-2-yl)thiazol-2-amine;
5-Methyl-4-(1H-pyrazol-4-yl)-N-(pyridin-2-yl)thiazol-2-amine;
5-Methyl-N-(6-methylpyridin-2-yl)-4-(1H-pyrazol-4-yl)thiazol-2-amine;
5-Methyl-N-(4-methylpyridin-2-yl)-4-(1H-pyrazol-4-yl)thiazol-2-amine;
N-(3,5-Difluoropyridin-2-yl)-5-methyl-4-(1H-pyrazol-4-yl)thiazol-2-amine;
4-(3-Methyl-1H-pyrazol-4-yl)-N-(4-methylpyridin-2-yl)thiazol-2-amine;
5-Ethyl-4-(1H-pyrazol-4-yl)-N-(pyridin-2-yl)thiazol-2-amine;
4-(3-Methyl-1H-pyrazol-4-yl)-N-(6-methylpyridin-2-yl)thiazol-2-amine;
N-(5-Fluoropyridin-2-yl)-5-methyl-4-(1H-pyrazol-4-yl)thiazol-2-amine;
4-(1H-Pyrazol-4-yl)-N-(pyridin-2-yl)thiazol-2-amine;
2-Methyl-1-(4-(5-methyl-2-(pyridin-2-ylamino)thiazol-4-yl)-1H-pyrazol-1-yl)propan-1-one;
4-(5-Methyl-2-(pyridin-2-ylamino)thiazol-4-yl)-1H-pyrazole-1-carboxamide;
Cyclohexyl(4-(5-methyl-2-(pyridin-2-ylamino)thiazol-4-yl)-1H-pyrazol-1-yl)methanone;
2-Methyl-1-(4-(5-methyl-2-(6-methylpyridin-2-ylamino)thiazol-4-yl)-1H-pyrazol-1-yl)propan-1-one;
N-(6-Chloropyridin-2-yl)-5-methyl-4-(1H-pyrazol-4-yl)thiazol-2-amine;
5-Chloro-4-(1H-pyrazol-4-yl)-N-(pyridin-2-yl)thiazol-2-amine;
N-(6-Fluoropyridin-2-yl)-5-methyl-4-(1H-pyrazol-4-yl)thiazol-2-amine;
(4-(5-Methyl-2-(pyridin-2-ylamino)thiazol-4-yl)-1H-pyrazol-1-yl)(piperidin-1-yl)methanone;
5-Methyl-4-(1-(methylsulfonyl)-1H-pyrazol-4-yl)-N-(pyridin-2-yl)thiazol-2-amine;
N-(3-Fluoropyridin-2-yl)-5-methyl-4-(1H-pyrazol-4-yl)thiazol-2-amine;
4-(1H-Pyrazol-4-yl)-2-(pyridin-2-ylamino)thiazol-5-carbonitrile;
N-(6-Ethylpyridin-2-yl)-5-methyl-4-(1H-pyrazol-4-yl)thiazol-2-amine;
N-(6-Chloropyridin-2-yl)-4-(1H-pyrazol-4-yl)thiazol-2-amine;
N-Isopropyl-4-(5-methyl-2-(pyridin-2-ylamino)thiazol-4-yl)-1H-pyrazole-1-carboxamide;
N-(6-Fluoropyridin-2-yl)-4-(1H-pyrazol-4-yl)thiazol-2-amine;
5-Chloro-N-(6-methylpyridin-2-yl)-4-(1H-pyrazol-4-yl)thiazol-2-amine;

N-(6-Methylpyridin-2-yl)-4-(1H-pyrazol-4-yl)thiazol-2-amine;
4-(1H-Pyrazol-4-yl)-N-(pyridin-2-yl)-5-(trifluoromethyl)thiazol-2-amine;
5-Phenyl-4-(1H-pyrazol-4-yl)-N-(pyridin-2-yl)thiazol-2-amine;
5-Fluoro-4-(1H-pyrazol-4-yl)-N-(pyridin-2-yl)thiazol-2-amine;
(4-(1H-Pyrazol-4-yl)-2-(pyridin-2-ylamino)thiazol-5-yl)methanol;
N-(6-Methoxypyridin-2-yl)-5-methyl-4-(1H-pyrazol-4-yl)thiazol-2-amine;
N-Cyclopropyl-4-(5-methyl-2-(pyridin-2-ylamino)thiazol-4-yl)-1H-pyrazole-1-carboxamide;
4-(3-Cyclopropyl-1H-pyrazol-4-yl)-N-(pyridin-2-yl)thiazol-2-amine;
4-(3-Ethyl-1H-pyrazol-4-yl)-N-(pyridin-2-yl)thiazol-2-amine; and
4-(2-(6-Fluoropyridin-2-ylamino)-5-methylthiazol-4-yl)-1H-pyrazole-1-carboxamide.

3. A compound according to claim 2 having the Formula (I) wherein:

A radical is selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^1$, —O—(C$_2$-C$_6$)alkylene-OR$^1$, —NR$^1$(C$_2$-C$_6$)alkylene-OR$^2$, —(C$_3$-C$_7$)cycloalkyl-(C$_1$-C$_6$)alkyl, —O—(C$_3$-C$_7$)cycloalkyl-(C$_1$-C$_6$)alkyl, —NR$^1$—(C$_3$-C$_7$)cycloalkyl-(C$_1$-C$_6$)alkyl, —(C$_1$-C$_6$)haloalkylene-OR$^1$, —(C$_1$-C$_6$)haloalkylene-NR$^1$R$^2$, —(C$_0$-C$_6$)alkyl-NR$^1$R$^2$, —O—(C$_2$-C$_6$)alkylene-NR$^1$R$^2$, —NR$^1$—(C$_2$-C$_6$)alkylene-NR$^2$R$^3$, —(C$_0$-C$_6$)alkyl-C(=O)—NR$^1$R$^2$, —O—(C$_1$-C$_6$)alkylene-C(=O)—NR$^1$R$^2$, —NR$^1$—(C$_1$-C$_6$)alkylene-C(=O)—NR$^2$R$^3$, —(C$_0$-C$_6$)alkyl-NR$^1$C(=O)—R$^2$, —O—(C$_2$-C$_6$)alkylene-NR$^1$C(=O)—R$^2$, —NR$^1$—(C$_2$-C$_6$)alkylene-NR$^2$C(=O)—R$^3$, —(C$_0$-C$_6$)alkyl-S(=O)$_2$—R$^1$, —(C$_0$-C$_6$)alkyl-C(=O)—R$^1$, —O—(C$_1$-C$_6$)alkylene-C(=O)—R$^1$ and —NR$^1$—(C$_1$-C$_6$)alkylene-C(=O)—R$^2$;

R$^1$, R$^2$ and R$^3$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

Any two radicals of R$^1$, R$^2$ or R$^3$ may be taken together to form an optionally substituted 3 to 10 membered carbocyclic or heterocyclic ring;

n is 1;

B radicals are each independently selected from the group of hydrogen, halogen, —CN, —OH, —CF$_3$, —NH$_2$ and an optionally substituted radical selected from the group of —(C$_1$-C$_6$)alkyl, —(C$_1$-C$_6$)haloalkyl, —(C$_3$-C$_7$)cycloalkyl, —(C$_1$-C$_6$)cyanoalkyl, —(C$_1$-C$_6$)alkylene-heteroaryl, —(C$_1$-C$_6$)alkylene-aryl, aryl, heteroaryl, heterocycle, —(C$_0$-C$_6$)alkyl-OR$^5$, —O—(C$_2$-C$_6$)alkylene-OR$^5$, —NR$^5$(C$_2$-C$_6$)alkylene-OR$^6$, —(C$_3$-C$_7$)cycloalkyl-(C$_1$-C$_6$)alkyl, —O—(C$_3$-C$_7$)cycloalkyl-(C$_1$-C$_6$)alkyl, —NR$^5$—(C$_3$-C$_7$)cycloalkyl-(C$_1$-C$_6$)alkyl, —(C$_1$-C$_6$)haloalkylene-OR$^5$, —(C$_1$-C$_6$)haloalkylene-NR$^5$R$^6$, —(C$_0$-C$_6$)alkyl-NR$^5$R$^6$, —O—(C$_2$-C$_6$)alkylene-NR$^5$R$^6$, —NR$^5$—(C$_2$-C$_6$)alkylene-NR$^6$R$^7$, —(C$_0$-C$_6$)alkyl-C(=O)—NR$^5$R$^6$, —O—(C$_1$-C$_6$)alkylene-C(=O)—NR$^5$R$^6$, —NR$^5$—(C$_1$-C$_6$)alkylene-C(=O)—NR$^6$R$^7$, —(C$_0$-C$_6$)alkyl-NR$^5$C(=O)—R$^6$, —O—(C$_2$-C$_6$)alkylene-NR$^5$C(=O)—R$^6$, —NR$^5$—(C$_2$-C$_6$)alkylene-NR$^6$C(=O)—R$^7$, —(C$_0$-C$_6$)alkyl-S(=O)$_2$—R$^5$, —(C$_0$-C$_6$)alkyl-C(=O)—R$^5$, —O—(C$_1$-C$_6$)alkylene-C(=O)—R$^5$ and —NR$^5$—(C$_1$-C$_6$)alkylene-C(=O)—R$^6$;

R$^5$, R$^6$ and R$^7$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

M is an optionally substituted pyridyl ring;

P is selected from the group of a hydrogen or an optionally substituted radical selected from the group of —(C$_0$-C$_6$)alkyl-C(=O)—R$^9$, —(C$_1$-C$_6$)alkyl-CN, —(C$_2$-C$_6$)alkyl-S(O)—R$^9$, —(C$_0$-C$_6$)alkyl-C(=O)NR$^9$R$^{10}$, —(C$_2$-C$_6$)alkyl-NR$^9$C(=O)R$^{10}$ and —(C$_0$-C$_6$)alkyl-S(O)$_2$—R$^9$; and R$^9$ and R$^{10}$ are selected from the group of a hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

with the proviso that the compound is not:

4-(3-Methyl-1H-pyrazol-4-yl)-N-(pyridin-2-yl)thiazol-2-amine;
N-(Pyridin-2-yl)-4-(3-(trifluoromethyl)-1H-pyrazol-4-yl)thiazol-2-amine;
4-(3-Isopropyl-1H-pyrazol-4-yl)-N-(pyridin-2-yl)thiazol-2-amine;
5-Methyl-4-(3-methyl-1H-pyrazol-4-yl)-N-(pyridin-2-yl)thiazol-2-amine;
5-Methyl-4-(1H-pyrazol-4-yl)-N-(pyridin-2-yl)thiazol-2-amine;
5-Methyl-N-(6-methylpyridin-2-yl)-4-(1H-pyrazol-4-yl)thiazol-2-amine;
5-Methyl-N-(4-methylpyridin-2-yl)-4-(1H-pyrazol-4-yl)thiazol-2-amine;
N-(3,5-Difluoropyridin-2-yl)-5-methyl-4-(1H-pyrazol-4-yl)thiazol-2-amine;
4-(3-Methyl-1H-pyrazol-4-yl)-N-(4-methylpyridin-2-yl)thiazol-2-amine;
5-Ethyl-4-(1H-pyrazol-4-yl)-N-(pyridin-2-yl)thiazol-2-amine;
4-(3-Methyl-1H-pyrazol-4-yl)-N-(6-methylpyridin-2-yl)thiazol-2-amine;
N-(5-Fluoropyridin-2-yl)-5-methyl-4-(1H-pyrazol-4-yl)thiazol-2-amine;
4-(1H-Pyrazol-4-yl)-N-(pyridin-2-yl)thiazol-2-amine;
2-Methyl-1-(4-(5-methyl-2-(pyridin-2-ylamino)thiazol-4-yl)-1H-pyrazol-1-yl)propan-1-one;
4-(5-Methyl-2-(pyridin-2-ylamino)thiazol-4-yl)-1H-pyrazole-1-carboxamide;
Cyclohexyl(4-(5-methyl-2-(pyridin-2-ylamino)thiazol-4-yl)-1H-pyrazol-1-yl)methanone;
2-Methyl-1-(4-(5-methyl-2-(6-methylpyridin-2-ylamino)thiazol-4-yl)-1H-pyrazol-1-yl)propan-1-one;
N-(6-Chloropyridin-2-yl)-5-methyl-4-(1H-pyrazol-4-yl)thiazol-2-amine;
5-Chloro-4-(1H-pyrazol-4-yl)-N-(pyridin-2-yl)thiazol-2-amine;
N-(6-Fluoropyridin-2-yl)-5-methyl-4-(1H-pyrazol-4-yl)thiazol-2-amine;
(4-(5-Methyl-2-(pyridin-2-ylamino)thiazol-4-yl)-1H-pyrazol-1-yl)(piperidin-1-yl)methanone;

5-Methyl-4-(1-(methylsulfonyl)-1H-pyrazol-4-yl)-N-(pyridin-2-yl)thiazol-2-amine;
N-(3-Fluoropyridin-2-yl)-5-methyl-4-(1H-pyrazol-4-yl)thiazol-2-amine;
4-(1H-Pyrazol-4-yl)-2-(pyridin-2-ylamino)thiazol-5-carbonitrile;
N-(6-Ethylpyridin-2-yl)-5-methyl-4-(1H-pyrazol-4-yl)thiazol-2-amine;
N-(6-Chloropyridin-2-yl)-4-(1H-pyrazol-4-yl)thiazol-2-amine;
N-Isopropyl-4-(5-methyl-2-(pyridin-2-ylamino)thiazol-4-yl)-1H-pyrazole-1-carboxamide;
N-(6-Fluoropyridin-2-yl)-4-(1H-pyrazol-4-yl)thiazol-2-amine;
5-Chloro-N-(6-methylpyridin-2-yl)-4-(1H-pyrazol-4-yl)thiazol-2-amine;
N-(6-Methylpyridin-2-yl)-4-(1H-pyrazol-4-yl)thiazol-2-amine;
4-(1H-Pyrazol-4-yl)-N-(pyridin-2-yl)-5-(trifluoromethyl)thiazol-2-amine;
5-Phenyl-4-(1H-pyrazol-4-yl)-N-(pyridin-2-yl)thiazol-2-amine;
5-Fluoro-4-(1H-pyrazol-4-yl)-N-(pyridin-2-yl)thiazol-2-amine;
(4-(1H-Pyrazol-4-yl)-2-(pyridin-2-ylamino)thiazol-5-yl)methano;
N-(6-Methoxypyridin-2-yl)-5-methyl-4-(1H-pyrazol-4-yl)thiazol-2-amine;
N-Cyclopropyl-4-(5-methyl-2-(pyridin-2-ylamino)thiazol-4-yl)-1H-pyrazole-1-carboxamide;
4-(3-Cyclopropyl-1H-pyrazol-4-yl)-N-(pyridin-2-yl)thiazol-2-amine;
4-(3-Ethyl-1H-pyrazol-4-yl)-N-(pyridin-2-yl)thiazol-2-amine; and
4-(2-(6-Fluoropyridin-2-ylamino)-5-methylthiazol-4-yl)-1H-pyrazole-1-carboxamide.

4. A compound according to claim 1 having the Formula (I) wherein:
M is an optionally substituted pyrimidyl ring.

5. A compound according to claim 4 having the Formula (I) wherein:
A radical is selected from the group of hydrogen, halogen, —CN, —OH, —CF$_3$, —NH$_2$ and an optionally substituted radical selected from the group of —($C_1$-$C_6$)alkyl, —($C_1$-$C_6$)haloalkyl, —($C_3$-$C_7$)cycloalkyl, —($C_1$-$C_6$)cyanoalkyl, —($C_1$-$C_6$)alkylene-heteroaryl, —($C_1$-$C_6$)alkylene-aryl, aryl, heteroaryl, heterocycle, —($C_0$-$C_6$)alkyl-OR$^1$, —O—($C_2$-$C_6$)alkylene-OR$^1$, —NR$^1$($C_2$-$C_6$)alkylene-OR$^2$, —($C_3$-$C_7$)cycloalkyl-($C_1$-$C_6$)alkyl, —O—($C_3$-$C_7$)cycloalkyl-($C_1$-$C_6$)alkyl, —NR$^1$—($C_3$-$C_7$)cycloalkyl-($C_1$-$C_6$)alkyl, —($C_1$-$C_6$)haloalkylene-OR$^1$, —($C_1$-$C_6$)haloalkylene-NR$^1$R$^2$, —($C_0$-$C_6$)alkyl-NR$^1$R$^2$, —O—($C_2$-$C_6$)alkylene-NR$^1$R$^2$, —NR$^1$—($C_2$-$C_6$)alkylene-NR$^2$R$^3$, —($C_0$-$C_6$)alkyl-C(=O)—NR$^1$R$^2$, —O—($C_1$-$C_6$)alkylene-C(=O)—NR$^1$R$^2$, —NR$^1$—($C_1$-$C_6$)alkylene-C(=O)—NR$^2$R$^3$, —($C_0$-$C_6$)alkyl-NR$^1$C(=O)—R$^2$, —O—($C_2$-$C_6$)alkylene-NR$^1$C(=O)—R$^2$, —NR$^1$—($C_2$-$C_6$)alkylene-NR$^2$C(=O)—R$^3$, —($C_0$-$C_6$)alkyl-S(=O)$_2$—R$^1$, —($C_0$-$C_6$)alkyl-C(=O)—R$^1$, —O—($C_1$-$C_6$)alkylene-C(=O)—R$^1$ and —NR$^1$—($C_1$-$C_6$)alkylene-C(=O)—R$^2$;
R$^1$, R$^2$ and R$^3$ are each independently hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl;

Any two radicals of R$^1$, R$^2$ or R$^3$ may be taken together to form an optionally substituted 3 to 10 membered carbocyclic or heterocyclic ring;
n is 1;
B radicals are each independently selected from the group of hydrogen, halogen, —CN, —OH, —CF$_3$, —NH$_2$ and an optionally substituted radical selected from the group of —($C_1$-$C_6$)alkyl, —($C_1$-$C_6$)haloalkyl, —($C_3$-$C_7$)cycloalkyl, —($C_1$-$C_6$)cyanoalkyl, —($C_1$-$C_6$)alkylene-heteroaryl, —($C_1$-$C_6$)alkylene-aryl, aryl, heteroaryl, heterocycle, —($C_0$-$C_6$)alkyl-OR$^5$, —O—($C_2$-$C_6$)alkylene-OR$^5$, —NR$^5$($C_2$-$C_6$)alkylene-OR$^6$, —($C_3$-$C_7$)cycloalkyl-($C_1$-$C_6$)alkyl, —O—($C_3$-$C_7$)cycloalkyl-($C_1$-$C_6$)alkyl, —NR$^5$—($C_3$-$C_7$)cycloalkyl-($C_1$-$C_6$)alkyl, —($C_1$-$C_6$)haloalkylene-OR$^5$, —($C_1$-$C_6$)haloalkylene-NR$^5$R$^6$, —($C_0$-$C_6$)alkyl-NR$^5$R$^6$, —O—($C_2$-$C_6$)alkylene-NR$^5$R$^6$, —NR$^5$—($C_2$-$C_6$)alkylene-NR$^6$R$^7$, —($C_0$-$C_6$)alkyl-C(=O)—NR$^5$R$^6$, —O—($C_1$-$C_6$)alkylene-C(=O)—NR$^5$R$^6$, —NR$^5$—($C_1$-$C_6$)alkylene-C(=O)—NR$^6$R$^7$, —($C_0$-$C_6$)alkyl-NR$^5$C(=O)—R$^6$, —O—($C_2$-$C_6$)alkylene-NR$^5$C(=O)—R$^6$, —NR$^5$—($C_2$-$C_6$)alkylene-NR$^6$C(=O)—R$^7$, —($C_0$-$C_6$)alkyl-S(=O)$_2$—R$^5$, —($C_0$-$C_6$)alkyl-C(=O)—R$^5$, —O—($C_1$-$C_6$)alkylene-C(=O)—R$^5$ and —NR$^5$—($C_1$-$C_6$)alkylene-C(=O)—R$^6$;
R$^5$, R$^6$ and R$^7$ are each independently hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl;
M is an optionally substituted pyrimidyl ring;
P is selected from the group of a hydrogen or an optionally substituted radical selected from the group of —($C_0$-$C_6$)alkyl-C(=O)—R$^9$, —($C_1$-$C_6$)alkyl-CN, —($C_2$-$C_6$)alkyl-S(O)—R$^9$, —($C_0$-$C_6$)alkyl-C(=O)NR$^9$R$^{10}$, —($C_2$-$C_6$)alkyl-NR$^9$C(=O)R$^{10}$ and —($C_0$-$C_6$)alkyl-S(O)$_2$—R$^9$; and
R$^9$ and R$^{10}$ are selected from the group of a hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl.

6. A compound according to claim 1 wherein:
A radical is selected from the group of hydrogen, halogen, —CN, —OH, —CF$_3$, —NH$_2$ and an optionally substituted radical selected from the group of —($C_1$-$C_6$)alkyl, —($C_1$-$C_6$)haloalkyl, —($C_3$-$C_7$)cycloalkyl, —($C_1$-$C_6$)cyanoalkyl, heterocycle, —($C_0$-$C_6$)alkyl-OR$^1$, —NR$^1$($C_2$-$C_6$)alkylene-OR$^2$ and —($C_0$-$C_6$)alkyl-NR$^1$R$^2$;
R$^1$ and R$^2$ are each independently hydrogen or an optionally substituted radical selected from the group of —($C_1$-$C_6$)haloalkyl, —($C_1$-$C_6$)alkyl, —($C_1$-$C_6$)cyanoalkyl, —($C_3$-$C_7$)cycloalkyl, —($C_4$-$C_{10}$)alkylene-cycloalkyl, heteroaryl, —($C_1$-$C_6$)alkylene-heteroaryl, aryl, heterocycle and —($C_1$-$C_6$)alkylene-aryl;
Any two radicals of R$^1$ or R$^2$ may be taken together to form an optionally substituted 3 to 10 membered carbocyclic or heterocyclic ring;
n is 1;
B radicals are each independently selected from the group of hydrogen, halogen, —CN, —OH, —CF$_3$, —NH$_2$ and an optionally substituted radical selected from the group of —($C_1$-$C_6$)alkyl, —($C_1$-$C_6$)haloalkyl, —($C_3$-$C_7$)cycloalkyl, aryl, heterocycle, —($C_0$-$C_6$)alkyl-OR$^5$, —NR$^5$ (C$_2$-C$_6$)alkylene-OR$^6$, —(C$_0$-C$_6$)alkyl-NR$^5$R$^6$, —(C$_0$-C$_6$)alkyl-S(=O)$_2$—R$^1$ and —(C$_0$-C$_6$)alkyl-C(=O)—R$^5$;

R$^5$ and R$^6$ are each independently hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

M is an optionally substituted heteroaryl or heterocycle;

P is selected from the group of a hydrogen or an optionally substituted radical selected from the group of —(C$_0$-C$_6$)alkyl-C(=O)—R$^9$, —(C$_0$-C$_6$)alkyl-C(=O)NR$^9$R$^{10}$, —(C$_2$-C$_6$)alkyl-NR$^9$C(=O)R$^{10}$ and —(C$_0$-C$_6$)alkyl-S(O)$_2$—R$^9$; and R$^9$ and R$^{10}$ are selected from the group of a hydrogen or an optionally substituted radical selected from the group of —(C$_1$-C$_6$)haloalkyl, —(C$_1$-C$_6$)alkyl, —(C$_1$-C$_6$)cyanoalkyl, —(C$_3$-C$_7$)cycloalkyl, —(C$_4$-C$_{10}$)alkylene-cycloalkyl, heteroaryl, —(C$_1$-C$_6$)alkylene-heteroaryl, aryl, heterocycle and —(C$_1$-C$_6$)alkylene-aryl;

with the proviso that the compound is not:

4-(3-Methyl-1H-pyrazol-4-yl)-N-(pyridin-2-yl)thiazol-2-amine;
N-(Pyridin-2-yl)-4-(3-(trifluoromethyl)-1H-pyrazol-4-yl)thiazol-2-amine;
4-(3-Isopropyl-1H-pyrazol-4-yl)-N-(pyridin-2-yl)thiazol-2-amine;
5-Methyl-4-(3-methyl-1H-pyrazol-4-yl)-N-(pyridin-2-yl)thiazol-2-amine;
5-Methyl-4-(1H-pyrazol-4-yl)-N-(pyridin-2-yl)thiazol-2-amine;
5-Methyl-N-(6-methylpyridin-2-yl)-4-(1H-pyrazol-4-yl)thiazol-2-amine;
5-Methyl-N-(4-methylpyridin-2-yl)-4-(1H-pyrazol-4-yl)thiazol-2-amine;
N-(3,5-Difluoropyridin-2-yl)-5-methyl-4-(1H-pyrazol-4-yl)thiazol-2-amine;
4-(3-Methyl-1H-pyrazol-4-yl)-N-(4-methylpyridin-2-yl)thiazol-2-amine;
5-Ethyl-4-(1H-pyrazol-4-yl)-N-(pyridin-2-yl)thiazol-2-amine;
4-(3-Methyl-1H-pyrazol-4-yl)-N-(6-methylpyridin-2-yl)thiazol-2-amine;
N-(5-Fluoropyridin-2-yl)-5-methyl-4-(1H-pyrazol-4-yl)thiazol-2-amine;
4-(1H-Pyrazol-4-yl)-N-(pyridin-2-yl)thiazol-2-amine;
2-Methyl-1-(4-(5-methyl-2-(pyridin-2-ylamino)thiazol-4-yl)-1H-pyrazol-1-yl)propan-1-one;
4-(5-Methyl-2-(pyridin-2-ylamino)thiazol-4-yl)-1H-pyrazole-1-carboxamide;
Cyclohexyl(4-(5-methyl-2-(pyridin-2-ylamino)thiazol-4-yl)-1H-pyrazol-1-yl)methanone;
2-Methyl-1-(4-(5-methyl-2-(6-methylpyridin-2-ylamino)thiazol-4-yl)-1H-pyrazol-1-yl)propan-1-one;
N-(6-Chloropyridin-2-yl)-5-methyl-4-(1H-pyrazol-4-yl)thiazol-2-amine;
5-Chloro-4-(1H-pyrazol-4-yl)-N-(pyridin-2-yl)thiazol-2-amine;
N-(6-Fluoropyridin-2-yl)-5-methyl-4-(1H-pyrazol-4-yl)thiazol-2-amine;
(4-(5-Methyl-2-(pyridin-2-ylamino)thiazol-4-yl)-1H-pyrazol-1-yl)(piperidin-1-yl)methanone;
5-Methyl-4-(1-(methylsulfonyl)-1H-pyrazol-4-yl)-N-(pyridin-2-yl)thiazol-2-amine;
N-(3-Fluoropyridin-2-yl)-5-methyl-4-(1H-pyrazol-4-yl)thiazol-2-amine;
4-(1H-Pyrazol-4-yl)-2-(pyridin-2-ylamino)thiazol-5-carbonitrile;
N-(6-Ethylpyridin-2-yl)-5-methyl-4-(1H-pyrazol-4-yl)thiazol-2-amine;
N-(6-Chloropyridin-2-yl)-4-(1H-pyrazol-4-yl)thiazol-2-amine;
N-Isopropyl-4-(5-methyl-2-(pyridin-2-ylamino)thiazol-4-yl)-1H-pyrazole-1-carboxamide;
N-(6-Fluoropyridin-2-yl)-4-(1H-pyrazol-4-yl)thiazol-2-amine;
5-Chloro-N-(6-methylpyridin-2-yl)-4-(1H-pyrazol-4-yl)thiazol-2-amine;
N-(6-Methylpyridin-2-yl)-4-(1H-pyrazol-4-yl)thiazol-2-amine;
4-(1H-Pyrazol-4-yl)-N-(pyridin-2-yl)-5-(trifluoromethyl)thiazol-2-amine;
5-Phenyl-4-(1H-pyrazol-4-yl)-N-(pyridin-2-yl)thiazol-2-amine;
5-Fluoro-4-(1H-pyrazol-4-yl)-N-(pyridin-2-yl)thiazol-2-amine;
(4-(1H-Pyrazol-4-yl)-2-(pyridin-2-ylamino)thiazol-5-yl)methanol;
N-(6-Methoxypyridin-2-yl)-5-methyl-4-(1H-pyrazol-4-yl)thiazol-2-amine;
N-Cyclopropyl-4-(5-methyl-2-(pyridin-2-ylamino)thiazol-4-yl)-1H-pyrazole-1-carboxamide;
4-(3-Cyclopropyl-1H-pyrazol-4-yl)-N-(pyridin-2-yl)thiazol-2-amine;
4-(3-Ethyl-1H-pyrazol-4-yl)-N-(pyridin-2-yl)thiazol-2-amine; and
4-(2-(6-Fluoropyridin-2-ylamino)-5-methylthiazol-4-yl)-1H-pyrazole-1-carboxamide.

7. A compound as in any one of claims 1-6, which can exist as optical isomers, wherein said compound is either the racemic mixture or one or both of the individual optical isomers.

8. A compound according to claim 1, wherein said compound is selected from:

6-(5-Methyl-4-(1H-pyrazol-4-yl)thiazol-2-ylamino)picolinonitrile;
5-Morpholino-4-(1H-pyrazol-4-yl)-N-(pyridin-2-yl)thiazol-2-amine;
2-(5-Methyl-4-(1H-pyrazol-4-yl)thiazol-2-ylamino)nicotinonitrile;
5-(Piperidin-1-yl)-4-(1H-pyrazol-4-yl)-N-(pyridin-2-yl)thiazol-2-amine;
4-(3-(Furan-2-yl)-1H-pyrazol-4-yl)-N-(pyridin-2-yl)thiazol-2-amine;
4-(3-(Cyclopropylmethyl)-1H-pyrazol-4-yl)-N-(pyridin-2-yl)thiazol-2-amine;
4-(3-Isobutyl-1H-pyrazol-4-yl)-N-(pyridin-2-yl)thiazol-2-amine;
4-(1H-Pyrazol-4-yl)-N-(pyridin-2-yl)-5-(pyrrolidin-1-yl)thiazol-2-amine;
4-(1-(4-Chlorophenylsulfonyl)-1H-pyrazol-4-yl)-5-methyl-N-(pyridin-2-yl)thiazol-2-amine;
5-Fluoro-N-(6-fluoropyridin-2-yl)-4-(1H-pyrazol-4-yl)thiazol-2-amine;
5-Fluoro-N-(6-methylpyridin-2-yl)-4-(1H-pyrazol-4-yl)thiazol-2-amine;
N$^5$,N$^5$-Dimethyl-4-(1H-pyrazol-4-yl)-N$^2$-(pyridin-2-yl)thiazole-2,5-diamine;
N-(6-Chloropyridin-2-yl)-5-fluoro-4-(1H-pyrazol-4-yl)thiazol-2-amine;
N-(6-Iodopyridin-2-yl)-5-methyl-4-(1H-pyrazol-4-yl)thiazol-2-amine;
N-(3-Iodopyridin-2-yl)-5-methyl-4-(1H-pyrazol-4-yl)thiazol-2-amine;

5-Methyl-4-(1H-pyrazol-4-yl)-N-(pyrimidin-2-yl)thiazol-2-amine;
4-(5-Chloro-1H-pyrazol-4-yl)-N-(pyridin-2-yl)thiazol-2-amine;
5-(Methoxymethyl)-4-(1H-pyrazol-4-yl)-N-(pyridin-2-yl)thiazol-2-amine;
N-(4-Fluoropyridin-2-yl)-5-methyl-4-(1H-pyrazol-4-yl)thiazol-2-amine;
5-((Diethylamino)methyl)-4-(1H-pyrazol-4-yl)-N-(pyridin-2-yl)thiazol-2-amine;
5-(Morpholinomethyl)-4-(1H-pyrazol-4-yl)-N-(pyridin-2-yl)thiazol-2-amine;
5-(Ethoxymethyl)-4-(1H-pyrazol-4-yl)-N-(pyridin-2-yl)thiazol-2-amine;
N-(3-Fluoro-6-methylpyridin-2-yl)-5-methyl-4-(1H-pyrazol-4-yl)thiazol-2-amine;
N-(5-Methoxypyridin-2-yl)-5-methyl-4-(1H-pyrazol-4-yl)thiazol-2-amine;
5-Fluoro-N-(pyrazin-2-yl)-4-(1H-pyrazol-4-yl)thiazol-2-amine;
4-(2-(Pyridin-2-ylamino)thiazol-4-yl)-1H-pyrazole-5-carbonitrile;
N-(1-Methyl-1H-pyrazol-3-yl)-4-(1H-pyrazol-4-yl)thiazol-2-amine;
5-Fluoro-N-(5-fluoropyridin-2-yl)-4-(1H-pyrazol-4-yl)thiazol-2-amine;
N-(Pyridin-2-yl)-4-(3-(2,2,2-trifluoroethyl)-1H-pyrazol-4-yl)thiazol-2-amine;
4-(5-Fluoro-2-(6-methylpyridin-2-ylamino)thiazol-4-yl)-1H-pyrazole-1-carboxamide;
N-(4-Methylpyrimidin-2-yl)-4-(1H-pyrazol-4-yl)thiazol-2-amine;
N-Methyl-2-(4-(5-methyl-2-(pyridin-2-ylamino)thiazol-4-yl)-1H-pyrazol-1-yl)acetamide;
5-Methyl-N-(4-methylpyrimidin-2-yl)-4-(1H-pyrazol-4-yl)thiazol-2-amine;
5-Methyl-N-(5-methylpyrimidin-2-yl)-4-(1H-pyrazol-4-yl)thiazol-2-amine; and
4-(3-Fluoro-1H-pyrazol-4-yl)-N-(pyridin-2-yl)thiazol-2-amine;
  or a pharmaceutically acceptable acid or base addition salt thereof, a stereochemically isomeric form thereof and an N-oxide form thereof.
9. A compound according to claim 1, wherein said compound is selected from:
N,N-Dimethyl-4-(5-methyl-2-(pyridin-2-ylamino)thiazol-4-yl)-1H-pyrazole-1-carboxamide;
4-(3-Phenyl-1H-pyrazol-4-yl)-N-(pyridin-2-yl)thiazol-2-amine;
5-Methyl-4-(1H-pyrazol-4-yl)-N-(pyrimidin-4-yl)thiazol-2-amine;
4-(3-(Phenylsulfonyl)-1H-pyrazol-4-yl)-N-(pyridin-2-yl)thiazol-2-amine;
4-(3-(Methoxymethyl)-1H-pyrazol-4-yl)-N-(pyridin-2-yl)thiazol-2-amine;
N-(2-Methylthiazol-4-yl)-4-(1H-pyrazol-4-yl)thiazol-2-amine;
4-(1H-Pyrazol-4-yl)-N-(thiazol-2-yl)thiazol-2-amine;
N-(6-(Fluoromethyl)pyridin-2-yl)-5-methyl-4-(1H-pyrazol-4-yl)thiazol-2-amine;
N-(6-(Difluoromethyl)pyridin-2-yl)-5-methyl-4-(1H-pyrazol-4-yl)thiazol-2-amine;
5-Chloro-4-(1H-pyrazol-4-yl)-N-(pyrimidin-2-yl)thiazol-2-amine;
N-(4-Ethylpyrimidin-2-yl)-5-methyl-4-(1H-pyrazol-4-yl)thiazol-2-amine;
N-(5-Fluoropyrimidin-2-yl)-5-methyl-4-(1H-pyrazol-4-yl)thiazol-2-amine;
4-(5-(Dimethylamino)-1H-pyrazol-4-yl)-N-(pyridin-2-yl)thiazol-2-amine;
5-Chloro-N-(4-methylpyrimidin-2-yl)-4-(1H-pyrazol-4-yl)thiazol-2-amine;
3-(4-(1H-Pyrazol-4-yl)thiazol-2-ylamino)-1-methylpyrrolidin-2-one;
4-(1H-Pyrazol-4-yl)-N-(pyrimidin-2-yl)-5-(trifluoromethyl)thiazol-2-amine;
N-(4-Isopropylpyrimidin-2-yl)-5-methyl-4-(1H-pyrazol-4-yl)thiazol-2-amine;
N-(4-Methoxypyrimidin-2-yl)-4-(1H-pyrazol-4-yl)thiazol-2-amine;
1-(4-(2-(4-Methylpyrimidin-2-ylamino)thiazol-4-yl)-1H-pyrazol-5-yl)ethanone;
N-(5-Fluoropyrimidin-2-yl)-4-(1H-pyrazol-4-yl)thiazol-2-amine;
4-(5-(Dimethylamino)-1H-pyrazol-4-yl)-N-(4-methylpyrimidin-2-yl)thiazol-2-amine;
N-(4-Methylpyrimidin-2-yl)-4-(3-(piperidin-1-yl)-1H-pyrazol-4-yl)thiazol-2-amine;
N-(4-Methylpyrimidin-2-yl)-4-(1H-pyrazol-4-yl)-5-(trifluoromethyl)thiazol-2-amine;
4-(1H-Pyrazol-4-yl)-N-(pyrimidin-2-yl)thiazol-2-amine;
N-(4-Methylpyrimidin-2-yl)-4-(3-morpholino-1H-pyrazol-4-yl)thiazol-2-amine;
N-((4-(5-Methyl-2-(pyridin-2-ylamino)thiazol-4-yl)-1H-pyrazol-1-yl)methyl)acetamide;
N-(4-Cyclopropylpyrimidin-2-yl)-5-methyl-4-(1H-pyrazol-4-yl)thiazol-2-amine;
(4-(5-Methyl-2-(pyridin-2-ylamino)thiazol-4-yl)-1H-pyrazol-1-yl)(pyridin-2-yl)methanone;
4-(5-(Diethylamino)-1H-pyrazol-4-yl)-N-(4-methylpyrimidin-2-yl)thiazol-2-amine;
4-(5-(Dimethylamino)-1H-pyrazol-4-yl)-N-(pyrimidin-2-yl)thiazol-2-amine;
Cyclopropyl(4-(2-(pyrimidin-2-ylamino)thiazol-4-yl)-1H-pyrazol-5-yl)methanone;
1-(4-(2-(Pyrimidin-2-ylamino)thiazol-4-yl)-1H-pyrazol-5-yl)ethanone;
$N^5$-(2-Methoxyethyl)-$N^5$-methyl-4-(1H-pyrazol-4-yl)-$N^2$-(pyrimidin-2-yl)thiazole-2,5-diamine;
N-(5-Fluoro-4-methylpyrimidin-2-yl)-4-(1H-pyrazol-4-yl)thiazol-2-amine;
N-(5-Fluoro-4-methylpyrimidin-2-yl)-5-methyl-4-(1H-pyrazol-4-yl)thiazol-2-amine;
4-(3-(Ethyl(methyl)amino)-1H-pyrazol-4-yl)-N-(pyrimidin-2-yl)thiazol-2-amine;
4-(3-(Methylamino)-1H-pyrazol-4-yl)-N-(pyrimidin-2-yl)thiazol-2-amine;
4-(5-(4-Fluorophenyl)-1H-pyrazol-4-yl)-N-(pyrimidin-2-yl)thiazol-2-amine;
4-(5-(Methoxymethyl)-1H-pyrazol-4-yl)-N-(pyrimidin-2-yl)thiazol-2-amine;
5-Cyclobutyl-4-(1H-pyrazol-4-yl)-N-(pyrimidin-2-yl)thiazol-2-amine;
N-(Pyrimidin-2-yl)-4-(3-(pyrrolidin-1-yl)-1H-pyrazol-4-yl)thiazol-2-amine;
4-(3-((2-Methoxyethyl)(methyl)amino)-1H-pyrazol-4-yl)-N-(pyrimidin-2-yl)thiazol-2-amine;
N-(4-Methylpyrimidin-2-yl)-4-(3-(pyrrolidin-1-yl)-1H-pyrazol-4-yl)thiazol-2-amine;
N-(4-Methylpyrimidin-2-yl)-4-(3-phenyl-1H-pyrazol-4-yl)thiazol-2-amine;
(4-(2-(4-Methylpyrimidin-2-ylamino)thiazol-4-yl)-1H-pyrazol-3-yl)methanol;

4-(3-(Methoxymethyl)-1H-pyrazol-4-yl)-N-(4-methylpyrimidin-2-yl)thiazol-2-amine;
4-(3-(Ethylamino)-1H-pyrazol-4-yl)-N-(4-methylpyrimidin-2-yl)thiazol-2-amine; and
4-(3-(2-Methoxyethyl)-1H-pyrazol-4-yl)-N-(4-methylpyrimidin-2-yl)thiazol-2-amine;

or a pharmaceutically acceptable acid or base addition salt thereof, a stereochemically isomeric form thereof and an N-oxide form thereof.

10. A pharmaceutical composition comprising a therapeutically effective amount of a compound according to claim 1 and a pharmaceutically acceptable carrier and/or excipient.

11. A method of treating Parkinson's disease or Multiple Sclerosis, in a mammal, including a human, facilitated by the positive allosteric modulation of mGluR4, comprising administering to said mammal in need of such treatment a pharmaceutical composition comprising a therapeutically effective amount of a compound according to any one of claims 1 to 6 or 8 to 9.

12. A method of treating Parkinson's disease or Multiple Sclerosis-comprising administering to a mammalian patient in need of such treatment, a pharmaceutical composition comprising a therapeutically effective amount of a compound according to any one of claims 1 to 6 or 8 to 9 in combination with an agent selected from the group consisting of: levodopa, levodopa with a selective extracerebral decarboxylase inhibitor, carbidopa, entacapone, a COMT inhibitor or a dopamine agonist.

13. A method of modulating mGluR4 activity in a mammal comprising administering to said mammal a therapeutically effective amount of compound according to claim 1.

14. A method of modulating mGluR4 activity in a mammal comprising administering a therapeutically effective amount of a pharmaceutical composition according to claim 10.

* * * * *